US012708130B2

(12) United States Patent
Larsen et al.

(10) Patent No.: US 12,708,130 B2
(45) Date of Patent: Aug. 18, 2026

(54) SPRAY-DRIED COMPOSITION COMPRISING BETA-GALACTOSIDASE HAVING TRANSGALACTOSYLATING ACTIVITY IN COMBINATION WITH MALTODEXTRIN AND/OR NACL AND APPLICATION OF THE COMPOSITION

(71) Applicant: INTERNATIONAL N&H DENMARK APS, Kongens Lyngby (DK)

(72) Inventors: Morten Krog Larsen, Sabro (DK); Jens Damgaard, Copenhagen K (DK); Bjarne Larsen, Viby J (DK); Jacob Flyvholm Cramer, Højberg (DK)

(73) Assignee: INTERNATIONAL N&H DENMARK APS, Kongens Lyngby (DK)

( * ) Notice: Subject to any disclaimer, the term of this patent is extended or adjusted under 35 U.S.C. 154(b) by 487 days.

(21) Appl. No.: 18/318,084

(22) Filed: May 16, 2023

(65) Prior Publication Data

US 2023/0301335 A1 Sep. 28, 2023

Related U.S. Application Data

(63) Continuation of application No. 16/883,278, filed on May 26, 2020, now abandoned, which is a continuation of application No. 15/524,720, filed as application No. PCT/EP2015/075942 on Nov. 6, 2015, now abandoned.

(30) Foreign Application Priority Data

Nov. 7, 2014 (GB) ..................................... 1419900

(51) Int. Cl.

| | |
|---|---|
| ***A23L 29/00*** | (2016.01) |
| ***A23C 9/12*** | (2006.01) |
| ***A23C 9/158*** | (2006.01) |
| ***A23C 9/20*** | (2006.01) |
| ***A23L 29/30*** | (2016.01) |
| ***A23L 33/21*** | (2016.01) |
| ***A23P 10/40*** | (2016.01) |
| ***C12N 9/24*** | (2006.01) |
| ***C12N 9/38*** | (2006.01) |

(52) U.S. Cl.

CPC ............ *A23L 29/06* (2016.08); *A23C 9/1206* (2013.01); *A23C 9/158* (2013.01); *A23C 9/203* (2013.01); *A23L 29/015* (2016.08); *A23L 29/35* (2016.08); *A23L 33/21* (2016.08); *A23P 10/40* (2016.08); *C12N 9/2471* (2013.01); *C12Y 302/01023* (2013.01); *A23V 2002/00* (2013.01)

(58) Field of Classification Search

CPC ........ A23L 29/06; A23L 29/35; A23C 9/1206

See application file for complete search history.

(56) References Cited

U.S. PATENT DOCUMENTS

| | | | | |
|---|---|---|---|---|
| 4,944,952 | A | 7/1990 | Kobayashi et al. | |
| 6,022,725 | A | 2/2000 | Fowler et al. | |
| 6,268,328 | B1 | 7/2001 | Mitchinson et al. | |
| 9,107,440 | B2 | 8/2015 | Larsen et al. | |
| 2005/0180962 | A1* | 8/2005 | Raz ...................... | A61K 31/519 424/464 |
| 2006/0223140 | A1 | 10/2006 | Oura et al. | |
| 2008/0090276 | A1* | 4/2008 | Van Dyck ................ | C12N 9/96 435/182 |
| 2012/0040051 | A1 | 2/2012 | Chen et al. | |
| 2015/0223481 | A1 | 8/2015 | Larsen et al. | |
| 2017/0318849 | A1 | 11/2017 | Larsen et al. | |
| 2020/0397031 | A1 | 12/2020 | Larsen et al. | |

FOREIGN PATENT DOCUMENTS

| | | | |
|---|---|---|---|
| CN | 101396048 | A | 4/2009 |
| CN | 101845424 | A | 9/2010 |
| EP | 0323201 | A1 | 7/1989 |
| EP | 0458358 | A1 | 11/1991 |
| EP | 0224234 | B2 | 11/2001 |
| EP | 0215594 | B2 | 10/2003 |
| WO | 0190317 | A1 | 11/2001 |
| WO | 2008037839 | A1 | 4/2008 |
| WO | 2008088751 | A2 | 7/2008 |
| WO | 2009071539 | A1 | 6/2009 |
| WO | 2011120993 | A1 | 10/2011 |
| WO | 2012010597 | A1 | 1/2012 |
| WO | 2439270 | A2 | 4/2012 |
| WO | 2013182686 | A1 | 12/2013 |
| WO | 2015061135 | A1 | 4/2015 |
| WO | 2015086746 | A1 | 6/2015 |
| WO | 2016071504 | A1 | 5/2016 |

OTHER PUBLICATIONS

Alloue et al., 'Storage of Yarrowia lipolytica lipase after spray-drying in the presence of additives,' Process Biochemistry, 2007, pp. 1357-1361, vol. 42.

Belghith et al., Stabilization of Penicillium occitanis cellulases by spray drying in presence of Mallodextrin, Enzyme and Microbial Technology, 2001, pp. 253-258, vol. 28.

Bolotin et al., 'The complete genome sequence of the lactic acid bacterium *Lactococcus lactis* ssp. Lactis IL 1403,' Genome Research, May 31, 2001, pp. 731-753, vol. 11, No. 5.

Endress et al., 'Pectin'; '27.2.3'; In: Susan S. Cho and Nelson Almeida: 'Dietary Fiber and Health', Apr. 13, 2012, p. 392.

Ghorab et al., 'Waler-solid interactions between amorphous mal-lodexlrins and crystalline sodium chloride,' Food chemistry, 2014, pp. 26-35, vol. 144.

Gosling et al. 'Recent advances refining galactooligosaccharide production from lactose,' Feed Chemistry, Jul. 15, 0010, pp. 307-318, vol. 121, No. 2.

Hernandez-Hernandez et al., 'Characterization of galactooligosac-charides derived from lactulose,' Journal of Chromatography A, 2011, pp. 7691-7696, vol. 1218.

(Continued)

*Primary Examiner* — Jeffrey P Mornhinweg

(57) ABSTRACT

A spray-dried composition comprising an enzyme which is a β-galactosidase having transgalactosylating activity and a maltodextrin and/or sodium chloride.

5 Claims, 7 Drawing Sheets

Specification includes a Sequence Listing.

(56) References Cited

OTHER PUBLICATIONS

Hung et al., 'Purification and characterization of a recombinant B-galactosidase with transgalactosylalion activity from Bifidobaclerium infantis HL96,' Appl Microbiol. Biolechnol., 2002, pp. 439-445, vol. 58.
Razoqui et al., 'Substrate-like inhibition of the transgalactosylation reaction catalyzed by B-galactosidase from Aspergillus oryzae,' Biocatalysis and Biotransformation, 2013, pp. 57-65, vol. 31(1).
Jorgensen et al., 'High-efficiency synthesis of oligosaccharides with a truncated JI-galactosidase from Bifidobacterium bifidum,' Appl Microbiol Biotechnol., 2001, pp. 647-652, vol. 57.
Oliveira et al., Recombinant microbial systems for improved.
Otieno, 'Synthesis of 13-Galactooligosaccharides frorn Lactose Using Microbial B-Galactosidases,' Comprehensive Reviews in Food Science and Food Safety, 2010, vol. 9, pp. 4 71-482.
Perdana et al., 'Mimicking spray drying by drying of single droplets deposited on a flat service,' Food Bioprocess Technol., 2013, pp. 964-977, vol. 6.
Pokusaeva et al., 'Carbohydrate metabolism in Bifidobacteria,' Genes Nutr, 2011, pp. 285-306, vol. 6.
Rodriguez-Colinas et al., 'Galacto-Oligosaccharide dynthesis from lactose solution or skin milk using the II-Galactosidase from Bacillus circulans,' The Journal of Agricultural and Food Chemistry, 2012, pp. 6391-6398, vol. 60.
Schutyser et al., 'Single droplet drying for optimal spray drying of enzymes and probiotics,' Trends in Food Science & Technology, 2012, pp. 73-82, vol. 27.
Breekumar et al., 'Isolation and characterization of probiotic Bacillus subtilis SK09 from dairy effluent,' Indian Journal of Science and Technology, 2010, pp. 863-866, vol. 3, No. 8.
Vijayalaxmi et al., 'Production of Bioethanol from fermented sugars of sugarcane bagasse produced by gnocellulolytic enzymes of *Exiguobacterium* sp. VSG-1', Appl Biochem Biotechnol., 2013, pp. 246-260, vol. 171.
International Search Report issued for PCT/EP2015/075942 on Apr. 22, 2016.
Written Opinion issued for PCT/EP2015/075942 on Apr. 22, 2016.

* cited by examiner

Figure 1:
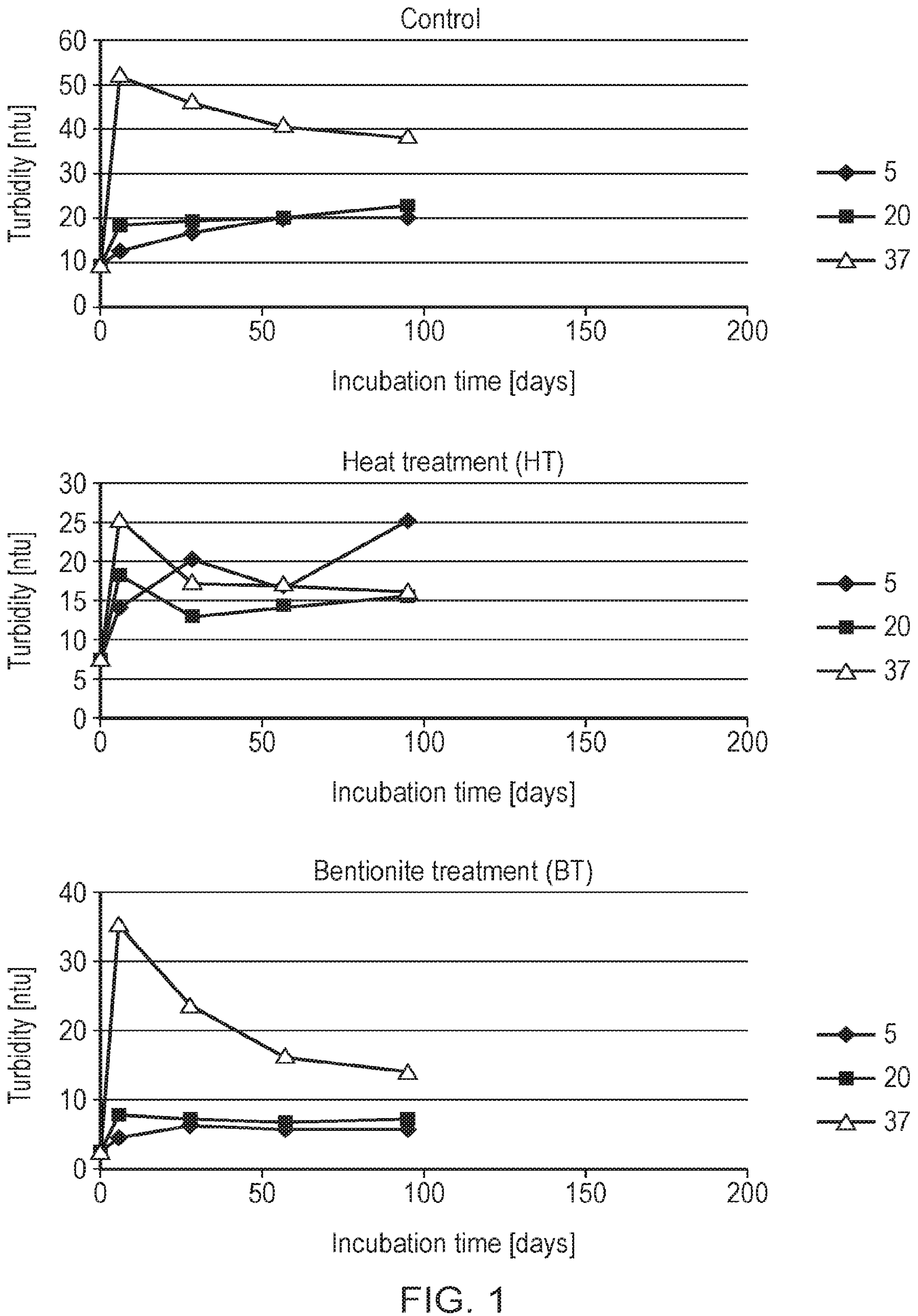
Figure 1:
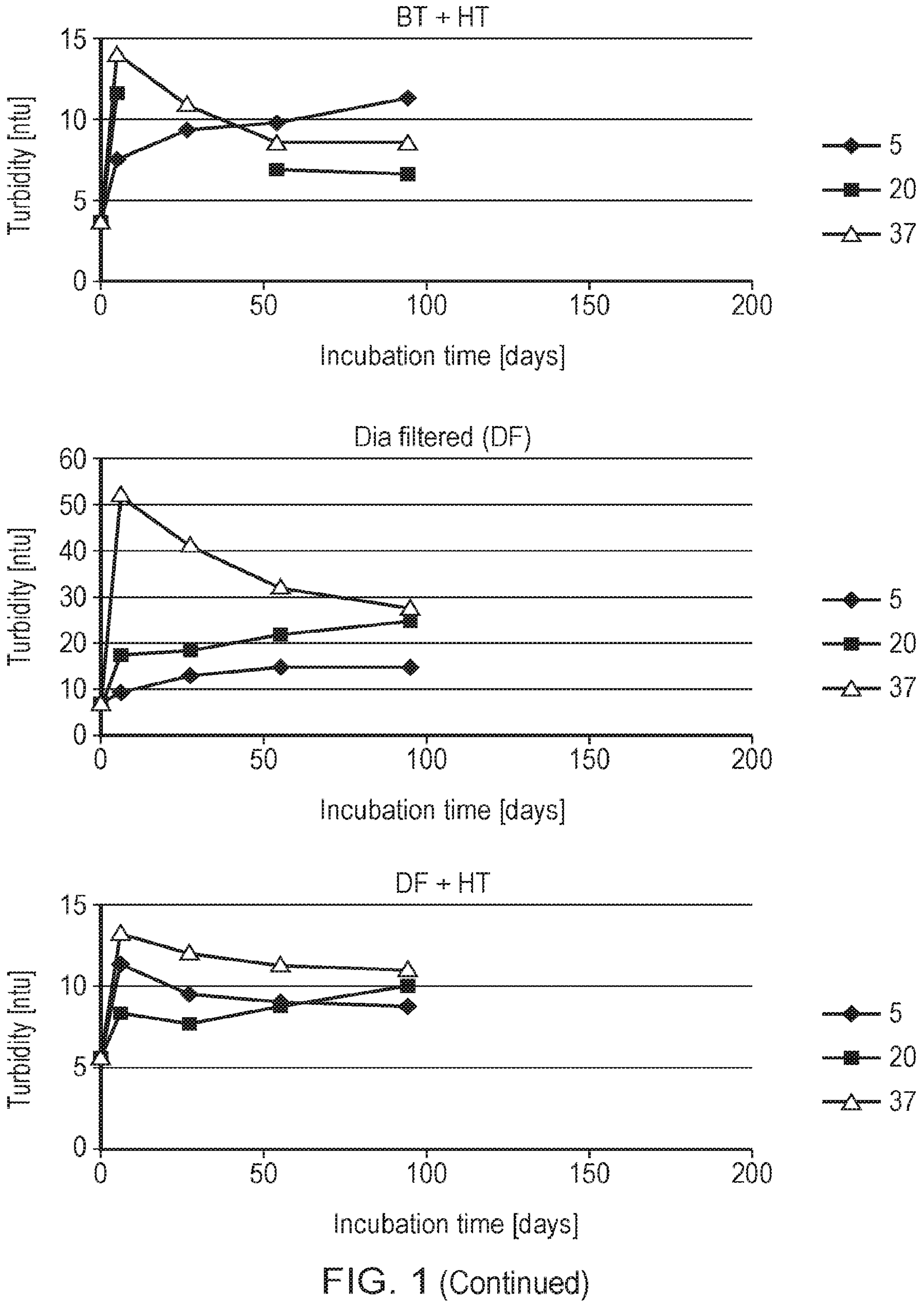

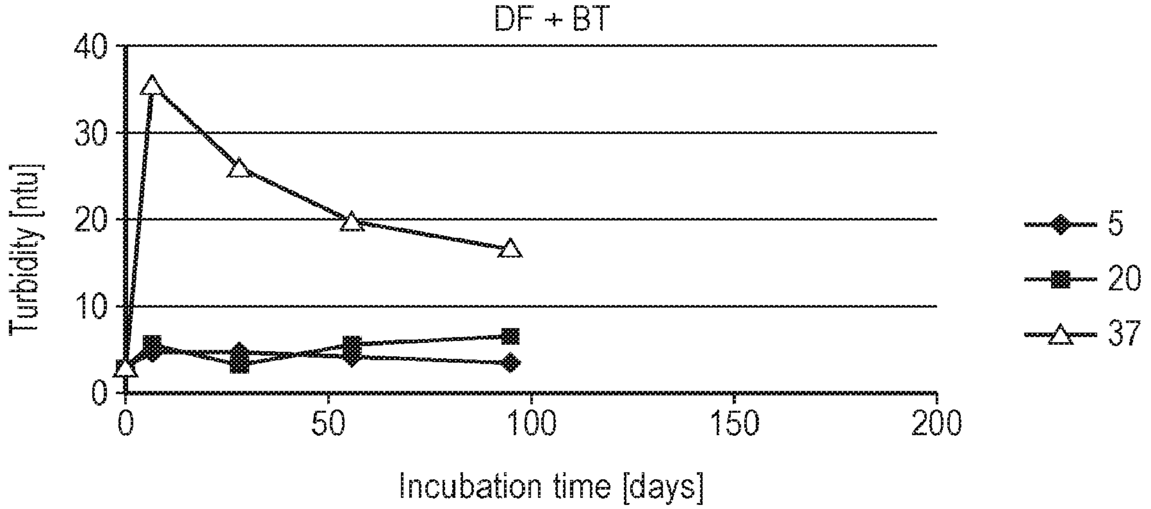
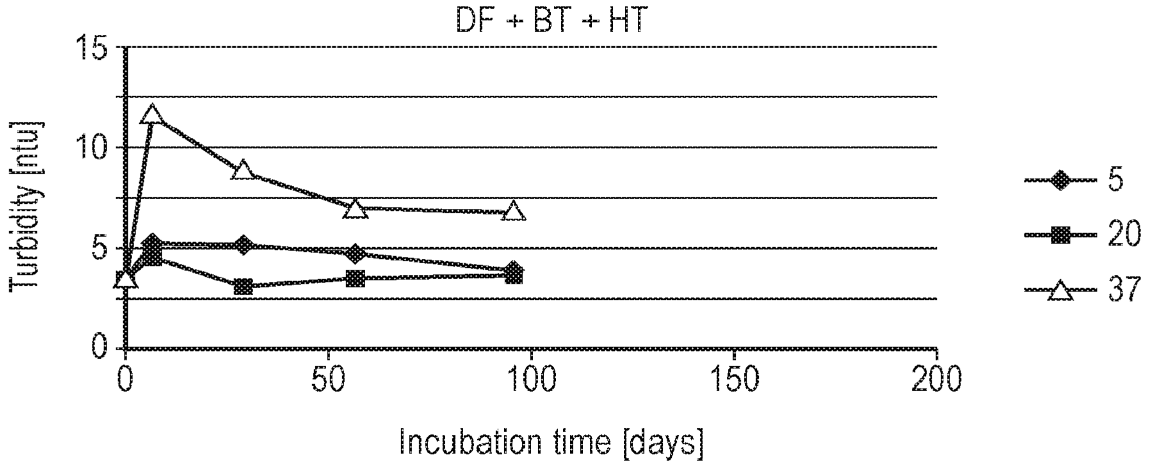
FIG. 1 (Continued)

Results collected:

Sample 1

| | | Activity, LAU/g: | Relative activity, % |
|---|---|---|---|
| 0 | t=0 | 2814 | 100 |
| 5°C | 6 months 5°C | 2743 | 97 |
| 20°C | 6 months 20°C | 2301 | 82 |
| 37°C | 6 months 37°C | 736 | 26 |

Sample 3

| | | Activity, LAU/g: | Relative activity, % |
|---|---|---|---|
| 0 | t=0 | 2126 | 100 |
| 5°C | 6 months 5°C | 2172 | 102 |
| 20°C | 6 months 20°C | 2006 | 94 |
| 37°C | 6 months 37°C | 1401 | 66 |

Sample 5

| | | Activity, LAU/g: | Relative activity, % |
|---|---|---|---|
| 0 | t=0 | 2414 | 100 |
| 5°C | 6 months 5°C | 2480 | 103 |
| 20°C | 6 months 20°C | 2366 | 98 |
| 37°C | 6 months 37°C | 2167 | 90 |

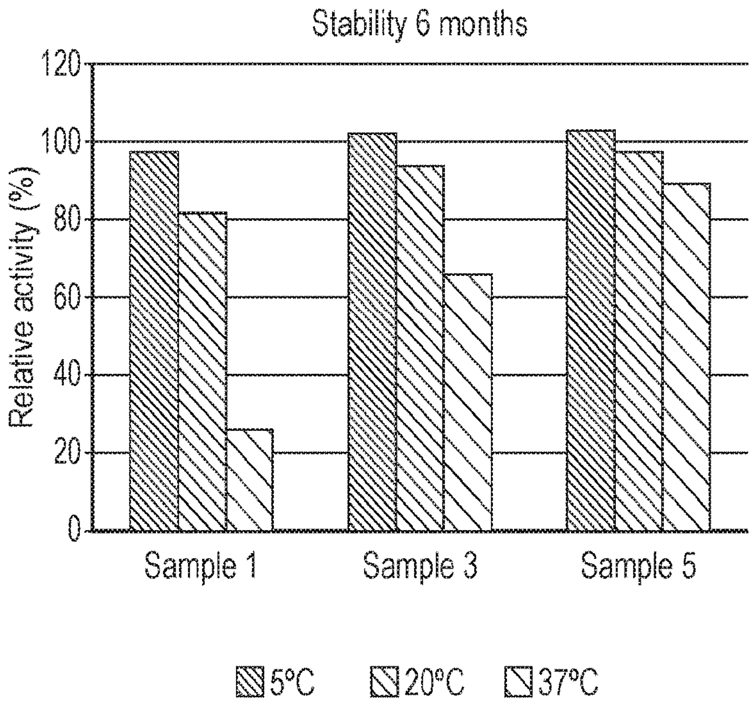

The activity for Pno 622 6 months at 37°C has a CV% at 5,9%
All the other samples has a CV% below 5% as described in the protocol

FIG. 4

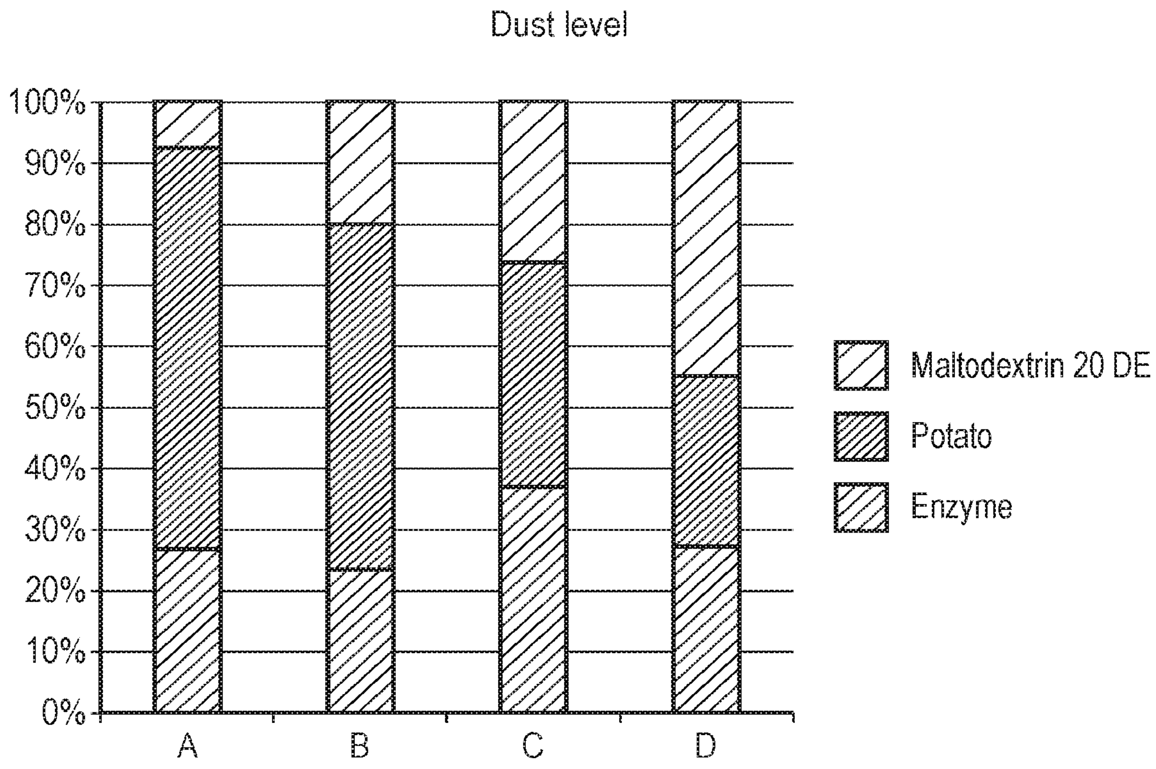
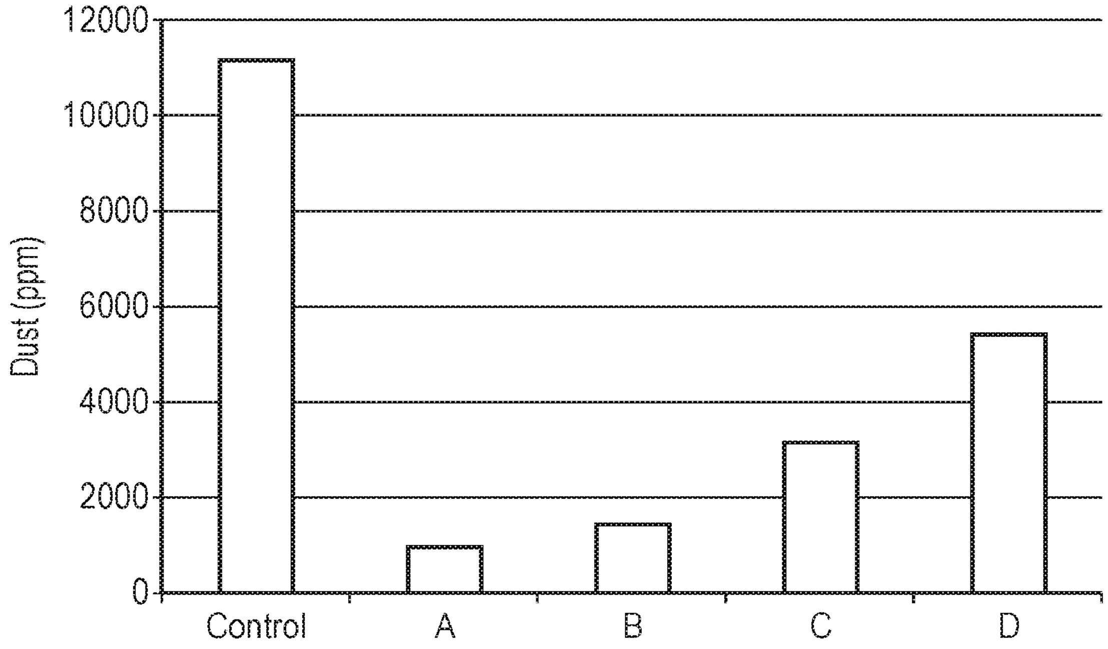
FIG. 5

SPRAY-DRIED COMPOSITION COMPRISING BETA-GALACTOSIDASE HAVING TRANSGALACTOSYLATING ACTIVITY IN COMBINATION WITH MALTODEXTRIN AND/OR NACL AND APPLICATION OF THE COMPOSITION

CROSS-REFERENCE TO RELATED APPLICATIONS

This application is a continuation of U.S. application Ser. No. 16/883,278, filed May 26, 2020, which is a continuation of U.S. application Ser. No. 15/524,720, filed May 5, 2017, now abandoned, which is a U.S. National Stage Application under 35 U.S.C. § 371 of International Patent Application No. PCT/EP2015/075942, filed Nov. 6, 2015, which claims priority to GB Application No. 1419900.4, filed Nov. 7, 2014, the disclosure of each of which is incorporated by reference herein in its entirety.

INCORPORATION BY REFERENCE OF THE SEQUENCE LISTING

The sequence listing provided in the file named "NB40872USCNT_SL.xml" with a size of 61 KB which was created on May 11, 2023, and which is filed herewith, is incorporated by reference herein in its entirety.

FIELD OF THE INVENTION

This invention relates to polypeptide-containing particles, to processes for preparing polypeptide-containing particles, and to the use of peptide-containing particles.

BACKGROUND TO THE INVENTION

Galactooligosaccharides (GOS) are carbohydrates which are nondigestable in humans and animals comprising two or more galactose molecules, typically up to nine, linked by glycosidic bonds. GOS's may also include one or more glucose molecules. One of the beneficial effects of GOS's is their ability of acting as prebiotic compounds by selectively stimulating the proliferation of beneficial colonic microorganisms such as bacteria to give physiological benefits to the consumer. The established health effects have resulted in a growing interest in GOSs as food ingredients for various types of food.

The enzyme 3-galactosidase (EC 3.2.1.23) usually hydrolyses lactose to the monosaccharides D-glucose and D-galactose. In the normal enzyme reaction of β-galactosidases, the enzyme hydrolyses lactose and transiently binds the galactose monosaccharide in a galactose-enzyme complex that transfers galactose to the hydroxyl group of water, resulting in the liberation of D-galactose and D-glucose. However, at high lactose concentrations some β-galactosidases are able to transfer galactose to the hydroxyl groups of D-galactose or D-glucose in a process called transgalactosylation whereby galacto-oligosaccharides are produced. Also at high lactose concentrations some β-galactosidases are able to transfer galactose to the hydroxyl groups of lactose or higher order oligosaccharides.

The genus *Bifidobacterium* is one of the most commonly used types of bacteria cultures in the dairy industry for fermenting a variety of diary products. Ingestion of *Bifidobacterium*-containing products furthermore has a health-promoting effect. This effect is not only achieved by a lowered pH of the intestinal contents but also by the ability of *Bifidobacterium* to repopulate the intestinal flora in individuals who have had their intestinal flora disturbed by for example intake of antibiotics. *Bifidobacterium* furthermore has the potential of outcompeting potential harmful intestinal micro-organisms.

Galacto-oligosaccharides are known to enhance the growth of *Bifidobacterium*. This effect is likely achieved through the unique ability of *Bifidobacterium* to exploit galacto-oligosaccharides as a carbon source. Dietary supplement of galacto-oligosaccharides is furthermore thought to have a number of long-term disease protecting effects. For example, galacto-oligosaccharide intake has been shown to be highly protective against development of colorectal cancer in rats. There is therefore a great interest in developing cheap and efficient methods for producing galacto-oligosaccharides for use in the industry for improving dietary supplements and dairy products.

An extracellular lactase from *Bifidobacterium bifidum* DSM20215 truncated with approximately 580 amino acids (BIF3-d3) has been described as a transgalactosylating enzyme in a solution containing lactose solubilised in water (Jorgensen et al. (2001), Appl. Microbiol. Biotechnol., 57: 647-652). WO 01/90317 also describes a truncation variant (OLGA347) as being a transgalactosylating enzyme and in WO 2012/010597 OLGA347 was shown to transfer a galactose moiety to D-fucose, N-acetyl-galactosamine and xylose.

In WO 2009/071539 a differently truncated fragment compared to BIF3-d3 is described as resulting in efficient hydrolysis and very low production of GOS when tested in milk.

In WO 2013/182686 we describe a polypeptide which has a useful ratio of transgalactosylation to hydrolysis activity and thus is an efficient producer of GOS when incubated with lactose even at low lactose levels such as in a milk-based product.

There is still a need however to provide improved formulations for such enzymes. These products should provide the enzyme product with desired properties such as enzyme storage stability. The present invention addresses this need.

Surprising Features and Advantages of the Invention

Current commercial lactase products are formulated as liquids, e.g. in polyols such as glycerol. It is believed that such formulations are physically stable in that the enzyme is stable over an acceptable shelf life for the product.

We investigated formulating a polypeptide having transgalactosylating activity in glycerol. Using turbidity as a measure of precipitation, we found that the physical stability of such a formulation was acceptable.

However, when we investigated the activity of such a formulation we found that contrary to expectations, the presence of a polyol (e.g., glycerol) perturbed the transgalactosylation activity of the enzyme. In particular, we found that in the presence of a polyol there was a tendency for a galactosyl-glycerol to be generated instead of the desired GOS. Surprisingly, we found that a spray-dried product comprising a lactase in which a maltodextrin (or a combination of maltodextrins) or sodium chloride is used as a carrier is both physically stable and retains the transgalactosylation activity of the enzyme allowing for the synthesis of the desired GOS.

SUMMARY OF THE INVENTION

It is an aim of embodiments of the invention to provide a formulation for a polypeptide which has a useful ratio of transgalactosylation to hydrolysis activity and in some embodiments where the polypeptide is an efficient producer of GOS when incubated with lactose even at low lactose levels such as in a milk-based product.

According to one aspect of the present invention there is provided a spray-dried composition comprising a polypeptide which is a β-galactosidase having transgalactosylating activity and a maltodextrin.

According to another aspect of the present invention there is provided a spray-dried composition comprising a polypeptide which is a β-galactosidase having transgalactosylating activity and sodium chloride.

According to another aspect of the present invention there is provided a spray-dried composition comprising a polypeptide which is a β-galactosidase having transgalactosylating activity and maltodextrin and/or sodium chloride.

In one embodiment wherein the polypeptide is an enzyme which is classified in Enzyme Classification (E.C.) 3.2.1.23.

In one embodiment the polypeptide has a ratio of transgalactosylating activity:β-galactosidase activity of at least 0.5, at least 1, at least 2, at least 2.5, at least 3, at least 4, at least 5, at least 6, at least 7, at least 8, at least 9, at least 10, at least 11, or at least 12 at or above a concentration of 3% w/w initial lactose concentration.

In one embodiment the polypeptide having a transgalactosylating activity is selected from the group consisting of:

a. a polypeptide comprising an amino acid sequence having at least 90% sequence identity with SEQ ID NO: 1, wherein said polypeptide consists of at most 980 amino acid residues,
b. a polypeptide comprising an amino acid sequence having at least 97% sequence identity with SEQ ID NO: 2, wherein said polypeptide consists of at most 975 amino acid residues,
c. a polypeptide comprising an amino acid sequence having at least 96.5% sequence identity with SEQ ID NO: 3, wherein said polypeptide consists of at most 1300 amino acid residues,
d. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4 or 5; or ii) the complementary strand of i),
e. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and
f. a polypeptide comprising a deletion, insertion and/or conservative substitution of one or more amino acid residues of SEQ ID NO: 1, 2, 3, 4 or 5.

In one embodiment the polypeptide having transgalactosylating activity is selected from the group consisting of:

a. a polypeptide comprising an amino acid sequence having at least 96.5% sequence identity with SEQ ID NO: 3, wherein said polypeptide consists of at most 1300 amino acid residues,
b. a polypeptide comprising an amino acid sequence having at least 90% sequence identity with SEQ ID NO: 1, wherein said polypeptide consists of at most 980 amino acid residues,
c. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4, or 5; or ii) the complementary strand of i),
d. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and
e. a polypeptide comprising a deletion, insertion and/or conservative substitution of one or more amino acid residues of SEQ ID NO: 1, 2, 3, 4 or 5.

In one embodiment the polypeptide having transgalactosylating activity comprises or consists of the amino acid sequence of SEQ ID NO:1, 2, 3, 4 or 5.

In one embodiment the composition contain 0.1 wt % or less polyol.

In one embodiment the composition contains 0.1 wt % or less glycerol.

In one aspect, the particles of the spray dried composition have a volume mean diameter greater than 30 μm. In the present context, the particle size of a powder may be measured as "volume mean diameter" such as described by Rawle, A.: "Basic principles of particle size analysis" in Surface Coating International 2003, vol. 86, no 2, pp. 58-65. Measurement of particle size in the work leading to this patent has been performed by laser diffraction (also known as Low Angle Laser Light Scattering, or LALLS) using a particle size analyser model Mastersizer S from company Malvern Ltd, UK.

In one embodiment the polypeptide having transgalactosylating activity, which comprises an amino acid sequence having at least 90% sequence identity with SEQ ID NO: 1, and wherein said polypeptide, when being an expression product in a suitable host strain (e.g., *Bacillus subtilis*) comprising a nucleic acid sequence which encodes said polypeptide, is the only polypeptide expression product of said nucleic acid sequence that exhibits transgalactosylating activity.

In one embodiment the polypeptide is a C-terminal truncated fragment of SEQ ID NO:22 having transgalactosylating activity and which is stable against further truncation such as by proteolytic degradation when produced in a suitable organism such as *Bacillus subtilis* and/or which is stable against further truncation during storage after final formulation.

In one embodiment the polypeptide comprises an amino acid sequence having at least 90% sequence identity with SEQ ID NO: 1, wherein said polypeptide consists of at most 980 amino acid residues.

In one embodiment the polypeptide comprises an amino acid sequence having at least 97% sequence identity with SEQ ID NO: 2, wherein said polypeptide consists of at most 975 amino acid residues.

In one embodiment the polypeptide comprises an amino acid sequence having at least 96.5% sequence identity with SEQ ID NO: 3, wherein said polypeptide consists of at most 1300 amino acid residues.

In one aspect, disclosed herein is a composition comprising a spray-dried composition as described herein, preferably a food composition, more preferably a dairy product.

In one aspect, disclosed herein is a method for producing a food product such as a dairy product by treating a milk-based substrate comprising lactose with a spray-dried composition as described herein.

In one aspect, disclosed herein is a galacto-oligosaccharide or composition thereof obtained by treating a substrate comprising lactose with a spray-dried composition as described herein.

In one aspect, disclosed herein is a method of spray drying a liquid composition comprising:

(a) introducing a liquid composition into a spray drying apparatus, wherein the liquid composition comprises an enzyme as defined herein and a maltodextrin; and
(b) spray drying the liquid composition to produce particles.

In one aspect, disclosed herein is a method of spray drying a liquid composition comprising:

(a) introducing a liquid composition into a spray drying apparatus, wherein the liquid composition comprises an enzyme as defined herein and sodium chloride; and
(b) spray drying the liquid composition to produce particles.

LEGENDS TO THE FIGURE

Figure 2:
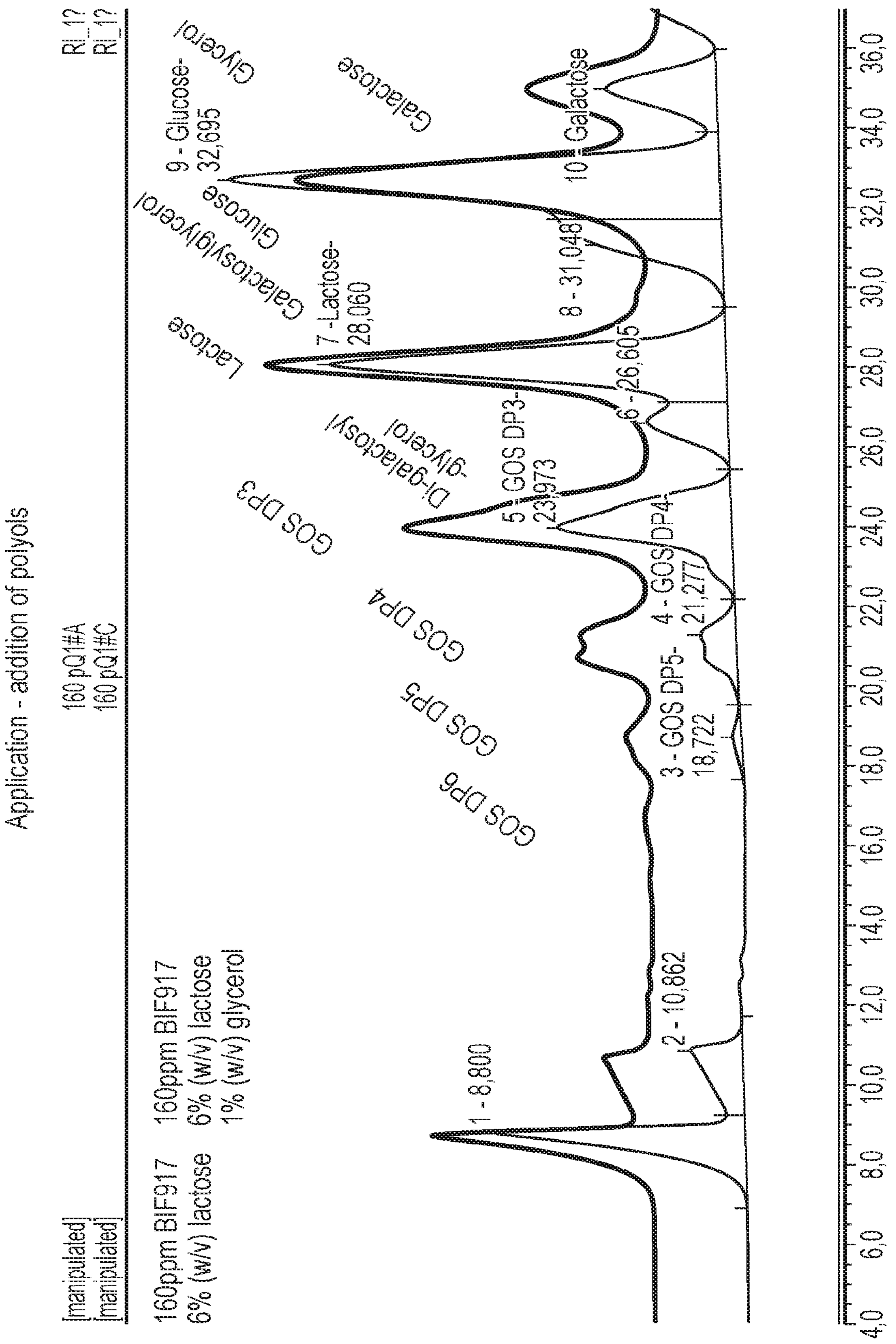
Figure 3:
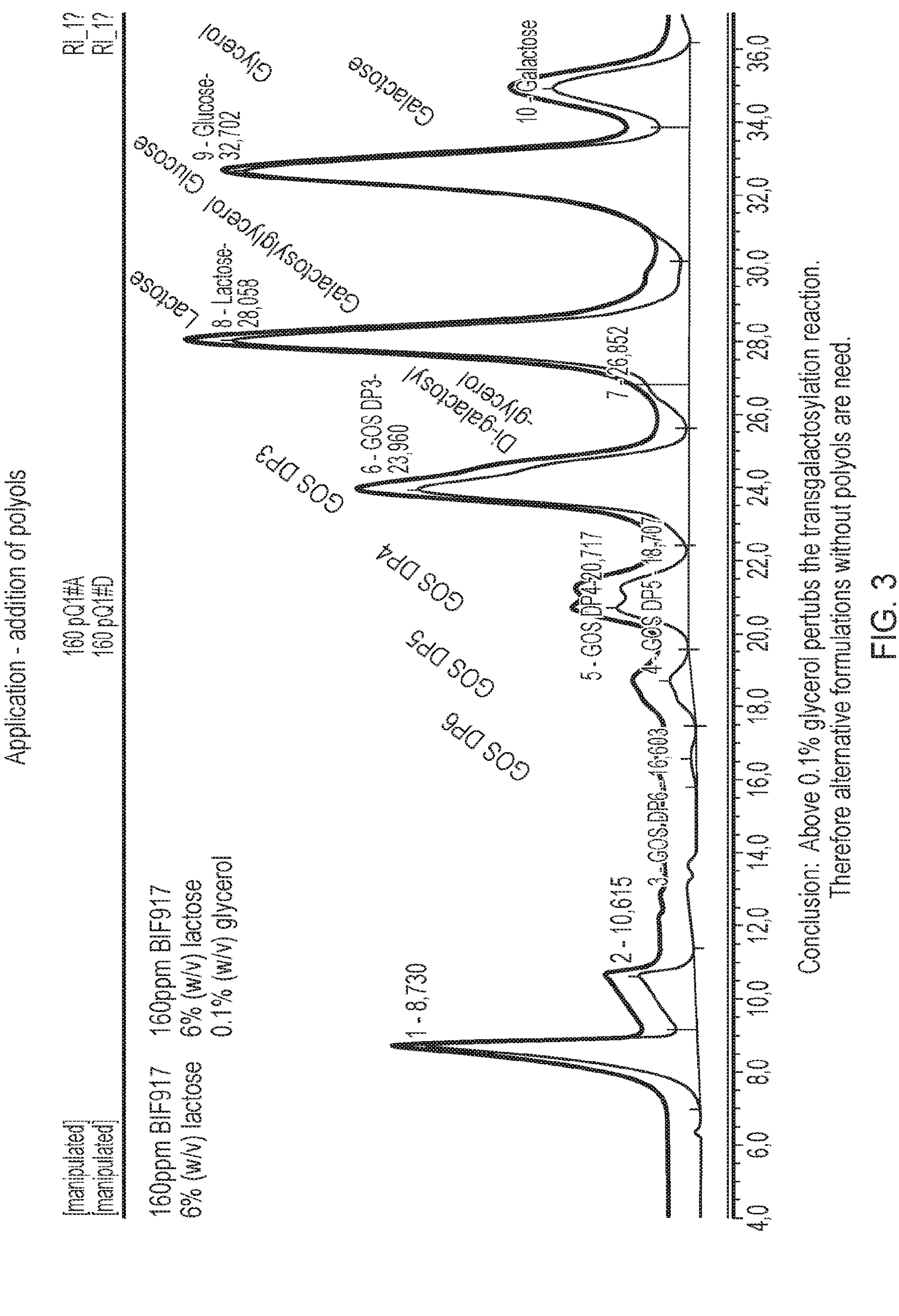

FIG. 1 shows the results of Example 1.
FIGS. 2 and 3 show the results of Example 2.
FIG. 4 shows the results of Example 3.
FIG. 5 shows the results of Example 4.

SEQUENCE LISTING

SEQ ID NO: 1 (also named (BIF_917) herein) is a 887 amino acid truncated fragment of SEQ ID NO: 22.

SEQ ID NO: 2 (also named (BIF_995) herein) is a 965 amino acid truncated fragment of SEQ ID NO: 22.

SEQ ID NO: 3 (also named (BIF_1068) herein) is a 1038 amino acid truncated fragment of SEQ ID NO: 22.

SEQ ID NO: 4 (also named (BIF_1172) herein) is a 1142 amino acid truncated fragment of SEQ ID NO: 22.

SEQ ID NO: 5 (also named (BIF_1241) herein) is a 1211 amino acid truncated fragment of SEQ ID NO: 22.

SEQ ID NO: 6 (also named (BIF_1326) herein) is a 1296 amino acid truncated fragment of SEQ ID NO: 22.

SEQ ID NO: 7 is *Bifidobacterium bifidum* glycoside hydrolase catalytic core

SEQ ID NO: 8 is a nucleotide sequence encoding an extracellular lactase from *Bifidobacterium bifidum* DSM20215

SEQ ID NO: 9 is nucleotide sequence encoding BIF_917

SEQ ID NO: 10 is nucleotide sequence encoding BIF_995

SEQ ID NO: 11 is nucleotide sequence encoding BIF 1068

SEQ ID NO: 12 is nucleotide sequence encoding BIF_1172

SEQ ID NO: 13 is nucleotide sequence encoding BIF_1241

SEQ ID NO: 14 is nucleotide sequence encoding BIF_1326

SEQ ID NO: 15 is forward primer for generation of above BIF variants

SEQ ID NO: 16 is reverse primer for BIF917

SEQ ID NO: 17 is reverse primer for BIF995

SEQ ID NO: 18 is reverse primer for BIF1068

SEQ ID NO: 19 is reverse primer for BIF1241

SEQ ID NO: 20 is reverse primer for BIF1326

SEQ ID NO: 21 is reverse primer for BIF1478

SEQ ID NO: 22 is extracellular lactase from *Bifidobacterium bifidum* DSM20215

SEQ ID NO: 23 is signal sequence of extracellular lactase from *Bifidobacterium bifidum* DSM20215.

DETAILED DISCLOSURE OF THE INVENTION

Definitions

In accordance with this detailed description, the following abbreviations and definitions apply. It should be noted that as used herein, the singular forms "a," "an," and "the" include plural referents unless the context clearly dictates otherwise. Thus, for example, reference to "a polypeptide" includes a plurality of such polypeptides, and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

"Transgalactosylase" means an enzyme that, among other things, is able to transfer galactose to the hydroxyl groups of D-galactose or D-glucose whereby galacto-oligosaccharides are produced. In one aspect, a transgalactosylase is identified by reaction of the enzyme on lactose in which the amount of galactose generated is less than the amount of glucose generated at any given time.

In the present context, the term "transgalactosylating activity" means the transfer of a galactose moiety to a molecule other than water. The activity can be measured as [glucose]-[galactose] generated at any given time during reaction or by direct quantification of the GOS generated at any given time during the reaction. This measurement may be performed in several ways such as by a HPLC method as shown in the examples. When comparing measurements of transgalactosylating activity, they have been performed at a given initial lactose concentration, such as e.g. 3, 4, 5, 6, 7, 8, 9 or 10% (w/w).

In the present context, the term "β-galactosidase activity" means the ability of an enzyme to hydrolyse β-galactosides such as for example lactose into monosaccharides, glucose and galactose.

In the context of calculating transgalactosylating activity: β-galactosidase activity, the β-galactosidase activity is measured as [galactose] generated at any given time during reaction.

This measurement may be performed in several ways such as by a HPLC method as shown in the examples.

In the present context, the term "ratio of transgalactosylation activity" using ortho-nitrophenol-β-D-galactopyranoside (ONPG) was calculated as follows: Ratio is calculated as ratio between Abs420 with acceptor present divided by Abs420 without acceptor present times 100. Variant at or below index 100 are purely hydrolytic variants, whereas the level above depicts relative transgalactosylating activity.

Ratio of transgalactosylation activity=$(Abs420^{+Cellobiose}/Abs420^{-Cellobiose})*100\%$, where $Abs420^{+Cellobiose}$ is the absorbance read at 420 nm using the described method 3 below including cellobiose in the reaction and Abs420-Cellobiose is the absorbance read at 420 nm using the described method 3 below but without cellobiose in the reaction. The equation above is only valid for dilutions where the absorbance is between 0.5 and 1.0.

In one aspect, the activity is measured after 15 min. reaction, 30 min. reaction, 60 min. reaction, 90 min. reaction, 120 min. reaction or 180 min. reaction. Thus in one aspect, as an example the relative transgalactosylation activity is measured 15 minutes after addition of enzyme, such as 30 minutes after addition of enzyme, such as 60 minutes after addition of enzyme, such as 90 minutes after addition of enzyme, such as 120 minutes after addition of enzyme or such as 180 minutes after addition of enzyme.

In the present context, the term "ratio of transgalactosylating activity:β-galactosidase activity" means ([Glucose]-[Galactose]/[Galactose]).

In the present context, the term [Glucose] means the glucose concentration in % by weight as measured by HPLC.

In the present context, the term [Galactose] means the galactose concentration in % by weight as measured by HPLC.

In the present context, the term "lactose has been transgalactosylated" means that a galactose molecule has been covalently linked to the lactose molecule such as for example covalently linked to any of the free hydroxyl groups in the lactose molecule or as generated by internal transgalactosylation for example forming allolactose.

In the present context, the evaluation of performance of polypeptides disclosed herein in galactooligosaccharide (GOS) production were tested in a "milk-based assay" (yogurt application mimic). Batch experiments with a volume of 100 μl were performed in 96 well MTP plates using a yogurt mix, consisting of 98.60% (w/v) fresh pasteurized low-fat milk (Arla Mini-mælk) and 1.4% (w/v) Nutrilac YQ-5075 whey ingredient (Arla). To completely hydrate Nutrilac YQ-5075 the mixture was left with agitation for 20 h and afterwards added 20 mM NaPhosphate pH 6.5 to ensure a pH of 6.5. This yogurt-base was either used plain or with various supplements such as additional lactose, fucose, maltose, xylose or salts. 90 μl of the yogurt was mixed with 10 μl purified enzyme or crude ferment, sealed with tape and incubated at 43° C. for 3 hours. The reaction was stopped by 100 μl 10% Na2CO3. Samples were stored at −20° C. Quantification of galactooligosaccharides (GOS), lactose, glucose and galactose were performed by H PLC. Analysis of samples was carried out on a Dionex ICS 3000. IC parameters were as follows: Mobile phase: 150 mM NaOH, Flow: Isochratic, 0.25 ml/min, Column: Carbopac PA1, Column temperature: RT, Injection volume: 10 μL, Detector: PAD, Integration: Manual, Sample preparation: 100 times dilution in Milli-Q water (0.1 ml sample+9.9 ml water) and filtration through 0.45 im syringe filters, Quantification: Peak areas in percent of peak area of the standard. A GOS syrup (Vivanal GOS, Friesland Campina) was used as standard for GOS quantification. Results of such an evaluation is shown in FIG. 4, and further described in example 2.

In the present context, the term "which polypeptide is spray-dried" means that the polypeptide has been obtained by spray-drying a polypeptide which is in solution or suspension at an appropriate temperature and for an appropriate period removing the water.

In the present context, the term "which polypeptide is in solution" relates to a polypeptide which is soluble in a solvent without precipitating out of solution. A solvent for this purpose includes any millieu in which the polypeptide may occur, such as an aqueous buffer or salt solution, a fermentation broth, or the cytoplasm of an expression host.

In the present context, the term "stabilizer" means any stabilizer for stabilizing the polypeptide e.g., a polyol such as, e.g., glycerol or propylene glycol, a sugar or a sugar alcohol, lactic acid, boric acid, or a boric acid derivative (e.g., an aromatic borate ester). In one aspect, the stabilizer is not a polyol, or the polyol is present at a level of 0.1 wt % or less.

The term "isolated" means that the polypeptide is at least substantially free from at least one other component with which the sequence is naturally associated in nature and as found in nature. In one aspect, "isolated polypeptide" as used herein refers to a polypeptide which is at least 30% pure, at least 40% pure, at least 60% pure, at least 80% pure, at least 90% pure, and at least 95% pure, as determined by SDS-PAGE.

The term "substantially pure polypeptide" means herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides disclosed herein are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods. Herein, the term "substantially pure polypeptide" is synonymous with the terms "isolated polypeptide" and "polypeptide in isolated form."

The term "purified" or "pure" means that a given component is present at a high level state—e.g. at least about 51% pure, such as at least 51% pure, or at least about 75% pure such as at least 75% pure, or at least about 80% pure such as at least 80% pure, or at least about 90% pure such as at least 90% pure, or at least about 95% pure such as at least 95% pure, or at least about 98% pure such as at least 98% pure. The component is desirably the predominant active component present in a composition.

The term "microorganism" in relation to the present invention includes any "microorganism" that could comprise a nucleotide sequence according to the present invention or a nucleotide sequence encoding for a polypeptide having the specific properties as defined herein and/or products obtained therefrom. In the present context, "microorganism" may include any bacterium or fungus being able to ferment a milk substrate.

The term "host cell"—in relation to the present invention includes any cell that comprises either a nucleotide sequence encoding a polypeptide having the specific properties as defined herein or an expression vector as described above and which is used in the production of a polypeptide having the specific properties as defined herein. In one aspect, the production is recombinant production.

The term "milk", in the context of the present invention, is to be understood as the lacteal secretion obtained from any mammal, such as cows, sheep, goats, buffaloes or camels.

In the present context, the term "milk-based substrate" means any raw and/or processed milk material or a material derived from milk constituents. Useful milk-based substrates include, but are not limited to solutions/suspensions of any milk or milk like products comprising lactose, such as whole or low fat milk, skim milk, buttermilk, reconstituted milk powder, condensed milk, solutions of dried milk, UHT milk, whey, whey permeate, acid whey, or cream. Preferably, the milk-based substrate is milk or an aqueous solution of skim milk powder. The milk-based substrate may be more concentrated than raw milk. In one embodiment, the milk-based substrate has a ratio of protein to lactose of at least 0.2, preferably at least 0.3, at least 0.4, at least 0.5, at least 0.6 or, most preferably, at least 0.7. The milk-based substrate may be homogenized and/or pasteurized according to methods known in the art.

"Homogenizing" as used herein means intensive mixing to obtain a soluble suspension or emulsion. It may be performed so as to break up the milk fat into smaller sizes so that it no longer separates from the milk. This may be accomplished by forcing the milk at high pressure through small orifices.

"Pasteurizing" as used herein means reducing or eliminating the presence of live organisms, such as microorganisms, in the milk-based substrate. Preferably, pasteurization is attained by maintaining a specified temperature for a specified period of time. The specified temperature is usually attained by heating. The temperature and duration may be selected in order to kill or inactivate certain bacteria, such as harmful bacteria, and/or to inactivate enzymes in the milk. A rapid cooling step may follow. A "food product" or "food composition" in the context of the present invention may be any comestible food or feed product suitable for consumption by an animal or human.

A "dairy product" in the context of the present invention may be any food product wherein one of the major constituents is milk-based. Preferable, the major constituent is milk-based. More preferably, the major constituent is a milk-based substrate which has been treated with an enzyme having transgalactosylating activity.

Maltodextrin is a polysaccharide that can be used as a food additive. Maltodextrin consists of D-glucose units connected in chains of variable length. The glucose units are primarily linked with $\alpha(1\rightarrow4)$ glycosidic bonds. Maltodextrin is typically composed of a mixture of chains that vary from three to seventeen glucose units long.

Maltodextrins are classified by DE (dextrose equivalent) and have a DE between 3 to 20. The higher the DE value, the shorter the glucose chains, the higher the sweetness, the higher the solubility and the lower heat resistance. Above DE 20, the European Union's CN code calls it glucose syrup, at DE 10 or lower the customs CN code nomenclature classifies maltodextrins as dextrins. The present invention may employ a mixture of such maltodextrins.

In the present context, "one of the major constituents" means a constituent having a dry matter which constitutes more than 20%, preferably more than 30% or more than 40% of the total dry matter of the dairy product, whereas "the major constituent" means a constituent having a dry matter which constitutes more than 50%, preferably more than 60% or more than 70% of the total dry matter of the dairy product.

A "fermented dairy product" in present context is to be understood as any dairy product wherein any type of fermentation forms part of the production process. Examples of fermented dairy products are products like yoghurt, buttermilk, creme fraiche, quark and fromage frais. Another example of a fermented dairy product is cheese. A fermented dairy product may be produced by any method known in the art.

The term "fermentation" means the conversion of carbohydrates into alcohols or acids through the action of a microorganism such as a starter culture. In one aspect, fermentation comprises conversion of lactose to lactic acid.

In the present context, "microorganism" may include any bacterium or fungus being able to ferment a milk substrate.

In the present context the term "Pfam domains" means regions within a protein sequence that are identified as either Pfam-A or Pfam-B based on multiple sequence alignments and the presence of Hidden Markov Motifs ("*The Pfam protein families database*": R. D. Finn, J. Mistry, J. Tate, P. Coggill, A. Heger, J. E. Pollington, O. L. Gavin, P. Gunesekaran, G. Ceric, K. Forslund, L. Holm, E. L. Sonnhammer, S. R. Eddy, A. Bateman Nucleic Acids Research (2010) Database Issue 38:D211-222). As examples of Pfam domains mention may be made of Glyco_hydro2N (PF02837), Glyco_hydro (PF00703), Glyco_hydro 2C (PF02836) and Bacterial Ig-like domain (group 4) (PF07532).

As used herein "a position corresponding to position" means that an alignment as described herein is made between a particular query polypeptide and the reference polypeptide. The position corresponding to a specific position in the reference polypeptide is then identified as the corresponding amino acid in the alignment with the highest sequence identity.

A "variant" or "variants" refers to either polypeptides or nucleic acids. The term "variant" may be used interchangeably with the term "mutant". Variants include insertions, substitutions, transversions, truncations, and/or inversions at one or more locations in the amino acid or nucleotide sequence, respectively. The phrases "variant polypeptide", "polypeptide variant", "polypeptide", "variant" and "variant enzyme" mean a polypeptide/protein that has an amino acid sequence that either has or comprises a selected amino acid sequence of or is modified compared to the selected amino acid sequence, such as SEQ ID NO: 1, 2, 3, 4 or 5.

As used herein, "reference enzymes," "reference sequence," "reference polypeptide" mean enzymes and polypeptides from which any of the variant polypeptides are based, e.g., SEQ ID NO: 1, 2, 3, 4 or 5. A "reference nucleic acid" means a nucleic acid sequence encoding the reference polypeptide.

As used herein, the terms "reference sequence" and "subject sequence" are used interchangeably.

As used herein, "query sequence" means a foreign sequence, which is aligned with a reference sequence in order to see if it falls within the scope of the present invention. Accordingly, such query sequence can for example be a prior art sequence or a third party sequence.

As used herein, the term "sequence" can either be referring to a polypeptide sequence or a nucleic acid sequence, depending of the context.

As used herein, the terms "polypeptide sequence" and "amino acid sequence" are used interchangeably.

The signal sequence of a "variant" may be the same or may differ from the signal sequence of the wild-type a *Bacillus* signal peptide or any signal sequence that will secrete the polypeptide. A variant may be expressed as a fusion protein containing a heterologous polypeptide. For example, the variant can comprise a signal peptide of another protein or a sequence designed to aid identification or purification of the expressed fusion protein, such as a His-Tag sequence.

To describe the various variants that are contemplated to be encompassed by the present disclosure, the following nomenclature will be adopted for ease of reference. Where the substitution includes a number and a letter, e.g., 592 P, then this refers to {position according to the numbering system/substituted amino acid}. Accordingly, for example, the substitution of an amino acid to proline in position 592 is designated as 592 P. Where the substitution includes a letter, a number, and a letter, e.g., D592 P, then this refers to {original amino acid/position according to the numbering system/substituted amino acid}.

Accordingly, for example, the substitution of alanine with proline in position 592 is designated as A592 P.

Where two or more substitutions are possible at a particular position, this will be designated by contiguous letters, which may optionally be separated by slash marks "/", e.g., G303ED or G303E/D.

Position(s) and substitutions are listed with reference to for example either SEQ ID NO: 1, 2, 3, 4 or 5. For example equivalent positions in another sequence may be found by aligning this sequence with either SEQ ID NO: 1, 2, 3, 4 or 5 to find an alignment with the highest percent identity and thereafter determining which amino acid aligns to correspond with an amino acid of a specific position of either SEQ ID NO: 1, 2, 3, 4 or 5. Such alignment and use of one sequence as a first reference is simply a matter of routine for one of ordinary skill in the art.

As used herein, the term "expression" refers to the process by which a polypeptide is produced based on the nucleic acid sequence of a gene. The process includes both transcription and translation.

As used herein, "polypeptide" is used interchangeably with the terms "amino acid sequence", "enzyme", "peptide" and/or "protein". As used herein, "nucleotide sequence" or "nucleic acid sequence" refers to an oligonucleotide sequence or polynucleotide sequence and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA.

"Homologue" means an entity having a certain degree of identity or "homology" with the subject amino acid sequences and the subject nucleotide sequences. In one aspect, the subject amino acid sequence is SEQ ID NO: 1, 2, 3, 4 or 5, and the subject nucleotide sequence preferably is SEQ ID NO: 9, 10, 11, 12 or 13.

A "homologous sequence" includes a polynucleotide or a polypeptide having a certain percent, e.g., 80%, 85%, 90%, 95%, or 99%, of sequence identity with another sequence. Percent identity means that, when aligned, that percentage of bases or amino acid residues are the same when comparing the two sequences. Amino acid sequences are not identical, where an amino acid is substituted, deleted, or added compared to the subject sequence. The percent sequence identity typically is measured with respect to the mature sequence of the subject protein, i.e., following removal of a signal sequence, for example. Typically, homologues will comprise the same active site residues as the subject amino acid sequence. Homologues also retain enzymatic activity, although the homologue may have different enzymatic properties than the wild-type.

As used herein, "hybridization" includes the process by which a strand of nucleic acid joins with a complementary strand through base pairing, as well as the process of amplification as carried out in polymerase chain reaction (PCR) technologies. The variant nucleic acid may exist as single- or double-stranded DNA or RNA, an RNA/DNA heteroduplex or an RNA/DNA copolymer. As used herein, "copolymer" refers to a single nucleic acid strand that comprises both ribonucleotides and deoxyribonucleotides. The variant nucleic acid may be codon-optimized to further increase expression.

As used herein, a "synthetic" compound is produced by in vitro chemical or enzymatic synthesis. It includes, but is not limited to, variant nucleic acids made with optimal codon usage for host organisms, such as a yeast cell host or other expression hosts of choice.

As used herein, "transformed cell" includes cells, including both bacterial and fungal cells, which have been transformed by use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

As used herein, "operably linked" means that the described components are in a relationship permitting them to function in their intended manner. For example, a regulatory sequence operably linked to a coding sequence is ligated in such a way that expression of the coding sequence is achieved under condition compatible with the control sequences.

As used herein, the term "fragment" is defined herein as a polypeptide having one or more (several) amino acids deleted from the amino and/or carboxyl terminus wherein the fragment has activity.

In one aspect, the term "fragment" is defined herein as a polypeptide having one or more (several) amino acids deleted from the amino and/or carboxyl terminus of the polypeptide of SEQ ID NO: 1, 2, 3, 4 or 5; wherein the fragment has transgalactosylating activity.

The term "Galactose Binding domain-like" as used herein is abbreviated to and interchangeable with the term "GBD".

Degree of Identity

The relatedness between two amino acid sequences or between two nucleotide sequences is described by the parameter "identity".

In one embodiment, the degree of sequence identity between a query sequence and a reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the length of the reference sequence.

In one embodiment, the degree of sequence identity between a query sequence and a reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the length of the longest of the two sequences.

In another embodiment, the degree of sequence identity between the query sequence and the reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the "alignment length", where the alignment length is the length of the entire alignment including gaps and overhanging parts of the sequences.

Sequence identity comparisons can be conducted by eye, or more usually, with the aid of readily available sequence comparison programs. These commercially available computer programs use complex comparison algorithms to align two or more sequences that best reflect the evolutionary events that might have led to the difference(s) between the two or more sequences. Therefore, these algorithms operate with a scoring system rewarding alignment of identical or similar amino acids and penalising the insertion of gaps, gap extensions and alignment of non-similar amino acids. The scoring system of the comparison algorithms include:

i) assignment of a penalty score each time a gap is inserted (gap penalty score), ii) assignment of a penalty score each time an existing gap is extended with an extra position (extension penalty score), iii) assignment of high scores upon alignment of identical amino acids, and iv) assignment of variable scores upon alignment of non-identical amino acids.

Most alignment programs allow the gap penalties to be modified. However, it is preferred to use the default values when using such software for sequence comparisons.

The scores given for alignment of non-identical amino acids are assigned according to a scoring matrix also called a substitution matrix. The scores provided in such substitution matrices are reflecting the fact that the likelihood of one amino acid being substituted with another during evolution varies and depends on the physical/chemical nature of the amino acid to be substituted. For example, the likelihood of a polar amino acid being substituted with another polar amino acid is higher compared to being substituted with a hydrophobic amino acid. Therefore, the scoring matrix will assign the highest score for identical amino acids, lower score for non-identical but similar amino acids and even lower score for non-identical non-similar amino acids. The most frequently used scoring matrices are the PAM matrices (Dayhoff et al. (1978), Jones et al. (1992)), the BLOSUM matrices (Henikoff and Henikoff (1992)) and the Gonnet matrix (Gonnet et al. (1992)).

Suitable computer programs for carrying out such an alignment include, but are not limited to, Vector NTI (Invitrogen Corp.) and the ClustalV, ClustalW and ClustalW2 programs (Higgins DG & Sharp PM (1988), Higgins et al. (1992), Thompson et al. (1994), Larkin et al. (2007). A selection of different alignment tools is available from the ExPASy Proteomics server at www.expasy.org. Another example of software that can perform sequence alignment is BLAST (Basic Local Alignment Search Tool), which is available from the webpage of National Center for Biotechnology Information which can currently be found at http://www.ncbi.nlm.nih.gov/ and which was firstly described in Altschul et al. (1990) J. Mol. Biol. 215; 403-410.

In a preferred embodiment of the present invention, the alignment program is performing a global alignment program, which optimizes the alignment over the full-length of the sequences. In a further preferred embodiment, the global alignment program is based on the Needleman-Wunsch algorithm (Needleman, Saul B.; and Wunsch, Christian D. (1970), "*A general method applicable to the search for similarities in the amino acid sequence of two proteins*", *Journal of Molecular Biology* 48 (3): 443-53). Examples of current programs performing global alignments using the Needleman-Wunsch algorithm are EMBOSS Needle and EMBOSS Stretcher programs, which are both available at http://www.ebi.ac.uk/Tools/psa/.

EMBOSS Needle performs an optimal global sequence alignment using the Needleman-Wunsch alignment algorithm to find the optimum alignment (including gaps) of two sequences along their entire length.

EMBOSS Stretcher uses a modification of the Needleman-Wunsch algorithm that allows larger sequences to be globally aligned.

In one embodiment, the sequences are aligned by a global alignment program and the sequence identity is calculated by identifying the number of exact matches identified by the program divided by the "alignment length", where the alignment length is the length of the entire alignment including gaps and overhanging parts of the sequences.

In a further embodiment, the global alignment program uses the Needleman-Wunsch algorithm and the sequence identity is calculated by identifying the number of exact matches identified by the program divided by the "alignment length", where the alignment length is the length of the entire alignment including gaps and overhanging parts of the sequences.

In yet a further embodiment, the global alignment program is selected from the group consisting of EMBOSS Needle and EMBOSS stretcher and the sequence identity is calculated by identifying the number of exact matches identified by the program divided by the "alignment length", where the alignment length is the length of the entire alignment including gaps and overhanging parts of the sequences.

Once the software has produced an alignment, it is possible to calculate % similarity and % sequence identity. The software typically does this as part of the sequence comparison and generates a numerical result.

In one embodiment, it is preferred to use the ClustalW software for performing sequence alignments. Preferably, alignment with ClustalW is performed with the following parameters for pairwise alignment:

| | |
|---|---|
| Substitution matrix: | Gonnet 250 |
| Gap open penalty: | 20 |
| Gap extension penalty: | 0.2 |
| Gap end penalty: | None |

ClustalW2 is for example made available on the internet by the European Bioinformatics Institute at the EMBL-EBI webpage www.ebi.ac.uk under tools—sequence analysis—ClustalW2. Currently, the exact address of the ClustalW2 tool is www.ebi.ac.uk/Tools/clustalw2.

In another embodiment, it is preferred to use the program Align X in Vector NTI (Invitrogen) for performing sequence alignments. In one embodiment, Exp10 has been may be used with default settings:

Gap opening penalty: 10

Gap extension penalty: 0.05

Gap separation penalty range: 8

In a another embodiment, the alignment of one amino acid sequence with, or to, another amino acid sequence is determined by the use of the score matrix: blosum62mt2 and the VectorNTI Pair wise alignment settings

| | | |
|---|---|---|
| Settings | K-tuple | 1 |
| | Number of best diagonals | 5 |
| | Window size | 5 |
| | Gap Penalty | 3 |
| | Gap opening Penalty | 10 |
| | Gap extension Penalty | 0.1 |

In one embodiment, the percentage of identity of one amino acid sequence with, or to, another amino acid sequence is determined by the use of Blast with a word size of 3 and with BLOSUM 62 as the substitution matrix.

Polypeptides

In one aspect, the invention disclosed herein employs a polypeptide having a ratio of transgalactosylating activity: β-galactosidase activity of at least 0.5, at least 1, at least 2, at least 2.5, at least 3, at least 4, at least 5, at least 6, at least 7, at least 8, at least 9, at least 10, at least 11, or at least 12 at or above a concentration of 3% w/w initial lactose concentration.

In one aspect, the invention disclosed herein employs a polypeptide, wherein the glycoside hydrolase catalytic core has an amino acid sequence of SEQ ID NO:7.

In one aspect, the invention disclosed herein employs a polypeptide containing a Glyco_hydro2N (PF02837), a Glyco_hydro (PF00703) and/or a Glyco_hydro 2C (PF02836) domains.

In one aspect, disclosed herein is a polypeptide containing the Bacterial Ig-like domain (group 4) (PF07532).

In one aspect, disclosed herein is a polypeptide having transgalactosylating activity selected from the group consisting of:

a. a polypeptide comprising an amino acid sequence having at least 90% sequence identity with SEQ ID NO: 1, wherein said polypeptide consists of at most 980 amino acid residues,
b. a polypeptide comprising an amino acid sequence having at least 97% sequence identity with SEQ ID NO: 2, wherein said polypeptide consists of at most 975 amino acid residues,
c. a polypeptide comprising an amino acid sequence having at least 96.5% sequence identity with SEQ ID NO: 3, wherein said polypeptide consists of at most 1300 amino acid residues,
d. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4 or 5; or ii) the complementary strand of i),
e. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and
f. a polypeptide comprising a deletion, insertion and/or conservative substitution of one or more amino acid residues of SEQ ID NO: 1, 2, 3, 4 or 5.

In another aspect, the invention disclosed herein employs a polypeptide having transgalactosylating activity selected from the group consisting of:

a. a polypeptide comprising an amino acid sequence having at least 96.5% sequence identity with SEQ ID NO: 3, wherein said polypeptide consists of at most 1300 amino acid residues,
b. a polypeptide comprising an amino acid sequence having at least 90% sequence identity with SEQ ID NO: 1, wherein said polypeptide consists of at most 980 amino acid residues,
c. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4, or 5; or ii) the complementary strand of i),
d. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and
e. a polypeptide comprising a deletion, insertion and/or conservative substitution of one or more amino acid residues of SEQ ID NO: 1, 2, 3, 4 or 5.
f.

In one aspect, of the invention disclosed herein employs a polypeptide, wherein the amino acid sequence has at least 68%, 70%, 72%, 74%, 76%, 78%, 80%%, 85%, 90%, 91%, 92%, 93%, 94%, 95%, 96%, 97%, 98%, or 99%, sequence identity to the mature amino acid sequence of SEQ ID NO: 1, 2, 3, 4 or 5.

In one aspect, of the invention disclosed herein employs a polypeptide having 90% sequence identity to the mature amino acid sequence of SEQ ID NO:1.

In one aspect, of the invention disclosed herein employs a polypeptide having 90% sequence identity to the mature amino acid sequence of SEQ ID NO:2.

In one aspect, of the invention disclosed herein employs a polypeptide having 96.5% sequence identity to the mature amino acid sequence of SEQ ID NO:3.

In one aspect, of the invention disclosed herein employs a polypeptide having 96.5% sequence identity to the mature amino acid sequence of SEQ ID NO:4.

In one aspect, of the invention disclosed herein employs a polypeptide having 96.5% sequence identity to the mature amino acid sequence of SEQ ID NO:5.

In one aspect, of the invention disclosed herein employs a polypeptide comprising or consisting of the amino acid sequence of SEQ ID NO:1, 2, 3, 4 or 5.

In one aspect, of the invention disclosed herein employs a polypeptide, which is derived from *Bifidobacterium bifidum.*

In one aspect, of the invention disclosed herein employs a polypeptide having a pH optimum of 6.5-7.5.

In one aspect, of the invention disclosed herein employs a polypeptide having a temperature optimum of 30-60 such as 42-60 degree Celsius.

Polypeptides having activity on carbohydrates can be classified using either the IUBMB system of classification based on their substrate specificity or on the CaZy assignment into one of the current 125 glycoside hydrolase family. In the CaZy database the assignment is based on both sequence and structural information combined with knowledge of stereochemistry of the substrates and products.

Disclosed herein is the use of polypeptides which when being an expression product in a suitable host strain (e.g., *Bacillus subtilis*) comprising a nucleic acid sequence which encodes said polypeptide, is the only polypeptide expression product of said nucleic acid sequence that exhibits transgalactosylating activity. This may be evaluated by using the following techniques know to a person skilled in the art. The samples to be evaluated are subjected to SDS-PAGE and visualized using a dye appropriate for protein quantification, such as for example the Bio-Rad Criterion system. The gel is then scanned using appropriate densiometic scanner such as for example the Bio-Rad Criterion system and the resulting picture is ensured to be in the dynamic range. The bands corresponding to any variant/fragment derived from SEQ ID NO: 8 are quantified and the percentage of the polypeptides are calculated as: Percentage of polypeptide in question=polypeptide in question/(sum of all polypeptides exhibiting transgalactosylating activity)*100. The total number of polypeptides variants/fragments derived from SEQ ID NO:8 in the composition can be determined by detecting fragment derived from SEQ ID NO:8 by western blotting using a polyclonal antibody by methods know to a person skilled in the art.

The polypeptide disclosed herein comprises at least two separate functional domains contained within the enzyme. Firstly, the polypeptide should contain a glycoside hydrolase catalytic core as described in the following. The catalytic core should belong to the GH-A clan of related glycoside hydrolase families. The GH-A clan is characterized by cleaving glycosidic bonds via a retaining mechanism and possesses a catalytic domain which is based on a TIM barrel fold (Wierenga, 2001, FEBS Letters, 492(3), p 193-8). The catalytic domain contains two glutamic acid residues which act as proton donor and nucleophile, emanating from strands 4 and 7 of the barrel domain (Jenkins, 1995, FEBS Letters, 362(3), p 281-5). The overall structure of the TIM barrel is a 03/a) 8 fold consisting of 8 beta strands and 8 alpha-helices. In one aspect, the glycoside hydrolase catalytic core disclosed herein belong to either of the glycoside hydrolase families GH-2, and -35 which are all TIM-barrel enzymes belonging to the GH-A clan. In a further aspect, the glycoside hydrolase catalytic core belong to family GH-2 or GH-35. In a further aspect, the glycoside hydrolase catalytic core belong to family GH-2. A common denominator is that these enzymes are so called retaining enzymes, so that the stereochemistry of the substrate is conserved in the product (Henrissat, 1997, Curr Opin Struct Biol, 7(5), 637-44).

In one aspect, the polypeptides disclosed herein have activity on carbohydrates bonds which has the β(1→4) conformation. This effectively put the enzymes into the IUBMB EC 3.2.1.23 class of β-galactosidases. This activity may be, but is not confined to, determined by utilizing synthetic substrates such as para-nitrophenol-β-D-galactopyranoside (PNPG), ortho-nitrophenol-β-D-galactopyranoside (ONPG) or β-D-galactopyranoside with chromogenic aglycons (XGal). As an alternative way of determining whether an enzyme belong to the EC 3.2.1.23 class of β-galactosidases is to incubate with a substrate such as lactose and measure the release of glucose by a method such as enzymatic determination, HPLC, TLC or other methods known to persons skilled in the art.

In order to predict functional entities of polypeptides several available public repositories can be applied such as for example Pfam (Nucl. Acids Res. (2010) 38 (suppl 1): D211-D222. doi: 10.1093/nar/gkp985) and Interpro (Nucl. Acids Res. (2009) 37 (suppl 1): D211-D215. doi: 10.1093/nar/gkn785). It should be specified that when performing such analysis the analysis should be performed on the full length sequence of the polypeptide available from public repository databases.

In a further aspect, a polypeptide containing one or more Pfam domains selected from: Glyco_hydro2N (PF02837), Glyco_hydro (PF00703), Glyco_hydro 2C (PF02836) and Bacterial Ig-like domain (group 4) (PF07532), is provided. In yet a further aspect, a polypeptide containing the Pfam domains Glyco_hydro2N (PF02837), Glyco_hydro (PF00703), Glyco_hydro 2C (PF02836) and Bacterial Ig-like domain (group 4) (PF07532), is provided. In yet a further aspect, a polypeptide containing the Glyco_hydro2N (PF02837), Glyco_hydro (PF00703), and Glyco_hydro 2C (PF02836) domains which constitutes the catalytic domain of the polypeptide, is used.

In a further aspect, the polypeptide is derived from *Bifidobacterium bifidum*.

In a further aspect, a polypeptide as disclosed herein and having a ratio of transgalactosylating activity:β-galactosidase activity of at least 1, at least 2.5, at least 3, at least 4, at least 5, at least 6, at least 7, at least 8, at least 9, at least 10, at least 11, or at least 12 as measured at a concentration of 100 ppm in a milk-based assay at 37° C. and 5 w/w % lactose after 15, 30 or 180 such as 180 minutes reaction, is used.

In one aspect, the herein disclosed polypeptide(s) has a transgalactosylating activity such that more than 20%, more than 30%, more than 40%, up to 50% of the initial lactose is transgalactosylated as measured at a concentration of 100 ppm in a milk-based assay at 37° C. and 5 w/w % lactose after 15, 30 or 180 such as 180 minutes of reaction. In a preferred embodiment of the invention the afore-mentioned transgalactosylating activity is retained in the spray-dried composition of the invention. In one embodiment the transgalactosylating activity is retained in the spray-dried composition through the storage period of the spray-dried composition. This storage period may be at least 1, at least 2, at least 3, at least 4, at least 6, at least 7, at least 8, at least 9, at least 10, at least 11, at least 12, at least 18, or at least 24 months.

In a further aspect, the herein disclosed polypeptide(s) has a β-galactosidase activity such that less than 80%, less than 70%, less than 60%, less than 50%, less than 40%, less than 30%, less than 20% of the lactose has been hydrolysed as measured at a concentration of 100 ppm in a milk-based assay at 37° C. and 5 w/w % lactose after 15, 30 or 180 such as 180 minutes of reaction. In a preferred embodiment of the invention the afore-mentioned β-galactosidase activity is retained in the spray-dried composition of the invention. In one embodiment the 3-galactosidase activity is retained in the spray-dried composition through the storage period of the spray-dried composition. This storage period may be at least 1, at least 2, at least 3, at least 4, at least 6, at least 7, at least 8, at least 9, at least 10, at least 11, at least 12, at least 18, or at least 24 months.

In one aspect, the β-galactosidase activity and/or the transgalactosylating activity are measured at a concentration of 100 ppm corresponding to 2.13 LAU as specified in method 4. In general terms the units of activity of the enzyme may be measured according to the assay disclosed in WO 2003/186286 as Method 4 and reproduced herein as method 4.

In a further aspect, the herein disclosed polypeptide(s) has one or more of the following characteristics:

a) a ratio of transgalactosylating activity:β-galactosidase activity of at least of at least 1, at least 2.5, at least 3, at least 4, at least 5, at least 6, at least 7, at least 8, at least 9, at least 10, at least 11, or at least 12 as measured at a concentration of 100 ppm in a milk-based assay at 37° C. and 5 w/w % lactose after 15, 30 or 180 such as 180 minutes reaction, and/or
b) has a transgalactosylating activity such that more than 20%, more than 30%, more than 40%, and up to 50% of the initial lactose has been transgalactosylated as measured at a concentration of 100 ppm in a milk-based assay at 37° C. and 5 w/w % lactose after 15, 30 or 180 such as 180 minutes of reaction.

In one aspect, a polypeptide comprising an amino acid sequence having at least 96.5% sequence identity with SEQ ID NO: 3, wherein said polypeptide consists of at most 1300 amino acid residues, is provided. In a further aspect, a polypeptide comprising an amino acid sequence having at least 90% sequence identity with SEQ ID NO: 1 such as wherein said sequence identity is at least 95%, such as, e.g. at least 96%, at least 97%, at least 98%, at least 99% or at least 100% sequence identity, and wherein said polypeptide consists of at most 980 amino acid residues, is provided. In a further aspect, a polypeptide comprising an amino acid sequence having at least 90% sequence identity with SEQ ID NO: 1, wherein said polypeptide consists of at most 980 amino acid residues, is provided. In yet a further aspect, a polypeptide wherein said polypeptide has at least 90% sequence identity with SEQ ID NO: 1, such as wherein said polypeptide has at least 90%, such as, e.g. at least 91%, at least 92%, at least 93%, at least 94%, at least 95%, at least 96%, at least 97%, at least 98%, or at least 99% sequence identity with SEQ ID NO: 1 is provided. In another aspect, a polypeptide having at least 96.5% sequence identity to SEQ ID NO: 2 such as wherein said polypeptide has at least 97%, such as, e.g. at least 98% or at least 99% sequence identity with SEQ ID NO: 2. In one aspect, the polypeptides disclosed herein consist of at the most 975 amino acid residues, such as, e.g. at most 970 amino acid residues, such as at most 950 amino acid residues, such as at most 940 amino acid residues, at most 930 amino acid residues, at most 920 amino acid residues, at most 910 amino acid residues, at most 900 amino acid residues, at most 895 amino acid residues or at most 890 amino acid residues, is provided. In one aspect, a particular polypeptide consists of 887 or 965 amino acid residues, is provided. In one aspect, a polypeptide comprising an amino acid sequence having at least 97% sequence identity with SEQ ID NO: 2 such as wherein said sequence identity is at least 98%, such as, e.g. at least 99% or at least 100% sequence identity, wherein said polypeptide consists of at most 975 amino acid residues, such as, e.g. at most 970 or at least 965 amino acid residues, is provided. In one aspect, a polypeptide comprising an amino acid sequence having at least 97% sequence identity with SEQ ID NO: 2, wherein said polypeptide consists of at most 975 amino acid residues, is used.

In a further preferred aspect, a polypeptide which comprises SEQ ID NO:1, 2, 3, 4 or 5, is provided. In yet a preferred aspect, a polypeptide consisting of the amino acid sequence of SEQ ID NO: 1, 2, 3, 4, or 5, especially a polypeptide consisting of the amino acid sequence of SEQ ID NO: 1 or 2, is used.

In a further aspect, a polypeptide comprising an amino acid sequence having at least 96.5% sequence identity with SEQ ID NO: 3 such as wherein said sequence identity is at least 97%, such as, e.g. at least 98%, at least 99% or at least 100% sequence identity, wherein said polypeptide consists of at most 1300 amino acid residues, is used.

In a further aspect, a polypeptide wherein said polypeptide has at least 98.5%, such as at least 99% or at least 99.5% sequence identity with SEQ ID NO: 5, is provided. In one aspect, such a polypeptide consists of at most 1290 amino acid residues, such as, e.g. at most 1280, at most 1270, at most 1260, at most 1250, at most 1240, at most 1230, at most 1220 or at most 1215 amino acid residues, is provided. In a preferred aspect, a polypeptide which consists of 1211 amino acid residues, is used.

In a further aspect, a polypeptide wherein said polypeptide has at least 96% such as at least at least 97%, such as, e.g., at least 98% or at least 99% sequence identity with SEQ ID NO: 4, is provided. In one aspect, a polypeptide which consists of at most 1210 amino acid residues, such as, e.g. at most 1200, at most 1190, at most 1180, at most 1170, at most 1160, at most 1150 or at most 1145 amino acid residues, such as 1142 amino acid residues, is used.

In a further aspect, a polypeptide wherein said polypeptide has at least 96.5% such as at least 97%, such as, e.g., at least 98% or at least 99% sequence identity with SEQ ID NO: 3, is provided. In one aspect, a polypeptide which consists of at most 1130 amino acid residues, such as, e.g. at the most 1120, at the most 1110, at the most 1100, at the most 1090, at the most 1080, at the most 1070, at the most 1060, at the most 1050, at the most 1055 or at the most 1040 amino acid residues, is provided. In a preferred aspect, a polypeptide which consists of 1038 amino acid residues, is used.

In a further aspect, the polypeptides disclosed herein has a ratio of transgalactosylation activity above 100% such as above 150%, 175% or 200%.

Proteins are generally comprised of one or more functional regions, commonly termed domains. The presence of different domains in varying combinations in different proteins gives rise to the diverse repertoire of proteins found in nature. One way of describing the domains are by the help of the Pfam database which is a large collection of protein domain families as described in "*The Pfam protein families database*": R. D. Finn, J. Mistry, J. Tate, P. Coggill, A. Heger, J. E. Pollington, O. L. Gavin, P. Gunesekaran, G. Ceric, K. Forslund, L. Holm, E. L. Sonnhammer, S. R. Eddy, A. Bateman Nucleic Acids Research (2010) Database Issue 38:D211-222. Each family is represented by multiple sequence alignments and hidden Markov models (HMMs). The herein provided polypeptide(s) preferably contain one or more of the Pfam domains Glyco_hydro2N (PF02837), Glyco_hydro (PF00703), Glyco_hydro 2C (PF02836) and Bacterial Ig-like domain (group 4) (PF07532). In one aspect, the herein provided polypeptide(s) contains Glyco_hydro2N (PF02837), Glyco_hydro (PF00703), Glyco_hydro 2C (PF02836) and Bacterial Ig-like domain (group 4) (PF07532).

In one aspect, the polypeptides used herein have useful transgalactosylating activity over a range of pH of 4-9, such as 5-8, such as 5.5-7.5, such as 6.5-7.5.

The present invention encompasses the use of polypeptides having a certain degree of sequence identity or sequence homology with amino acid sequence(s) defined herein or with a polypeptide having the specific properties defined herein. The present invention encompasses, in particular, the use of peptides having a degree of sequence identity with any one of SEQ ID NO: 1, 2, 3, 4 or 5, defined below, or homologues thereof.

The homologous amino acid sequence and/or nucleotide sequence should provide and/or encode a polypeptide which retains the functional transgalactosylating activity and/or enhances the transgalactosylating activity compared to a polypeptide of SEQ ID NO: 1, 2, 3, 4 or 5.

In the present context, a homologous sequence is taken to include an amino acid sequence which may be at least 66%, 70%, 75%, 78%, at least 80%, at least 85%, at least 90%, at least 95%, at least 96%, at least 97%, at least 98% or at least 99%, identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

Thus, the present invention also encompasses the use of variants, homologues and derivatives of any amino acid sequence of a protein or polypeptide as defined herein, particularly those of SEQ ID NO: 1, 2, 3, 4 or 5 as defined below.

The sequences, particularly those of variants, homologues and derivatives of SEQ ID NO: 1, 2, 3, 4 or 5 defined below, may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

The present invention also encompasses conservative substitution (substitution and replacement are both used herein to mean the interchange of an existing amino acid residue, with an alternative residue) that may occur i.e. like-for-like substitution such as basic for basic, acidic for acidic, polar for polar etc. Non-conservative substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Conservative substitutions that may be made are, for example within the groups of basic amino acids (Arginine, Lysine and Histidine), acidic amino acids (glutamic acid and aspartic acid), aliphatic amino acids (Alanine, Valine, Leucine, Isoleucine), polar amino acids (Glutamine, Asparagine, Serine, Threonine), aromatic amino acids (Phenylalanine, Tryptophan and Tyrosine), hydroxyl amino acids (Serine, Threonine), large amino acids (Phenylalanine and Tryptophan) and small amino acids (Glycine, Alanine).

In one aspect, the polypeptide sequence used in the present invention is in a purified form.

In one aspect, the polypeptide or protein for use in the present invention is in an isolated form.

In one aspect, the polypeptide of the present invention is recombinantly produced.

The variant polypeptides include a polypeptide having a certain percent, e.g., at least 90%, 91%, 92%, 93%, 94%, 95%, 96%, 97%, 98%, or 99%, of sequence identity with SEQ ID NO: 1 or 2.

The variant polypeptides include a polypeptide having a certain percent, e.g., at least 96%, 97%, 98%, or 99%, of sequence identity with SEQ ID NO: 3, 4 or 5.

In one aspect, the polypeptides employed herein comprises an amino acid sequence having at least 90%, 91%, 92%, 93%, 94%, 95%, 96%, 97%, 98%, or 99% sequence identity to the amino acid sequence of the mature polypeptide encoded by the nucleotide sequence encoding the transgalactosylase contained in *Bifidobacterium bifidum* DSM20215 shown herein as SEQ ID NO: 22. All considerations and limitations relating to sequence identities and functionality discussed in terms of the SEQ ID NO: 1, 2, 3, 4 or 5 apply mutatis mutandis to sequence identities and functionality of these polypeptides and nucleotides.

In one aspect, the subject amino acid sequence is SEQ ID NO: 1, 2, 3, 4 or 5, and the subject nucleotide sequence preferably is SEQ ID NO: 9, 10, 11, 12 or 13.

In one aspect, the polypeptide is a fragment having one or more (several) amino acids deleted from the amino and/or carboxyl terminus of the polypeptide of SEQ ID NO: 1, 2, 3, 4 or 5; wherein the fragment has transgalactosylating activity.

In one aspect, a fragment contains at least 500, 550, 600, 650, 700, 750, 800, 850, 900, 950, or 1000 amino acid residues.

In a further aspect, the length of the polypeptide variant is 500 to 1300 amino acid residues. In a further aspect, the length of the polypeptide variant is 600 to 1300 amino acids. In a further aspect, the length of the polypeptide variant is 700 to 1300 amino acids. In a further aspect, the length of the polypeptide variant is 800 to 1300 amino acids. In a further aspect, the length of the polypeptide variant is 800 to 1300 amino acids.

Polypeptide Variants of SEQ ID NO: 1, 2, 3, 4 or 5

In one aspect, a variant of SEQ ID NO: 1, 2, 3, 4 or 5 having a substitution at one or more positions which effects an altered property such as improved transgalactosylation, relative to SEQ ID NO: 1, 2, 3, 4 or 5, is used. Such variant polypeptides are also referred to in this document for convenience as "variant polypeptide", "polypeptide variant" or "variant". In one aspect, the polypeptides as defined herein have an improved transgalactosylating activity as compared to the polypeptide of SEQ ID NO: 1, 2, 3, 4 or 5. In another aspect, the polypeptides as defined herein have an improved reaction velocity as compared to the polypeptide of SEQ ID NO: 1, 2, 3, 4 or 5.

The polypeptides and the variant polypeptides used herein comprise transgalactosylation activity.

In one aspect, the ratio of transgalactosylating activity:β-galactosidase activity is at least 0.5, such as at least 1, such as at least 1.5, or such as at least 2 after 30 min. reaction such as above a concentration of 3% w/w initial lactose concentration.

In one aspect, the ratio of transgalactosylating activity:β-galactosidase activity is at least 2.5, such as at least 3, such as at least 4, such as at least 5, such as at least 6, such as at least 7, such as at least 8, such as at least 9, such as at least 10, such as at least 11, or such as at least 12 after 30 min. reaction such as above a concentration of 3% w/w initial lactose concentration.

In one aspect, the polypeptides and the variants as defined herein are derivable from microbial sources, in particular from a filamentous fungus or yeast, or from a bacterium. The enzyme may, e.g., be derived from a strain of *Agaricus*, e.g. *A. bisporus; Ascovaginospora; Aspergillus*, e.g. *A. niger, A. awamori, A. foetidus, A. japonicus, A. olyzae; Candida; Chaetomium; Chaetotomastia; Dictyostelium*, e.g. *D. discoideum; Kluveromyces*, e.g. *K. fragilis, K. lactis; Mucor*, e.g. *M. javanicus, M. mucedo, M. subtilissimus; Neurospora*, e.g. *N. crassa; Rhizomucor*, e.g. *R. pusillus; Rhizopus*, e.g. *R. arrhizus, R. japonicus, R. stolonifer; Sclerotinia*, e.g. *S. libertiana; Torula; Torulopsis; Trichophyton*, e.g. *T. rubrum; Whetzelinia*, e.g. *W. sclerotiorum; Bacillus*, e.g. *B. coagulans, B. circulans, B. megaterium, B. novalis, B. subtilis, B. pumilus, B. stearothermophilus, B. thuringiensis; Bifidobacterium*, e.g. *B. longum, B. bifidum, B. animalis; Chryseobacterium; Citrobacter*, e.g. *C. freundii; Clostridium*, e.g. *C. perfringens; Diplodia*, e.g. *D. gossypina; Enterobacter*, e.g. *E. aerogenes, E. cloacae Edwardsiella, E. tarda; Erwinia*, e.g. *E. herbicola; Escherichia*, e.g. *E. coli; Klebsiella*, e.g. *K. pneumoniae; Miriococcum; Myrothesium; Mucor; Neurospora*, e.g. *N. crassa; Proteus*, e.g. *P. vulgaris; Providencia*, e.g. *P. stuartii; Pycnoporus*, e.g. *Pycnoporus cinnabarinus, Pycnoporus sanguineus; Ruminococcus*, e.g. *R. torques; Salmonella*, e.g. *S. typhimurium; Serratia*, e.g. *S. liquefasciens, S. marcescens; Shigella*, e.g. *S. flexneri; Streptomyces*, e.g. *S. antibioticus, S. castaneoglobisporus, S. violeceoruber; Trametes; Trichoderma*, e.g., *T. reesei, T. viride; Yersinia*, e.g. *Y. enterocolitica.*

An isolated and/or purified polypeptide comprising a polypeptide or a variant polypeptide as defined herein is provided. In one embodiment, the variant polypeptide is a mature form of the polypeptide (SEQ ID NO: 1, 2, 3, 4 or 5). In one aspect, the variants include a C-terminal domain.

In one aspect, a variant polypeptide as defined herein includes variants wherein between one and about 25 amino acid residues have been added or deleted with respect to SEQ ID NO: 1, 2, 3, 4 or 5. In one aspect, a variant polypeptide as defined herein includes variants wherein between one and 25 amino acid residues have been substituted, added or deleted with respect to SEQ ID NO: 1, 2, 3, 4 or 5. In one aspect, the variant has the amino acid sequence of SEQ ID NO: 1, 2, 3, 4 or 5, wherein any number between one and about 25 amino acids have been substituted. In a further aspect, the variant has the amino acid sequence of SEQ ID NO: 1, 2, 3, 4 or 5, wherein any number between three and twelve amino acids has been substituted. In a further aspect, the variant has the amino acid sequence of SEQ ID NO: 1, 2, 3, 4 or 5, wherein any number between five and nine amino acids has been substituted.

In one aspect, at least two, in another aspect at least three, and yet in another aspect at least five amino acids of SEQ ID NO: 1, 2, 3, 4 or 5 have been substituted.

In one aspect, the herein disclosed polypeptide(s) has the sequence of 1, 2, 3, 4 or 5.

In one aspect, the herein disclosed polypeptide(s) has the sequence of SEQ ID NO: 1, 2, 3, 4 or 5, wherein the 10, such as 9, such as 8, such as 7, such as 6, such 5, such as 4, such as 3, such as 2, such as 1 amino acid in the N-terminal end are substituted and/or deleted.

Enzymes and enzyme variants thereof can be characterized by their nucleic acid and primary polypeptide sequences, by three dimensional structural modelling, and/or by their specific activity. Additional characteristics of the polypeptide or polypeptide variants as defined herein include stability, pH range, oxidation stability, and thermostability, for example. Levels of expression and enzyme activity can be assessed using standard assays known to the artisan skilled in this field. In another aspect, variants demonstrate improved performance characteristics relative to the polypeptide with SEQ ID NO: 1, 2, 3, 4 or 5, such as improved stability at high temperatures, e.g., 65-85° C.

A polypeptide variant is provided as defined herein with an amino acid sequence having at least about 66%, 68%, 70%, 72%, 74%, 78%, 80%, 85%, 90%, 91%, 92%, 93%, 94%, 95%, 96%, 97%, 98%, 99%, 100% identity with the polypeptide of SEQ ID NO: 1, 2, 3, 4 or 5.

Nucleotides

In one aspect, the present invention employs isolated polypeptides having transgalactosylating activity as stated above which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with i) the nucleic acid sequence comprised in SEQ ID NO: 9, 10, 11, 12 or 13 encoding the mature polypeptide of SEQ ID NO: 1, 2, 3, 4 or 5; ii) the cDNA sequence of i) or iii) the complementary strand of i) or ii), (J. Sambrook, E. F. Fritsch, and T. Maniatis, 1989, *Molecular Cloning, A Laboratory Manual,* 2d edition, Cold Spring Harbor, New York). A subsequence of SEQ ID NO: 9, 10, 11, 12 or 13 contains at least 100 contiguous nucleotides or preferably at least 200 contiguous nucleotides. Moreover, the subsequence may encode a polypeptide fragment which has lactase activity.

The nucleotide sequence of SEQ ID NO: 9, 10, 11, 12 or 13 or a subsequence thereof, as well as the amino acid sequence of SEQ ID NO: 1, 2, 3, 4 or 5 or a fragment thereof, may be used to design a nucleic acid probe to identify and clone DNA encoding polypeptides having transgalactosylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labelled for detecting the corresponding gene (for example, with 32 P, 3H, 35S, biotin, or avidin). Such probes are encompassed by the present invention.

A genomic DNA library prepared from such other organisms may, therefore, be screened for DNA which hybridizes with the probes described above and which encodes a polypeptide having lactase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 9, 10, 11, 12 or 13 or a subsequence thereof, the carrier material is used in a Southern blot.

For purposes of the present invention, hybridization indicates that the nucleotide sequence hybridizes to a labelled nucleic acid probe corresponding to the nucleotide sequence shown in SEQ ID NO: 9, 10, 11, 12 or 13, its complementary strand, or a subsequence thereof, under very low to very high stringency conditions. Molecules to which the nucleic acid probe hybridizes under these conditions can be detected using X-ray film.

The nucleic acid probe may be the mature polypeptide coding region of SEQ ID NO: 9, 10, 11, 12 or 13.

For long probes of at least 100 nucleotides in length, very low to very high stringency conditions are defined as prehybridization and hybridization at 42° C. in 5×SSPE, 0.3% SDS, 200 g/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

In a particular embodiment, the wash is conducted using 0.2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). In another particular embodiment, the wash is conducted using 0.1×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

$$\text{Effective } T_m = 81.5 + 16.6(\log M[\text{Na}^+]) + 0.41(\%G + C) - 0.72(\%\text{ formamide})$$

(See www.ndsu.nodak.edu/instruct/mcclean/plsc731/dna/dna6.htm)

The G+C content of SEQ ID NO: 10 is 42% and the G+C content of SEQ ID NO: 11 is 44%. For medium stringency, the formamide is 35% and the $Na^+$ concentration for 5×SSPE is 0.75 M.

Another relevant relationship is that a 1% mismatch of two DNAs lowers the $T_m$ by 1.4° C. To determine the degree of identity required for two DNAs to hybridize under medium stringency conditions at 42° C., the following formula is used:

$$\%\text{ Homology} = 100 - [(\text{Effective } T_m - \text{Hybridization Temperature})/1.4]$$

(See www.ndsu.nodak.edu/instruct/mcclean/plsc731/dna/dna6.htm)

The variant nucleic acids include a polynucleotide having a certain percent, e.g., 60%, 65%, 70%, 75%, 80%, 85%, 90%, 95%, or 99%, of sequence identity with the nucleic acid encoding SEQ ID NO: 1, 2, 3, 4 or 5. In one aspect, a nucleic acid capable of encoding a polypeptide as disclosed herein, is provided. In a further aspect, the herein disclosed nucleic acid has a nucleic acid sequence which is at least 60%, such as at least 65%, such as at least 70%, such as at least 75%, such as at least 80%, such as at least 85%, such as at least 90%, such as at least 95%, such as at least 99% identical SEQ ID NO: 9, 10, 11, 12 or 13.

In one aspect, a plasmid comprising a nucleic acid as described herein may be used.

In another aspect, an expression vector comprising a nucleic acid as described herein, or capable of expressing a polypeptide as described herein may be used.

A nucleic acid complementary to a nucleic acid encoding any of the polypeptide variants as defined herein set forth herein is provided. Additionally, a nucleic acid capable of hybridizing to the complement is provided. In another embodiment, the sequence for use in the methods and compositions described here is a synthetic sequence. It includes, but is not limited to, sequences made with optimal codon usage for expression in host organisms, such as yeast. The polypeptide variants as provided herein may be produced synthetically or through recombinant expression in a host cell, according to procedures well known in the art. In one aspect, the herein disclosed polypeptide(s) is recombinant polypeptide(s). The expressed polypeptide variant as defined herein optionally is isolated prior to use.

In another embodiment, the polypeptide variant as defined herein is purified following expression. Methods of genetic modification and recombinant production of polypeptide variants are described, for example, in U.S. Pat. Nos. 7,371,552, 7,166,453; 6,890,572; and 6,667,065; and U.S. Published Application Nos. 2007/0141693; 2007/0072270; 2007/0020731; 2007/0020727; 2006/0073583; 2006/0019347; 2006/0018997; 2006/0008890; 2006/0008888; and 2005/0137111. The relevant teachings of these disclosures, including polypeptide-encoding polynucleotide sequences, primers, vectors, selection methods, host cells, purification and reconstitution of expressed polypeptide variants, and characterization of polypeptide variants as defined herein, including useful buffers, pH ranges, $Ca^{2+}$ concentrations, substrate concentrations and enzyme concentrations for enzymatic assays, are herein incorporated by reference.

A nucleic acid sequence is provided encoding the protein of SEQ ID NO: 1, 2, 3, 4 or 5 or a nucleic acid sequence having at least about 66%, 68%, 70%, 72%, 74%, 78%, 80%, 85%, 90%, 95%, 96%, 97%, 98%, 99% or 100% sequence identity with a nucleic acid encoding the protein of SEQ ID NO: 1, 2, 3, 4 or 5. In one embodiment, the nucleic acid sequence has at least about 60%, 66%, 68%, 70%, 72%, 74%, 78%, 80%, 85%, 90%, 95%, 96%, 97%, 98% or 99% sequence identity to the nucleic acid of SEQ ID NO: 9, 10, 11, 12 or 13.

Vectors

In one aspect, the invention employs a vector comprising a polynucleotide. In one aspect, a bacterial cell comprises the vector. In some embodiments, a DNA construct comprising a nucleic acid encoding a variant is transferred to a host cell in an expression vector that comprises regulatory sequences operably linked to an encoding sequence. The vector may be any vector that can be integrated into a fungal host cell genome and replicated when introduced into the host cell. The FGSC Catalogue of Strains, University of Missouri, lists suitable vectors. Additional examples of suitable expression and/or integration vectors are provided in Sambrook et al., Molecular Cloning: a Laboratory Manual, 316 ed., Cold Spring Harbor Laboratory Press, Cold Spring Harbor, New York (2001); Bennett et al., More Gene Manipulations in Fungi, Academic Press, San Diego (1991), pp. 396-428; and U.S. Pat. No. 5,874,276. Exemplary vectors include pFB6, pBR322, PUC18, pUC100 and pENTR/D, pDON™201, pDONR™221, pENTR™, pGEM®3Z and pGEM®4Z. Exemplary for use in bacterial cells include pBR322 and pUC19, which permit replication in *E. coli*, and pE194, for example, which permits replication in *Bacillus*.

In some embodiments, a nucleic acid encoding a variant is operably linked to a suitable promoter, which allows transcription in the host cell. The promoter may be derived from genes encoding proteins either homologous or heterologous to the host cell. Suitable non-limiting examples of promoters include cbh1, cbh2, egl1, and egl2 promoters. In one embodiment, the promoter is one that is native to the host cell. For example, when *P. saccharophila* is the host, the promoter is a native *P. saccharophila* promoter. An "inducible promoter" is a promoter that is active under environmental or developmental regulation. In another embodiment, the promoter is one that is heterologous to the host cell.

In some embodiments, the coding sequence is operably linked to a DNA sequence encoding a signal sequence. In another aspect, a representative signal peptide is SEQ ID NO: 27. A representative signal peptide is SEQ ID NO: 9 which is the native signal sequence of the *Bacillus subtilis* aprE precursor. In other embodiments, the DNA encoding the signal sequence is replaced with a nucleotide sequence encoding a signal sequence from other extra-cellular *Bacillus subtilis* pre-cursors. In one embodiment, the polynucleotide that encodes the signal sequence is immediately upstream and in-frame of the polynucleotide that encodes the polypeptide. The signal sequence may be selected from the same species as the host cell. In additional embodiments, a signal sequence and a promoter sequence comprising a DNA construct or vector to be introduced into a fungal host cell are derived from the same source. In some embodiments, the expression vector also includes a termination sequence. In one embodiment, the termination sequence and the promoter sequence are derived from the same source. In another embodiment, the termination sequence is homologous to the host cell.

In some embodiments, an expression vector includes a selectable marker. Examples of suitable selectable markers include those that confer resistance to antimicrobial agents, e.g., hygromycin or phleomycin. Nutritional selective markers also are suitable and include amdS, argB, and pyr4. In one embodiment, the selective marker is the amdS gene, which encodes the enzyme acetamidase; it allows transformed cells to grow on acetamide as a nitrogen source.

The use of an *A. nidulans* amdS gene as a selective marker is described in Kelley et al., *EMBO J.* 4: 475-479 (1985) and Penttila et al., *Gene* 61: 155-164 (1987).

A suitable expression vector comprising a DNA construct with a polynucleotide encoding a variant may be any vector that is capable of replicating autonomously in a given host organism or integrating into the DNA of the host. In some embodiments, the expression vector is a plasmid. In some embodiments, two types of expression vectors for obtaining expression of genes are contemplated. The first expression vector comprises DNA sequences in which the promoter, coding region, and terminator all originate from the gene to be expressed. In some embodiments, gene truncation is obtained by deleting undesired DNA sequences to leave the domain to be expressed under control of its own transcriptional and translational regulatory sequences. The second type of expression vector is preassembled and contains sequences required for high-level transcription and a selectable marker. In some embodiments, the coding region for a gene or part thereof is inserted into this general-purpose expression vector, such that it is under the transcriptional control of the expression construct promoter and terminator sequences. In some embodiments, genes or part thereof are inserted downstream of the strong cbh1 promoter.

Expression Hosts/Host Cells

In a further aspect, a host cell comprising, preferably transformed with, a plasmid as described herein or an expression vector as described herein, is used.

In a further aspect, a cell capable of expressing a polypeptide as described herein, is used.

In one aspect, the host cell as described herein, or the cell as described herein is a bacterial, fungal or yeast cell.

In a further aspect, the host cell is selected from the group consisting of Ruminococcus, *Bifidobacterium, Lactococcus, Lactobacillus, Streptococcus, Leuconostoc, Escherichia, Bacillus, Streptomyces, Saccharomyces, Kluyveromyces, Candida, Torula, Torulopsis* and *Aspergillus.*

In a further aspect, the host cell is selected from the group consisting of Ruminococcus *hansenii, Bifidobacterium breve, Bifidobacterium longum, Bifidobacterium infantis, Bifidobacterium bifidum* and *Lactococcus lactis.*

In another embodiment, suitable host cells include a Gram positive bacterium selected from the group consisting of *Bacillus subtilis, B. licheniformis, B. lentus, B. brevis, B. stearothermophilus, B. alkalophilus, B. amyloliquefaciens, B. coagulans, B. circulans, B. lautus, B. thuringiensis, Streptomyces lividans*, or *S. murinus*; or a Gram negative bacterium, wherein said Gram negative bacterium is *Escherichia coli* or a *Pseudomonas* species. In one aspect, the host cell is a *B. subtilus* or *B. licheniformis*. In one embodiment, the host cell is *B. subtilis*, and the expressed protein is engineered to comprise a *B. subtilis* signal sequence, as set forth in further detail below. In one aspect, the host cell expresses the polynucleotide as set out in the claims.

In some embodiments, a host cell is genetically engineered to express a polypeptide variant as defined herein with an amino acid sequence having at least about 66%, 68%, 70%, 72%, 74%, 78%, 80%, 85%, 90%, 91%, 92%, 93%, 94%, 95%, 96%, 97%, 98%, 99%, 100% identity with the polypeptide of SEQ ID NO: 1, 2, 3, 4 or 5. In some embodiments, the polynucleotide encoding a polypeptide variant as defined herein will have a nucleic acid sequence encoding the protein of SEQ ID NO: 1, 2, 3, 4 or 5 or a nucleic acid sequence having at least about 66%, 68%, 70%, 72%, 74%, 78%, 80%, 85%, 90%, 95%, 96%, 97%, 98%, 99% or 100% sequence identity with a nucleic acid encoding the protein of SEQ ID NO: 1, 2, 3, 4 or 5. In one embodiment, the nucleic acid sequence has at least about 60%, 66%, 68%, 70%, 72%, 74%, 78%, 80%, 85%, 90%, 95%, 96%, 97%, 98% or 99% sequence identity to the nucleic acid of SEQ ID NO: 9, 10, 11, 12 or 13.

Methods for Producing Polypeptides

In a further aspect, a method of expressing a polypeptide as described herein comprises obtaining a host cell or a cell as described herein and expressing the polypeptide from the cell or host cell, and optionally purifying the polypeptide. Such a polypeptide may be used in the present invention.

An expression characteristic means an altered level of expression of the variant, when the variant is produced in a particular host cell. Expression generally relates to the amount of active variant that is recoverable from a fermentation broth using standard techniques known in this art over a given amount of time. Expression also can relate to the amount or rate of variant produced within the host cell or secreted by the host cell. Expression also can relate to the rate of translation of the mRNA encoding the variant polypeptide.

Transformation, Expression and Culture of Host Cells

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Ausubel et al. (1987), supra, chapter 9; Sambrook et al. (2001), supra; and Campbell et al., *Curr. Genet.* 16: 53-56 (1989). The expression of heterologous protein in *Trichoderma* is described, for example, in U.S. Pat. Nos. 6,022,725; 6,268,328; Harkki et al., *Enzyme Microb. Technol.* 13: 227-233 (1991); Harkki et al., *BioTechnol.* 7: 596-603 (1989); EP 244,234; and EP 215,594. In one embodiment, genetically stable transformants are constructed with vector systems whereby the nucleic acid encoding a variant is stably integrated into a host cell chromosome. Transformants are then purified by known techniques.

In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium, e.g., a medium that lacks acetamide, harvesting spores from this culture medium and determining the percentage of these spores that subsequently germinate and grow on selective medium containing acetamide. Other methods known in the art may be used to select transformants.

Identification of Activity

To evaluate the expression of a variant in a host cell, assays can measure the expressed protein, corresponding mRNA, or β-galactosidase activity. For example, suitable assays include Northern and Southern blotting, RT-PCR (reverse transcriptase polymerase chain reaction), and in situ hybridization, using an appropriately labeled hybridizing probe. Suitable assays also include measuring activity in a sample. Suitable assays of the activity of the variant include, but are not limited to, ONPG based assays or determining glucose in reaction mixtures such for example described in the methods and examples herein.

Methods for Purifying Herein Disclosed Polypeptides

In general, a variant produced in cell culture is secreted into the medium and may be purified or isolated, e.g., by removing unwanted components from the cell culture medium. In some cases, a variant may be recovered from a cell lysate. In such cases, the enzyme is purified from the cells in which it was produced using techniques routinely employed by those of skill in the art. Examples include, but are not limited to, affinity chromatography, ion-exchange chromatographic methods, including high resolution ion-exchange, hydrophobic interaction chromatography, two-phase partitioning, ethanol precipitation, reverse phase HPLC, chromatography on silica or on a cation-exchange resin, such as DEAE, chromatofocusing, SDS-PAGE, ammonium sulfate precipitation, and gel filtration using Sephadex G-75, for example. The herein disclosed polypeptide(s) is spray-dried.

Spray Drying

In general terms, spray drying is a process for producing powders from a liquid where a suspension or solution is fed to an atomizer and the droplets formed are mixed with a hot gas. Generally the polypeptide of the invention will be in solution. The solvent of the droplets thus evaporate, leaving dry particles. Conventional spray-drying techniques may be used in the processing of the present invention, such as those discussed in Spray-Drying Handbook, 4th Edition, K. Masters, (1985), which is incorporated herein by reference. A simple spray drier plant design has three process stages which characterise spray drying:

1) Feed atomization;
2) Droplet drying by mixing of drying gas and spray; and
3) Separation of drying gas and spray.

The method for the preparation of a spray-dried powder typically first comprises the dispersion of a carrier in water, and then the mixture of this dispersion. The mixture is then spray-dried to produce a powdered product.

Thus, particle drying according to the present invention is performed through a spray-drying process. In its most basic form, the process involves the following: transporting a liquid or suspension through an atomizing device into a drying chamber; mixing droplets of the atomized liquid or suspension with a stream of heated air; evaporating volatile components of the droplets in the stream of air leaving dried particles.

The atomizer may be of any suitable type. Non-limiting examples of atomizers include high speed rotating disk atomizers, pressure nozzle atomizers, pneumatic nozzle atomizers, and sonic nozzle atomizers.

The spray-dried powder of the invention can also be advantageously used as an intermediate product or starting product for a double-encapsulation method, i.e. as a solid product susceptible of being subjected to a further encapsulation such as an extrusion in a glassy matrix to provide a granular delivery system, or to a second spray drying operation in a distinct or similar matrix, and the invention also relates to that use of the composition.

The spray-drying apparatus used in the process of the invention can be any one of the various commercially available apparatuses. Examples of spray-drying apparatuses are the Anhydro Dryers (origin: Anhydro Corp. of Attleboro Falls, Mass.), the Niro Dryer (manufactured by Niro Atomizer Ltd., Copenhagen, Denmark), or a Leaflash apparatus (origin: CCM Sulzer). Preferably a spray-drier with a pressure nozzle is used.

The typical parameters of a spray-drying process are well known in the art and can be easily adjusted by a skilled person in the art.

The particles of the invention have typically a size comprised between 50 and 70 μm and a bulk density comprised between 0.4 and 0.6 g/cm3.

However, the granulometry and the bulk density of the resulting dry powders can be adjusted by inter a/ia selecting the nozzle (orifice size/diameter) and the atomization pressure so as to obtain the desired powder flowability.

The compositions of the invention may also contain optional ingredients in addition to the maltodextrin and/or sodium chloride.

The composition of the fluid going into the spray dryer may be formulated so that the atomized liquid, generally aqueous, composition formed in the initial stages of the spray-drying process includes at least one polypeptide, which is typically present in the liquid composition at a concentration greater than 0.01 or greater than 0.5 weight percent.

In a method aspect, the present invention provides a method for increasing the yield of a spray-drying process. The process provides a particle that includes a polypeptide at a concentration typically greater than 0.5 weight percent. The method includes the following steps: a) feeding an aqueous composition into a spray-drying apparatus, wherein the aqueous composition comprises a maltodextrin and/or sodium chloride and at least one polypeptide and, wherein the at least one polypeptide is present in the aqueous composition at a concentration typically of 20 to 80 g/L; and, b) spray-drying the composition. In the aqueous composition, the sodium chloride should preferably be present at a level so as to give microbial stability to the final spray-dried composition, therefore a range of 10-20% in the aqueous composition would be suitable, with a maximum of about 25%. The maltodextrin may be used in the aqueous composition in the range of 5-40%, with 10-30% being preferred. In one embodiment the maltodextrin is used at about 17%.

An enzyme-containing liquid or suspension may be used in the present invention and may be, for example, a fermentation broth or processed fermentation broth.

A fermentation broth includes microbial cells and/or related cell debris (i.e., biomass). Some or most of the biomass may be removed from the fermentation broth to modify properties of the broth for spray drying. Typically, at least 10 percent by weight to 20 percent by weight of the biomass is removed from the broth prior to spray drying. Oftentimes, at least 30 percent, 40 percent, 50 percent, or 60 percent of the biomass is removed, and in certain cases at least 70 percent, 80 percent, 90 percent, or 95 percent of the biomass is removed.

Biomass may be removed from the fermentation broth using a variety of techniques. Such techniques include filtration, centrifugation, flocculation and combinations thereof. Typically, the fermentation broth includes between 0 and 35 percent weight/weight dry matter. Oftentimes, the broth includes between 0 and 20 percent weight/weight dry matter or between 0 and 15 percent weight/weight dry matter. In certain cases, the fermentation broth includes between 5 percent and 15 percent weight/weight dry matter. Up to 90 percent weight/weight of the dry matter is biomass. Oftentimes, up to 75 percent, 50 percent or 25 percent weight/weight of the dry matter is biomass. In certain cases, up to 10 percent weight/25 weight of the dry matter is biomass.

The fermentation broth may be de-sludged through the removal of coarse particles or bodies. Such particles/bodies include straw, rubble, soy grits and other non-biomass insolubles that typically originate from nutrients added to the broth during fermentation. Removal is typically accomplished by one of the following methods: straining, filtration, sedimentation, centrifugation and/or decanting the broth.

Where a solution or suspension containing an enzyme is used in the present invention, the liquid medium is typically water. For instance, the enzyme-containing material may be enzyme concentrate obtained from fermentation filtrate processing. Processing methods used to concentrate the fermentation broth include, without limitation: ultra filtration to reduce water content and low molecular components; extraction of the enzyme from the fermentation filtrate into a second liquid; crystallization or precipitation of the enzyme followed by resuspension and, purification through column chromatography may be used, e.g. by pumping 5 the fermentation filtrate through a column comprising a resin.

Materials may be added to an enzyme-containing liquid to improve the properties of spray dried products obtained from the liquids. Non-limiting examples of such additives include: salts (e.g., alkali salts, earth metal salts, additional chloride salts, sulfate salts, nitrate salts, carbonate salts, where exemplary counterions are calcium, potassium, and sodium), inorganic minerals or clays (e.g., zeolites, kaolin, bentonite, talc's and/or silicates), carbohydrates (e.g., sucrose and/or starch), coloring pigments (e.g., titanium dioxide), biocides (e.g., Rodalon®, Proxel®), dispersants, anti-foaming agents, acid agents, alkaline agents, enzyme stabilizers (e.g., methionine, or thiosulphate), enzyme inhibitors (e.g., boric acid protease inhibitors), binders other enzymes and combinations thereof. Polymeric additives typically are either low MW 15 (<250,000 Daltons) materials, or are added as slurries where the additive is not in solution.

It is preferable that a process is provided in which the dust levels produced are at a minimum. We have found that advantageously a reduction in dust levels can be achieved through the use of potato starch in the process. Thus in one embodiment a potato starch is added to the enzyme-containing liquid to improve the size distribution of spray dried products obtained from the liquids. In such an embodiment, the composition prepared according to the spray-dried process may comprise 5-50% by weight of maltodextrin or sodium chloride, 25-95% of the potato starch and 20-45% by weight of the enzyme wherein in any one formulation the total amount of components (which may include additional components to those recited above) equals 100% by weight.

The enzyme-containing liquid may also be subjected to physical treatments prior to spray drying. Such physical treatments include, without limitation, heating and/or cooling and/or radiating the liquid, mixing the liquid, aerating the liquid, and ultra-sound treatment of the liquid. Enzyme-containing liquids used in the present invention typically include at least 1 mg of "active" enzyme, e.g. catalytically active protein of interest, per liter of liquid. Typically, the liquids include about 20 g/L to 80 g/L active polypeptide, which corresponds to about 500 to 2000 LAU/g active polypeptide.

Post Processing of Spray-Dried Particles

The spray-dried particles formed according to the present invention may be further processed using a variety of methods. Non-limiting examples of such methods include mixer granulation, prilling, extrusion, fluid bed processes, coating, and milling/grinding and screening. Mixer granulation involves mixing spray dried particles with water and an additional component. Additional components are typically binders, fibers, salts, water insoluble minerals, pigments, enzyme stabilizers or combinations thereof. Water is added in amounts sufficient to agglomerate solid components into granules of a suitable mean size. The water is subsequently removed using a suitable drying method. Binders used in a mixer granulation process for particles of the present invention are polymeric in nature. Exemplary binders include polyvinyl pyrrolidone, dextrins and cellulose derivatives (e.g., hydroxypropyl cellulose, methyl cellulose or carboxymethyl cellulose Glucidex 21D, available from Roquette Freres, France, is oftentimes a suitable binder. Fibers used in a mixer granulation process include pure and/or impure fibrous cellulose, such as sawdust, pure fibrous cellulose, and cotton. Filter aids based on fibrous cellulose can also be used. Examples of commercially available fibrous cellulose include Cepo™ and Arbocell™. Synthetic fibers as discussed in EP 304331 B1 may be used, including fibers made of polyethylene, polypropylene, polyester, especially nylon, polyvinylformate, poly(meth)acrylic compounds. Salts used in a mixer granulation process include water soluble and/or insoluble salts such as alkali and/or earth alkali salts of sulfate, chloride, carbonate and phosphate.

Water insoluble minerals used in a mixer granulation process include zeolites, clays like kaolin and bentonite, tales, and/or silicates. Pigments used in a mixer granulation process include titanium dioxide.

Enzyme stabilizers used in a mixer granulation process include alkaline or neutral materials (e.g., metal silicates, carbonates or bicarbonates), reducing agents (e.g., sulfite, thiosulfite, or thiosulfate), antioxidants (e.g., methionine, butylated hydroxytoluene, or butylated hydroxyanisol) and/or salts of first transition series metal ions. These agents may be used in conjunction with other protective agents of the same or different categories. A number of mixer granulation process are known in the art, including those discussed in the following documents: U.S. Pat. No. 4,106,991; EP 170360 B1; EP 304332 B1; EP 304331; WO 90/09440; and, WO 90/09428.

Prilling involves suspending dried particles in molten wax followed by spray cooling of the suspension. The process is discussed in Michael S. Showell (editor); Powdered detergents; Surfactant Science Series; 1998; vol. 71, page 140-142, Marcel Dekker; and, DK-PA 1999. A wax used in the pilling process has a melting point between 25 and 125° C. and is typically an organic compound or a salt of an organic compound. It oftentimes is either water soluble or water dispersible in a neutral or alkaline solution. Non-limiting examples of water soluble waxes are the polyethylene glycols (e.g., PEG 1000).

Extrusion involves adding moisture to particles, either alone or mixed with an additive as described for mixer granulation, to provide a paste. The paste is pressed into pellets or is extruded under pressure through a small opening; it is then cut into particles, which are dried. Extrusion processes are discussed in Michael S. Showell (editor); Powdered detergents; Surfactant Science Series; 1998; vol. 71, page 140-42, Marcel Dekker; and, U.S. Pat. No. 4,661,452.

Fluid bed processes involve fluidizing spray dried particles in a fluid bed. A solution containing a binder is atomized and brought into contact with the fluidized particles. This causes the particles to bind together, forming larger, stronger particles. Spray dried particles of the present invention may be coated with one or more coating layers. The coating may include materials such as binders, fibers, salts, water insoluble materials, pigments, enzyme stabilizers or combinations thereof as described above in the mixer granulation section.

The processes described above may be supplemented with milling/grinding and/or screening processes at any stage. It may, for example, be desirable to grind the spray dried particles prior to subsequent processing steps and to screen the final product to obtain the desired size fraction.

Compositions, Application and Use

Examples are given below of preferred uses of the polypeptides or polypeptide-containing compositions of the invention.

In one aspect, disclosed herein is a method for producing a food product by treating a substrate comprising lactose with a spray-dried composition as described herein.

In one aspect, disclosed herein is a method for producing a dairy product by treating a milk-based substrate comprising lactose with a spray-dried composition as described herein.

In one aspect, the substrate comprising lactose is further treated with a hydrolysing beta-galactosidase.

In one aspect, a composition preferably a food composition, more preferably a dairy product comprising a cell or a polypeptide as described herein, is provided.

Furthermore, disclosed herein is a composition comprising at least 5%, such as e.g. 10%, 15%, 20%, 25%, 30%, 35%, 40%, 45%, 50% w/w of one or more polypeptide(s) as disclosed herein based on the total amount of polypeptides in the composition having at least 70%, e.g. such as 72%, 74%, 74%, 78%, 80%, 82%, 84%, 86%, 88%, 90% sequence identity with SEQ ID NO: 22. This may be evaluated by using the following techniques know to a person skilled in the art. The samples to be evaluated are subjected to SDS-PAGE and visualized using a dye appropriate for protein quantification, such as for example the Bio-Rad Criterion system. The gel is then scanned using appropriate densiometic scanner such as for example the Bio-Rad Criterion system and the resulting picture is ensured to be in the dynamic range. The bands corresponding to any variant/fragment derived from SEQ ID NO: 8 are quantified and the percentage of the polypeptides are calculated as: Percentage of polypeptide in question=polypeptide in question/(sum of all polypeptides exhibiting transgalactosylating activity) *100. The total number of polypeptides variants/fragments derived from SEQ ID NO:8 in the composition can be determined by detecting fragment derived from SEQ ID NO:8 by western blotting using a polyclonal antibody by methods know to a person skilled in the art.

In one aspect, the composition according to the present invention comprises one or more polypeptide(s) selected from the group consisting of a polypeptide consisting of SEQ ID NO: 1, 2, 3, 4 and 5. In a further aspect, the composition comprises one or more polypeptide(s) selected from the group consisting of a polypeptide consisting of SEQ ID NO: 1, 2 and 3. In yet a further aspect, the composition comprises one or more polypeptide(s) selected from the group consisting of a polypeptide consisting of SEQ ID NO: 1 and 2.

In one aspect the invention provides an enzyme complex preparation comprising the enzyme complex according to the invention, an enzyme carrier in the form of maltodextrin and/or sodium chloride and optionally a stabilizer and/or a preservative.

In yet a further aspect of the invention, the composition does not include a polyol, such as glycerol, or water.

In a further aspect, the preparation/composition comprises a stabilizer. In one aspect, the stabilizer is selected from the group consisting of inorganic salts, sugars and combinations thereof. In one aspect, the stabilizer is an inorganic salt such as potassium chloride. In another aspect, the stabilizer is not a polyol such as glycerol, propylene glycol, or sorbitol. In yet another aspect, the sugar is a small-molecule carbohydrate, in particular any of several sweet-tasting ones such as glucose, galactose, fructose and saccharose.

In yet at further aspect, the preparation comprises a preservative. In one aspect, the preservative is methyl paraben, propyl paraben, benzoate, sorbate or other food approved preservatives or a mixture thereof.

Excipients which may be used in the preparation/composition include maltose, sucrose, glucose including glucose syrup or dried glucose syrup, pre-cooked starch, gelatinised starch, L-lactic, ascorbyl palmitate, tocopherols, lecithins, citric acid, citrates, phosphoric, phosphates, sodium alginate, carrageenan, locust bean gum, guar gum, xanthan gum, pectins, sodium carboxymethylcellulose, mono- and diglycerides, citric acid esters of mono- and diglycerides, sucrose esters, carbon dioxide, argon, helium, nitrogen, nitrous oxide, oxygen, hydrogen, and starch sodium octenylsuccinate.

In one aspect, a method for producing a dairy product by treating a milk-based substrate comprising lactose with a spray-dried composition as described herein is provided. In a further aspect, a method for producing a dairy product by treating a milk-based substrate comprising lactose with a polypeptide having a relative transgalactosylation activity above 60%, such as above 70%, such as above 75% after 15 min. reaction, is provided. In one aspect, the relative transgalactosylation activity is above 3 after 30 min. reaction. In a further aspect, the relative transgalactosylation activity is above 6 after 30 min. reaction. In yet a further aspect, the relative transgalactosylation activity is above 12 after 30 min. reaction. In one aspect, a method is provided, wherein the treatment with a polypeptide as described herein takes place at an optimal temperature for the activity of the enzyme. In a further aspect, the polypeptide is added to the milk-based substrate at a concentration of 0.01-1000 ppm. In yet a further aspect, the polypeptide is added to the milk-based substrate at a concentration of 0.1-100 ppm. In a further aspect, the polypeptide is added to the milk-based substrate at a concentration of 1-10 ppm. In one aspect, a method further comprising fermenting a substrate such as a dairy product with a microorganism, is provided. In a further aspect, the dairy product is yogurt. In a further aspect, the treatment with the polypeptide and the microorganism is performed essentially at the same time. In one aspect, the polypeptide and the microorganism are added to the milk-based substrate essentially at the same time.

In one aspect, a dairy product comprising a spray-dried composition as described herein, is provided. In one aspect, the polypeptide as defined herein is added in a concentration of 0.01-1000 ppm. In one aspect, a dairy product comprising an inactivated polypeptide as defined herein, is provided. In one aspect, a dairy product comprising GOS formed in situ by a polypeptide as defined herein, is provided. In one aspect, a dairy product comprising a cell as defined herein, is provided.

A dairy product as described herein may be, e.g., skim milk, low fat milk, whole milk, cream, UHT milk, milk having an extended shelf life, a fermented milk product, cheese, yoghurt, butter, dairy spread, butter milk, acidified milk drink, sour cream, whey based drink, ice cream, condensed milk, dulce de leche or a flavoured milk drink. A dairy product may be manufactured by any method known in the art.

A dairy product may additionally comprise non-milk components, e.g. vegetable components such as, e.g., vegetable oil, vegetable protein, and/or vegetable carbohydrates. Dairy products may also comprise further additives such as, e.g., enzymes, flavouring agents, microbial cultures such as probiotic cultures, salts, sweeteners, sugars, acids, fruit, fruit juices, or any other component known in the art as a component of, or additive to, a dairy product.

In one embodiment of the invention, one or more milk components and/or milk fractions account for at least 50% (weight/weight), such as at least 70%, e.g. at least 80%, preferably at least 90%, of the dairy product.

In one embodiment of the invention, one or more milk-based substrates having been treated with an enzyme as defined herein having transgalactosylating activity account for at least 50% (weight/weight), such as at least 70%, e.g. at least 80%, preferably at least 90%, of the dairy product.

In one embodiment of the invention, the dairy product is a dairy product which is not enriched by addition of pre-produced galacto-oligosaccharides.

In one embodiment of the invention, the polypeptide-treated milk-based substrate is not dried before being used as an ingredient in the dairy product.

In one embodiment of the invention, the dairy product is ice cream. In the present context, ice cream may be any kind of ice cream such as full fat ice cream, low fat ice cream, or ice cream based on yoghurt or other fermented milk products. Ice cream may be manufactured by any method known in the art.

In one embodiment of the invention, the dairy product is milk or condensed milk.

In one embodiment of the invention, the dairy product is UHT milk. UHT milk in the context of the present invention is milk which has been subjected to a sterilization procedure which is intended to kill all microorganisms, including the bacterial spores. UHT (ultra high temperature) treatment may be, e.g., heat treatment for 30 seconds at 130° C., or heat treatment for one second at 145° C.

In one preferred embodiment of the invention, the dairy product is ESL milk. ESL milk in the present context is milk which has an extended shelf life due to microfiltration and/or heat treatment and which is able to stay fresh for at least 15 days, preferably for at least 20 days, on the store shelf at 2-5° C.

In another preferred embodiment of the invention, the dairy product is a fermented dairy product, e.g., yoghurt.

The microorganisms used for most fermented milk products are selected from the group of bacteria generally referred to as lactic acid bacteria. As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of anaerobic bacteria, bifidobacteria, i.e. *Bifidobacterium* spp., which are frequently used as food cultures alone or in combination with lactic acid bacteria, are generally included in the group of lactic acid bacteria.

Lactic acid bacteria are normally supplied to the dairy industry either as frozen or freeze-dried cultures for bulk starter propagation or as so-called "Direct Vat Set" (DVS) cultures, intended for direct inoculation into a fermentation vessel or vat for the production of a fermented dairy product. Such cultures are in general referred to as "starter cultures" or "starters".

Commonly used starter culture strains of lactic acid bacteria are generally divided into mesophilic organisms having optimum growth temperatures at about 30° C. and thermophilic organisms having optimum growth temperatures in the range of about 40 to about 45° C. Typical organisms belonging to the mesophilic group include *Lactococcus lactis, Lactococcus lactis* subsp. *cremoris, Leuconostoc mesenteroides* subsp. *cremoris, Pseudoleuconostoc mesenteroides* subsp. *cremoris, Pediococcus pentosaceus, Lactococcus lactis* subsp. *lactis biovar. diacetylactis, Lactobacillus casei* subsp. *casei* and *Lactobacillus paracasei* subsp. *paracasei*. Thermophilic lactic acid bacterial species include as examples *Streptococcus thermophilus, Enterococcus faecium, Lactobacillus delbrueckii* subsp. *lactis, Lactobacillus helveticus, Lactobacillus delbrueckii* subsp. *bulgaricus* and *Lactobacillus acidophilus*. Also the anaerobic bacteria belonging to the genus *Bifidobacterium* including *Bifidobacterium bifidum, Bifidobacterium* anima/is and *Bifidobacterium longum* are commonly used as dairy starter cultures and are generally included in the group of lactic acid bacteria. Additionally, species of Propionibacteria are used as dairy starter cultures, in particular in the manufacture of cheese. Additionally, organisms belonging to the *Brevibacterium* genus are commonly used as food starter cultures.

Another group of microbial starter cultures are fungal cultures, including yeast cultures and cultures of filamentous fungi, which are particularly used in the manufacture of certain types of cheese and beverage. Examples of fungi include *Penicillium roqueforti, Penicillium candidum, Geotrichum candidum, Torula kefir, Saccharomyces kefir* and *Saccharomyces cerevisiae.*

In one embodiment of the present invention, the microorganism used for fermentation of the milk-based substrate is *Lactobacillus casei* or a mixture of *Streptococcus thermophilus* and *Lactobacillus delbrueckii* subsp. *bulgaricus.*

Fermentation processes to be used in a method of the present invention are well known and the person of skill in the art will know how to select suitable process conditions, such as temperature, oxygen, amount and characteristics of microorganism/s, additives such as e.g. carbohydrates, flavours, minerals, enzymes, and process time. Obviously, fermentation conditions are selected so as to support the achievement of the present invention.

As a result of fermentation, pH of the milk-based substrate will be lowered. The pH of a fermented dairy product of the invention may be, e.g., in the range 3.5-6, such as in the range 3.5-5, preferably in the range 3.8-4.8.

In one aspect, a method of using the spray-dried composition is provided to produce galacto-oligosaccharides, In one embodiment of the invention, the GOS is produced by incubating the spray-dried composition in a medium that comprises a lactose substrate. The incubation is carried out under conditions where GOS is produced.

In one aspect, the use of a herein disclosed spray-dried composition for producing a product selected from the group consisting of yoghurt, cheese, fermented milk product, dietary supplement and probiotic comestible product, is provided.

In one aspect, the spray-dried composition described herein may be used to prepare cheese products and in methods for making the cheese products. Cheese products may e.g. be selected from the group consisting of cream cheese, cottage cheese, and process cheese. By adding polypeptides the cheeses may contain significantly increased levels of galacto-oligosaccharides and reduced levels of lactose. In one aspect, the lactose levels in the final cheese product may be reduced by at least about 25 percent, preferably at least about 50 percent, and more preferably at least about 75 percent. The polypeptides may be used to reduce lactose in cheese products to less than about 1 gram per serving, an amount that can be tolerated by most lactose-intolerant individuals.

The cheese products provided herein are nutritionally-enhanced cheese products having increased soluble fiber content, reduced caloric content, excellent organoleptic properties, improved texture, and flavor. Further, the polypeptides described herein may reduce the glycemic index of the cheese products because GOS are more slowly absorbed than lactose or its hydrolysis products. Finally, the polypeptides may reduce the cost of production of cheese products, particularly cream cheese products, because GOS surprisingly provide improved texture to the cream cheese product, thus permitting reduced use of stabilizers, or by allowing for increased moisture content without syneresis.

In a further aspect, a composition comprising a spray-dried composition as described herein and a carbohydrate substrate, is provided. In a further aspect, the carbohydrate substrate is a disaccharide. In a further aspect, the disaccharide is for example lactulose, trehalose, rhamnose, maltose, sucrose, lactose or cellobiose. In yet a further aspect, the carbohydrate substrate is lactose. The composition is prepared such that oligosaccharides are produced. The polypeptide as described herein may be part of a product selected from the group consisting of yoghurt, cheese, fermented milk products, dietary supplements, and probiotic comestible products. In one aspect, a composition comprising a polypeptide as described herein and a stabilizer, is provided. Examples of stabilizers are a sugar or a sugar alcohol, lactic acid, boric acid, or a boric acid derivative (e.g., an aromatic borate ester). Preferably the stabilizer is not a polyol such as, e.g. glycerol or propylene glycol.

In one aspect, the use of a transgalactosylating polypeptide in a composition as disclosed herein, for producing galacto-oligosaccharides, is provided. In one aspect, the use of a spray-dried composition for producing galacto-oligosaccharides to be part of a product selected from the group consisting of yoghurt, cheese, fermented dairy products, dietary supplements and probiotic comestible products, is provided. In one aspect, the product is yoghurt, cheese, or fermented dairy products. In one aspect, the use of a spray-dried composition as disclosed herein, for producing galacto-oligosaccharides to enhance the growth of *Bifidobacterium*, is provided. In one aspect, the use of a spray-dried composition as disclosed herein or a cell as disclosed herein, for producing galacto-oligosaccharides to enhance the growth of *Bifidobacterium* in a mixed culture fermentation, is provided.

The treatment of milk products with enzymes that converts lactose into monosaccharides or GOS have several advantages. First the products can be consumed by people with lactose intolerance that would otherwise exhibit symptoms such as flatulence and diarrhea. Secondly, dairy products treated with lactase will have a higher sweetness than similar untreated products due to the higher perceived sweetness of glucose and galactose compared to lactose. This effect is particularly interesting for applications such as yoghurt and ice-cream where high sweetness of the end product is desired and this allows for a net reduction of carbohydrates in the consumed product. Thirdly, in ice-cream production a phenomenon termed sandiness is often seen, where the lactose molecules crystallizes due to the relative low solubility of the lactose. When lactose is converted into monosaccharides or GOS the mouth feeling of the ice-cream is much improved over the non-treated products. The presence of a sandy feeling due to lactose crystallization can be eliminated and the raw material costs can be decreased by replacement of skimmed milk powder by whey powder. The main effects of the enzymatic treatment were increased sweetness.

In one aspect, the spray-dried composition as disclosed herein may be used together with other enzymes such as proteases such as chymosin or rennin, lipases such as phospholipases, amylases, transferases, and lactases. In one aspect, the transgalactosylating polypeptide(s) as disclosed herein may be used together with lactase. This may especially be useful when there is a desire to reduce residual lactose after treatment with the transgalactosylating polypeptide(s) as disclosed herein especially at low lactose levels. A lactase in the context of the present invention is any glycoside hydrolase having the ability to hydrolyse the disaccharide lactose into constituent galactose and glucose monomers. The group of lactases comprises but is not limited to enzymes assigned to subclass EC 3.2.1.108.

Enzymes assigned to other subclasses, such as, e.g., EC 3.2.1.23, may also be lactases in the context of the present invention. A lactase in the context of the invention may have other activities than the lactose hydrolysing activity, such as for example a transgalactosylating activity. In the context of the invention, the lactose hydrolysing activity of the lactase may be referred to as its lactase activity or its beta-galactosidase activity. Enzymes having lactase activity to be used in a method of the present invention may be of animal, of plant or of microbial origin. Preferred enzymes are obtained from microbial sources, in particular from a filamentous fungus or yeast, or from a bacterium. The enzyme may, e.g., be derived from a strain of *Agaricus*, e.g. *A. bisporus; Ascovaginospora; Aspergillus*, e.g. *A. niger, A. awamori, A. foetidus, A. japonicus, A. oryzae; Candida; Chaetomium; Chaetotomastia; Dictyostelium*, e.g. *D. discoideum; Kluveromyces*, e.g. *K. fragilis, K. lactis; Mucor*, e.g. *M. javanicus, M. mucedo, M. subtilissimus; Neurospora*, e.g. *N. crassa; Rhizomucor*, e.g. *R. pusillus; Rhizopus*, e.g. *R. arrhizus, R. japonicus, R. stolonifer; Sclerotinia*, e.g. *S. libertiana; Torula; Torulopsis; Trichophyton*, e.g. *T. rubrum; Whetzelinia*, e.g. *W. sclerotiorum; Bacillus*, e.g. *B. coagulans, B. circulans, B. megaterium, B. novalis, B. subtilis, B. pumilus, B. stearothermophilus, B. thuringiensis; Bifidobacterium*, e.g. *B. longum, B. bifidum, B. animalis; Chryseobacterium; Citrobacter*, e.g. *C. freundii; Clostridium*, e.g. *C. perfringens; Diplodia*, e.g. *D. gossypina; Enterobacter*, e.g. *E. aerogenes, E. cloacae Edwardsiella, E. tarda; Erwinia*, e.g. *E. herbicola; Escherichia*, e.g. *E. coli; Klebsiella*, e.g. *K. pneumoniae; Miriococcum; Myrothesium; Mucor; Neurospora*, e.g. *N. crassa; Proteus*, e.g. *P. vulgaris; Providencia*, e.g. *P. stuartii; Pycnoporus*, e.g. *Pycnoporus cinnabarinus, Pycnoporus sanguineus; Ruminococcus*, e.g. *R. torques; Salmonella*, e.g. *S. typhimurium; Serratia*, e.g. *S. liquefasciens, S. marcescens; Shigella*, e.g. *S. flexneri; Streptomyces*, e.g. *S. antibioticus, S. castaneoglobisporus, S. violeceoruber; Trametes; Trichoderma*, e.g. *T. reesei, T. viride; Yersinia*, e.g. *Y. enterocolitica*. In one embodiment, the lactase is an intracellular component of microorganisms like *Kluyveromyces* and *Bacillus*. *Kluyveromyces*, especially *K. fragilis* and *K. lactis*, and other fungi such as those of the genera *Candida, Torula* and *Torulopsis*, are a common source of fungal lactases, whereas *B. coagulans* and *B circulans* are well known sources for bacterial lactases. Several commercial lactase preparations derived from these organisms are available such as Lactozym® (available from Novozymes, Denmark), HA-Lactase (available from Chr. Hansen, Denmark) and Maxilact® (available from DSM, the Netherlands), all from *K. lactis*. All these lactases are so called neutral lactases having a pH optimum between pH 6 and pH 8. When such lactases are used in the production of, e.g., low-lactose yoghurt, the enzyme treatment will either have to be done in a separate step before fermentation or rather high enzyme dosages have to be used, because their activity drop as the pH decreases during fermentation. Also, these lactases are not suitable for hydrolysis of lactose in milk performed at high temperature, which would in some cases be beneficial in order to keep the microbial count low and thus ensure good milk quality.

In one embodiment, the enzyme is a lactase from a bacterium, e.g. from the family Bifidobacteriaceae, such as from the genus *Bifidobacterium* such as the lactase described in, inter alia, WO 2009/071539 and WO2013/182686.

Materials and Methods

Method 1

Production of Polypeptide

Synthetic genes designed to encode the *Bifidobacterium bifidum* full length (1752 residues) gene with codons optimised for expression in *Bacillus subtilis* were purchased from GeneART (Regensburg, Germany) SEQ ID No. 8.

The *Bifidobacterium bifidum* truncation mutants were constructed using polymerase chain reaction with reverse primers that allowed specific amplification of the selected region of the synthetic gene.

Forward primer:

(SEQ ID NO: 15)

GGGGTA<u>ACTAGT</u>GGAAGATGCAACAAGAAG (SpeI underlined).

The SEQ IDs for the truncation mutants and corresponding reverse primers are indicated in Table 2 below.

TABLE 2

| Truncation mutant | Primer sequence |
|---|---|
| BIF917 (SEQ ID NO: 9) | GCGCTTAATTAATTATGTTTTTTCTGTGCTTGTTC SEQ ID NO: 16 |
| BIF995 (SEQ ID NO: 10) | GCGCTTAATTAATTACAGTGCGCCAATTTCATCAATCA SEQ ID NO: 17 |
| BIF1068 (SEQ ID NO: 11) | GCGCTTAATTAATTATTGAACTCTAATTGTCGCTG SEQ ID NO: 18 |
| BIF1172 (SEQ ID NO: 12) | |
| BIF1241 (SEQ ID NO: 13) | GCGCTTAATTAATTATGTCGCTGTTTTCAGTTCAAT SEQ ID NO: 19 |
| BIF1326 (SEQ ID NO: 14) | GCGCTTAATTAATTAAAATTCTTGTTCTGTGCCCA SEQ ID NO: 20 |
| BIF 1478 | GCGCTTAATTAATTATCTCAGTCTAATTTCGCTTGCGC SEQ ID NO: 21 |

The synthetic gene was cloned into the pBNspe *Bacillus subtilis* expression vector using the unique restriction sites SpeI and PacI (FIG. 1) and the isolated plasmids were transformed into a *Bacillus subtilis* strain. Transformants were restreaked onto LB plates containing 10 μg/mL Neomycin as selection.

A preculture was setup in LB media containing 10 μg/mL Neomycin and cultivated for 7 hours at 37° C. and 180 rpm shaking. 500 μL of this preculture was used to inoculate 50 mL Grant's modified medium containing 10 μg/mL Neomycin at allowed to grow for 68 hours at 33° C. and 180 rpm shaking.

Cells were lysed by addition directly to the culture media of 1 mg/ml Lysozyme (Sigma-Aldrich) and 10 U/ml Benzonase (Merck) final concentrations and incubated for 1 hr at 33° C. at 180 RPM. Lysates were cleared by centrifugation at 10.000× g for 20 minutes and subsequently sterile filtered.

Grant's Modified Media was Prepared According to the Following Directions:

Part I (Autoclave)

| | |
|---|---|
| Soytone | 10 g |
| Bring to 500 mL per liter | |

Part II

| | |
|---|---|
| 1M $K_2HPO_4$ | 3 mL |
| Glucose | 75 g |
| Urea | 3.6 g |
| Grant's 10X MOPS | 100 mL |
| Bring to 400 mL per liter | |

PART I (2 w/w % Soytone) was prepared, and autoclaved for 25 minutes at 121° C.

PART II was prepared, and mixed with PART 1 and pH was adjusted to pH to 7.3 with HCl/NaOH.

The volume was brought to full volume and sterilized through 0.22-μm PES filter.

10×MOPS Buffer was prepared according to the following directions:

| | |
|---|---|
| 83.72 g | Tricine |
| 7.17 g | KOH Pellets |
| 12 g | NaCl |
| 29.22 g | 0.276M K2SO4 |
| 10 mL | 0.528M MgCl2 |
| 10 mL | Grant's Micronutrients 100X |

Bring to app. 900 mL with water and dissolve. Adjust pH to 7.4 with KOH, fill up to 1 L and sterile filter the solution through 0.2 μm PES filter.

100× Micronutrients was prepared according to the following directions:

| | |
|---|---|
| Sodium Citrate•2H2O | 1.47 g |
| CaCl2•2H2O | 1.47 g |
| FeSO4•7H2O | 0.4 g |
| MnSO4•H2O | 0.1 g |
| ZnSO4•H2O | 0.1 g |
| CuCl2•2H2O | 0.05 g |
| CoCl2•6H2O | 0.1 g |
| Na2MoO4•2H2O | 0.1 g |

Dissolve and adjust volume to 1 L with water.

Sterilization was through 0.2 μm PES filter.

Storing was at 4° C. avoid light.

Method 2

Purification and Enzyme Preparations

The filtrated enzyme isolate was concentrated using a VivaSpin ultra filtration device with a 10 kDa MW cut off (Vivaspin 20, Sartorius, Lot #12VS2004) and the concentrate was loaded onto a PD10 desalting column (GE healthcare, Lot #6284601) and eluted in 20 mM Tris-HCl pH 8.6. Chromatography was carried out manually on an Äkta FPLC system (GE Healthcare). 4 mL of the desalted sample, containing aproximately 20 mg protein, was loaded onto a 2 mL HyperQ column (HyperCel™, Q sorbent) eqillibrated with 20 mM Tris-HCl pH 8.6 at a flowrate of 1 ml/min. The column was thoughroughly washed with 30 CV (column volumes) wash buffer and the bound 3-galactosidase was eluted with a 100 CV long gradient into 20 mM Tris-HCl pH 8.6 250 mM NaCl. Remaining impurities on the column were removed with a one-step elution using 20 mM Tris-HCl pH 8.6 500 mM NaCl. Protein in the flow through and elution was analyzed for β-galactosidase activity and by SDS-page.

SDS-page gels were run with the Invitrogen NuPage® Novex 4-12% Bis-Tris gel 1.0 mm, 10 well (Cat #NP0321box), See-Blue® Plus2 prestained Standard (Cat #LC5925) and NuPAGE® MES SDS Running Buffer (Cat #NP0002) according to the manufacturer's protocol. Gels were stained with Simply Blue Safestain (Invitrogen, Cat #LC6060) (FIG. 2).

Method 3

Measuring 3-Galactosidase Activity

Enzymatic activity was measured using the commercially available substrate 2-Nitrophenyl-β-D-Galactopyranoside (ONPG) (Sigma N1127).

ONPG w/o acceptor

| | |
|---|---|
| 100 mM | KPO4 pH 6.0 |
| 12.3 mM | ONPG |

ONPG supplemented with acceptor

| | |
|---|---|
| 100 mM | KPO4 pH 6.0 |
| 20 mM | Cellobiose |
| 12.3 mM | ONPG |

STOP Solution

10% $Na_2CO_3$

10 μl dilution series of purified enzyme was added in wells of a microtiter plates containing 90 μl ONPG-buffer with or without acceptor. Samples were mixed and incubated for 10 min at 37° C., subsequently 100 μl STOP Solution were added to each well to terminate reaction. Absorbance measurements were recorded at 420 nm on a Molecular Device SpectraMax platereader controlled by the Softmax software package.

The ratio of transgalactosylation activity was calculated as follows:

Ratio of transgalctosylation activity=$(Abs420^{+Cellobiose}/Abs420^{-Cellobiose})$ 100, for dilutions where the absorbance was between 0.5 and 1.0 (FIG. 3).

Method 4

Determination of LAU Activity

Principle:

The principle of this assay method is that lactase hydrolyzes 2-o-nitrophenyl-β-D-galactopyranoside (ONPG) into 2-o-nitrophenol (ONP) and galactose at 37° C. The reaction is stopped with the sodium carbonate and the liberated ONP is measured in spectrophotometer or colorimeter at 420 nm.

Reagents:

MES buffer pH 6.4 (100 mM MES pH 6.4, 10 mM $CaCl_2$)): Dissolve 19.52 g MES hydrate (Mw: 195.2 g/mol, Sigma-aldrich #M8250-250G) and 1.470 g $CaCl_2$) di-hydrate (Mw: 147.01 g/mol, Sigma-aldrich) in 1000 ml $ddH_2O$, adjust pH to 6.4 by 10M NaOH. Filter the solution through 0.2 μm filter and store at 4° C. up to 1 month.

ONPG substrate pH 6.4 (12.28 mM ONPG, 100 mM MES pH 6.4, 10 mM $CaCl_2$)): Dissolve 0.370 g 2-o-nitrophenyl-β-D-galactopyranoside (ONPG, Mw: 301.55 g/mol, Sigma-aldrich #N1127) in 100 ml MES buffer pH 6.4 and store dark at 4° C. for up to 7 days.

Stop reagent (10% $Na_2CO_3$): Dissolve 20.0 g $Na_2CO_3$ in 200 ml $ddH_2O$, Filter the solution through 0.2 μm filter and store at RT up to 1 month.

Procedure:

Dilution series of the enzyme sample was made in the MES buffer pH 6.4 and 10 μL of each sample dilution were transferred to the wells of a microtiter plate (96 well format) containing 90 μl ONPG substrate pH 6.4. The samples were mixed and incubated for 5 min at 37° C. using a Thermomixer (Comfort Thermomixer, Eppendorf) and subsequently 100 μl Stop reagent was added to each well to terminate the reaction. A blank was constructed using MES buffer pH 6.4 instead of the enzyme sample. The increase in absorbance at 420 nm was measured at a ELISA reader (SpectraMax platereader, Molecular Device) against the blank.

Calculation of Enzyme Activity:

The molar extinction coefficient of 2-o-nitrophenol (Sigma-aldrich #33444-25G) in MES buffer pH 6.4 was determined ($0.5998\times10^{-6}M^{-1}\times cm^{-1}$). One unit (U) of lactase activity (LAU) was defined as that corresponding to the hydrolysis of 1 nmol of ONPG per minute. Using microtitre plates with a total reaction volume of 200 μL (light path of 0.52 cm) the lactase activity per mL of the enzyme sample may be calculated using the following equation:

$$LAU/\text{ml}\left(\frac{n\text{mol}}{\text{min}\cdot\text{mL}}\right)=\frac{\text{Abs}_{420}\times 200\ \mu\text{L}\times\text{dilution factor}}{0.5998\cdot 10^{3}\cdot\text{nM}^{-1}\cdot\text{cm}^{-1}\times 0.52\ \text{cm}\times 5\ \text{min}\times 0.01\ \text{mL}}$$

Calculation of Specific Activity for BIF917 Shown Herein as SEQ ID NO: 1:

Determination of BIF917 Concentration:

Quantification of the target enzyme (BIF917) and truncation products were determined using the Criterion Stain free SDS-page system (BioRad). Any kD Stain free precast Gel 4-20% Tris-HCl, 18 well (Comb #345-0418) was used with a Serva Tris-Glycine/SDS buffer (BioRad cat. #42529). Gels were run with the following parameters: 200 V, 120 mA, 25 W, 50 min. BSA (1.43 mg/ml) (Sigma-Aldrich, cat. #500-0007) was used as protein standard and Criterion Stain Free Imager (BioRad) was used with Image Lab software (BioRad) for quantification using band intensity with correlation of the tryptophan content.

The specific LAU activity of BIF917 was determined from crude ferment (ultra filtration concentrate) of two independent fermentations (as described in method 1) and using 5 different dilutions (see table 1).

The specific activity of BIF917 was found to be 21.3 LAU/mg or 0.0213 LAU/ppm.

TABLE 1

Determination of BIF917 specific activity

| Sample ID | Enzyme | Fermentation | Dilution factor | Activity LAU/ml | Protein (BIF917) concentration mg/ml | Protein (BIF917) concentration ppm | Specific activity LAU/mg | Specific activity LAU/ppm |
|---|---|---|---|---|---|---|---|---|
| 1 | BIF 917 | a | 5 | 26.9 | 1.23 | 1232 | 21.9 | 0.0219 |
| 2 | BIF 917 | a | 10 | 53.9 | 2.44 | 2437 | 22.1 | 0.0221 |
| 3 | BIF 917 | a | 10 | 75.4 | 3.56 | 3556 | 21.2 | 0.0212 |
| 4 | BIF 917 | a | 20 | 163.9 | 7.78 | 7778 | 21.1 | 0.0211 |
| 5 | BIF 917 | a | 30 | 233.6 | 11.06 | 11065 | 21.1 | 0.0211 |
| 6 | BIF 917 | b | 5 | 30.26825 | 1.34 | 1342 | 22.6 | 0.0226 |
| 7 | BIF 917 | b | 10 | 55.91536 | 2.61 | 2607 | 21.4 | 0.0214 |
| 8 | BIF 917 | b | 10 | 76.96056 | 3.70 | 3697 | 20.8 | 0.0208 |
| 9 | BIF 917 | b | 20 | 156.986 | 7.75 | 7755 | 20.2 | 0.0202 |
| 10 | BIF 917 | b | 30 | 236.9734 | 11.45 | 11452 | 20.7 | 0.0207 |
| | | | | | | Arg | 21.3 | 0.0213 |
| | | | | | | Std | 0.700976 | 0.000701 |

Example 1

An experiment was conducted to test the effects of diafiltration (DF), bentionite treatment (BT) and heat treatment (HT) on the physical stability of BIF917 formulated with glycerol. Formulation details are given in the Table below:

| Formulation | | Sample 1 | Sample 2 | Sample 3 | Sample 4 | Sample 5 | Sample 6 | Sample 7 | Sample 8 |
|---|---|---|---|---|---|---|---|---|---|
| Expected Activity | U/g | 1370 | 685 | 685 | 685 | 685 | 685 | 685 | 685 |
| Measured Activity | U/g | 1012 | 863 | 1016 | 847 | 1005 | 897 | 930 | 850 |
| Cosolvent | — w/w | 0.00% | 49.70% | 49.70% | 49.70% | 49.80% | 49.80% | 49.80% | 49.80% |
| NaCl | — w/w | 0.00% | 0.00% | 0.00% | 0.00% | 0.00% | 0.00% | 0.00% | 0.00% |
| preservative | — w/w | 0.14% | 0.14% | 0.14% | 0.14% | 0.14% | 0.14% | 0.14% | 0.14% |
| UFC | — w/w | 99.37% | 49.71% | 49.68% | 49.66% | 49.83% | 49.83% | 49.81% | 49.83% |
| Water | — w/w | 0.00% | 0.00% | 0.00% | 0.00% | 0.00% | 0.00% | 0.00% | 0.00% |

| nr | Enzyme id: | "variant" | Info | Time = X days | Dilut. Factor | −cello-biose Avg-bl | +cello-biose Avg-bl | X dilut. F −cello-biose Avg-bl | X dilut. F +cello-biose Avg-bl | Ratio % | Akt Nmol/min. −cello-brose | Akt Nmol/min +cello-biose |
|---|---|---|---|---|---|---|---|---|---|---|---|---|
| 1 | MW Stability #3 - sample 1 | Control | BIF_917 | 0 | 200 | 0.395 | 1.093 | 78.980 | 218.500 | 277 | 1012.9 | 2802.2 |
| 2 | MW Stability #3 - sample 2 | HT | | 0 | 200 | 0.336 | 0.988 | 67.290 | 197.630 | 294 | 863.0 | 2534.5 |
| 3 | MW Stability #3 - sample 3 | BT | | 0 | 200 | 0.396 | 1.134 | 79.230 | 226.820 | 286 | 1016.1 | 2908.9 |
| 4 | MW Stability #3 - sample 4 | BT + HT | | 0 | 200 | 0.330 | 0.983 | 66.020 | 196.610 | 298 | 846.7 | 2521.4 |
| 5 | MW Stability #3 - sample 5 | DF | | 0 | 200 | 0.392 | 1.120 | 78.380 | 223.940 | 286 | 1005.2 | 2871.9 |
| 6 | MW Stability #3 - sample 6 | DF + HT | | 0 | 200 | 0.350 | 1.013 | 69.930 | 202.610 | 290 | 896.8 | 2598.4 |
| 7 | MW Stability #3 - sample 7 | DF + BT | | 0 | 200 | 0.362 | 1.057 | 72.480 | 211.300 | 292 | 929.5 | 2709.8 |
| 8 | MW Stability #3 - sample 8 | DF + BT + HT | | 0 | 200 | 0.332 | 0.922 | 66.310 | 184.400 | 278 | 850.4 | 2364.9 |

The Samples were incubated at each of the following storage conditions, 5° C., 20° C. and 3TC.

The results are shown in FIG. 1.

Example 2

The effect of the formulation on actual GOS forming enzymatic activity on the application relevant substrate, lactose, was also investigated. It was surprisingly found that the presence of glycerol in the application had significant negative effect on the GOS generation activity due to generation of the undesired galactosyl-glycerol rather than the desired GOS in the application. The presence of the galactosyl-glycerol can only be detected when the actual reaction products are analysed by for example HPLC and not by the chromogenic substrate ONPG since this assay only measure the release of ONP. In particular it was surprisingly found (as illustrated in FIGS. 2 and 3) that the use of greater than 0.1 wt % of glycerol perturbs the transgalactosylation reaction resulting in lower yields of the desired GOS. The low amounts of glycerol need to perturb the GOS generation indicates that the enzyme is an efficient galactosyl-glycerol generating enzyme in the presence of free glycerol.

Example 3

The BIF917 enzyme was mixed to provide an intermediate formulation according to the following Table and subsequently spray-dried.

| Composition Name | | #1 | #2 | #3 | #4 | #5 |
|---|---|---|---|---|---|---|
| Spray Feed preparation | Target value | Actual value | Actual value | Actual value | Actual value | Actual value |
| 10% NaCl | kg | 5.000 | | | | |
| pH = 5, carbon treatment, 0.4% sorbate + 10% NaCl | kg | | 5.000 | | | |
| 20% NaCl | kg | | | 5.000 | | |
| Lead sorbate | kg | | | | 5.000 | |
| Lead sorbate | kg | | | | | 5.000 |
| MD DE20 | kg | 1.000 | 1.000 | 1.000 | 1.000 | 2.000 |
| | | Composition | | | | |
| 10% NaCl | % | 83.3% | 0.0% | 0.0% | 0.0% | 0.0% |
| pH = 5, carbon treatment, 0.4% sorbate + 10% NaCl | % | 0.0% | 83.3% | 0.0% | 0.0% | 0.0% |
| Lead 20% NaCl | % | 0.0% | 0.0% | 83.3% | 0.0% | 0.0% |
| Lead sorb | % | 0.0% | 0.0% | 0.0% | 83.3% | 0.0% |
| Lead sorb | % | 0.0% | 0.0% | 0.0% | 0.0% | 71.4% |
| MD DE20 | % | 16.7% | 16.7% | 16.7% | 16.7% | 28.6% |
| Mix temp | ° C. | | | | | |
| Mix time before spray | min | <30 min | <30 min | <30 min | <30 min | <30 min |

| | | #1 | #2 | #3 | #4 | #5 |
|---|---|---|---|---|---|---|
| Spray Drying | | Actual value | Actual value | Actual value | Actual value | Actual value |
| Spray time | min | 9.5 | 10 | 9 | 11.5 | 11 |
| Inlet air temp (before heating): | 0° C. | outdoor | outdoor | outdoor | outdoor | outdoor |
| Process air temp inlet | 165° C. | 175 | 170 | 172 | 172 | 174 |
| Process air temp outlet | 85° C. | 93-86 | 85-81 | 87-86 | 85-81 | 84-79 |
| Process air flow | 600 m3/hr | | | | | |

-continued

| | | | | | | |
|---|---|---|---|---|---|---|
| Atomizer wheel Ø120 mm | 12000 rpm | 20000 | 20000 | 20000 | 20000 | 20000 |
| Feed rate (kg dispersion/hr) | | 37.9 | 36.0 | 40.0 | 31.3 | 38.2 |
| WM505U pump/8 mm ID Ø tubing) | rpm | 127-135 | 127-125 | 155 | 108-106 | 155 |
| Sample | | 1.089 | 1.22 | 1.67 | 1.089 | 1.747 |
| sample B-grade | up/down | 0.296 | 0.656 | 0.783 | 0.296 | 0.635 |
| Yield | | 61.6% | 83.4% | 89.2% | 79.1% | 86.6% |
| DM in enzyme raw material | | 25.0% | 25.0% | 35.0% | 15.0% | 15.0% |
| Powder temparature | ° C. | >43 | >41 | >48 | >44 | >49 |

The effect of the formulation on activity was investigated at each of the following storage conditions: 5° C., 20° C. and 3TC. The results for sample #1, 3 and 5 are shown in FIG. 4 and they show that good transgalactosylation activity is retained following formulation.

Example 4

The effect of potato starch on dust reduction is illustrated in FIG. 5.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in chemistry, biochemistry, biology, or related fields are intended to be within the scope of the following claims.

List of Sequences

```
>SEQ ID NO: 1 (BIF_917)
vedatrsdsttqmsstpevvyssavdskqnrtsdfdanwkfmlsdsvqaqdpafddsawqqvdlphdysitqkys
qsneaesaylpggtgwyrksftidrdlagkriainfdgvymnatvwfngvklgthpygyspfsfdltgnakfggentivv
kvenrlpssrwysgsgiyrdvtltvtdgvhvgnngvaiktpslatqnggdytmnlttkvandteaaanitlkqtvfpkggk
tdaaigtvttasksiaagasadvtstitaaspklwsiknpnlytvrtevlnggkvldtydteygfrwtgfdatsgfsingekv
klkgvsmhhdqgslgavanrraierqveilqkmgvnsirtthnpaakalidvcnekgvlvveevfdmwnrskngnte
dygkwfgqaiagdnavlggdkdetwakfdltstinrdrnapsvimwslgnemmegisgsysgfpatsaklvawtka
adstrpmtygdnkikanwnesntmgdnltanggvvgtnysdganydkirtthpswaiygsetasainsrgiynrttgg
aqssdkqltsydnsavgwgavassawydvvqrdfvagtyvwtgfdylgeptpwngtgsgavgswpspknsyfgiv
dtagfpkdtyyfyqsqwnddvhtlhilpawnenvvakgsgnnvpvvvytdaakvklyftpkgstekrligeksftkktta
agytyqvyegsdkdstahknmyltwnvpwaegtisaeaydennrlipegstegnasytttgkaaklkadadrktitad
gkdlsyievdvtdanghivpdaanrytfdvkgagklvgvdngsspdhdsyqadnrkafsgkvlaivqstkeageitvt
akadglqsstvkiattavpgtstekt

>SEQ ID NO: 2 (BIF_995)
vedatrsdsttqmsstpevvyssavdskqnrtsdfdanwkfmlsdsvqaqdpafddsawqqvdlphdysitqkys
qsneaesaylpggtgwyrksftidrdlagkriainfdgvymnatvwfngvklgthpygyspfsfdltgnakfggentivv
kvenrlpssrwysgsgiyrdvtltvtdgvhvgnngvaiktpslatqnggdytmnlttkvandteaaanitlkqtvfpkggk
tdaaigtvttasksiaagasadvtstitaaspklwsiknpnlytvrtevlnggkvldtydteygfrwtgfdatsgfslngekv
klkgvsmhhdqgslgavanrraierqveilqkmgvnsirtthnpaakalidvcnekgvlvveevfdmwnrskngnte
dygkwfgqaiagdnavlggdkdetwakfdltstinrdrnapsvimwslgnemmegisgsysgfpatsaklvawtka
adstrpmtygdnkikanwnesntmgdnltanggvvgtnysdganydkirtthpswaiygsetasainsrgiynrttgg
aqssdkqltsydnsavgwgavassawydvvqrdfvagtyvwtgfdylgeptpwngtgsgavgswpspknsyfgiv
dtagfpkdtyyfyqsqwnddvhtlhilpawnenvvakgsgnnvpvvvytdaakvklyftpkgstekrligeksftkktta
agytyqvyegsdkdstahknmyltwnvpwaegtisaeaydennrlipegstegnasytttgkaaklkadadrktitad
gkdlsyievdvtdanghivpdaanrytfdvkgagklvgvdngsspdhdsyqadnrkafsgkvlaivqstkeageitvt
akadglqsstvkiattavpgtstektvrsfyysrnyyvktgnkpilpsdvevrysdgtsdrqnvtwdaysddqiakagsf
svagtvagqkisvrytmideigal

>SEQ ID NO: 3 (BIF_1068)
Vedatrsdsttqmsstpevvyssavdskqnrtsdfdanwkfmlsdsvqaqdpafddsawqqvdlphdysitqkys
qsneaesaylpggtgwyrksftidrdlagkriainfdgvymnatvwfngvklgthpygyspfsfdltgnakfggentivv
kvenrlpssrwysgsgiyrdvtltvtdgvhvgnngvaiktpslatqnggdytmnlttkvandteaaanitlkqtvfpkggk
tdaaigtvttasksiaagasadvtstitaaspklwsiknpnlytvrtevlnggkvldtydteygfrwtgfdatsgfslngekv
klkgvsmhhdqgslgavanrraierqveilqkmgvnsirtthnpaakalidvcnekgvlvveevfdmwnrskngnte
dygkwfgqaiagdnavlggdkdetwakfdltstinrdrnapsvimwslgnemmegisgsysgfpatsaklvawtka
adstrpmtygdnkikanwnesntmgdnltanggvvgtnysdganydkirtthpswaiygsetasainsrgiynrttgg
aqssdkqltsydnsavgwgavassawydvvqrdfvagtyvwtgfdylgeptpwngtgsgavgswpspknsyfgiv
dtagfpkdtyyfyqsqwnddvhtlhilpawnenvvakgsgnnvpvvvytdaakvklyftpkgstekrligeksftkktta
agytyqvyegsdkdstahknmyltwnvpwaegtisaeaydennrlipegstegnasytttgkaaklkadadrktitad
gkdlsyievdvtdanghivpdaanrytfdvkgagklvgvdngsspdhdsyqadnrkafsgkvlaivqstkeageitvt
akadglqsstvkiattavpgtstektvrsfyysrnyyvktgnkpilpsdvevrysdgtsdrqnvtwdaysddqiakagsf
svagtvagqkisvrytmideigallnysastpvgtpavlpgsrpavlpdgtvtsanfavhwtkpadtvyntagtvkvpgt
atvfgkefkvtatirvq

>SEQ ID NO: 4 (BIF_1172)
vedatrsdsttqmsstpevvyssavdskqnrtsdfdanwkfmlsdsvqaqdpafddsawqqvdlphdysitqkys
qsneaesaylpggtgwyrksftidrdlagkriainfdgvymnatvwfngvklgthpygyspfsfdltgnakfggentivv
kvenrlpssrwysgsgiyrdvtltvtdgvhvgnngvaiktpslatqnggdytmnlttkvandteaaanitlkqtvfpkggk
```

-continued tdaaigtvttasksiaagasadvtstitaaspklwsiknpnlytvrtevlnggkvldtydteygfrwtgfdatsgfslngekv
klkgvsmhhdqgslgavanrraierqveilqkmgvnsirtthnpaakalidvcnekgvlvveevfdmwnrskngnte
dygkwfgqaiagdnavlggdkdetwakfdltstinrdrnapsvimwslgnemmegisgsysgfpatsaklvawtka
adstrpmtygdnkikanwnesntmgdnltanggvvgtnysdganydkirtthpswaiygsetasainsrgiynrttgg
aqssdkqltsydnsavgwgavassawydvvqrdfvagtyvwtgfdylgeptpwngtgsgavgswpspknsyfgiv
dtagfpkdtyyfyqsqwnddvhtlhilpawnenvvakgsgnnvpvvvytdaakvklyftpkgstekrligeksftkktta
agytyqvyegsdkdstahknmyltwnvpwaegtisaeaydennrlipegstegnasytttgkaaklkadadrktitad
gkdlsyievdvtdanghivpdaanrvtfdvkgagklvgvdngsspdhdsyqadnrkafsgkvlaivqstkeageitvt
akadglqsstvkiattavpgtstektvrsfyysrnyyvktgnkpilpsdvevrysdgtsdrqnvtwdaysddqiakagsf
svagtvagqkisvrvtmideigallnysastpvgtpavlpgsrpavlpdgtvtsanfavhwtkpadtvyntagtvkvpgt
atvfgkefkvtatirvqrsqvtigssysgnalrltqnipadkqsdtldaikdgsttvdantggganpsawtnwayskagh
ntaeitfeyateqqlgqivmyffrdsnavrfpdagktkiqi >SEQ ID NO: 5 (BIF_1241)
vedatrsdsttqmsstpevvyssavdskqnrtsdfdanwkfmlsdsvqaqdpafddsawqqvdlphdysitqkys
qsneaesaylpggtgwyrksftidrdlagkriainfdgvymnatvwfngvklgthpygyspfsfdltgnakfggentivv
kvenrlpssrwysgsgiyrdvtltvtdgvhvgnngvaiktpslatqnggdytmnlttkvandteaaanitlkqtvfpkggk
tdaaigtvttasksiaagasadvtstitaaspklwsiknpnlytvrtevlnggkvldtydteygfrwtgfdatsgfslngekv
klkgvsmhhdqgslgavanrraierqveilqkmgvnsirtthnpaakalidvcnekgvlvveevfdmwnrskngnte
dygkwfgqaiagdnavlggdkdetwakfdltstinrdrnapsvimwslgnemmegisgsysgfpatsaklvawtka
adstrpmtygdnkikanwnesntmgdnltanggvvgtnysdganydkirtthpswaiygsetasainsrgiynrttgg
aqssdkqltsydnsavgwgavassawydvvqrdfvagtyvwtgfdylgeptpwngtgsgavgswpspknsyfgiv
dtagfpkdtyyfyqsqwnddvhtlhilpawnenvvakgsgnnvpvvvytdaakvklyftpkgstekrligeksftkktta
agytyqvyegsdkdstahknmyltwnvpwaegtisaeaydennrlipegstegnasytttgkaaklkadadrktitad
gkdlsyievdvtdanghivpdaanrvtfdvkgagklvgvdngsspdhdsyqadnrkafsgkvlaivqstkeageitvt
akadglqsstvkiattavpgtstektvrsfyysrnyyvktgnkpilpsdvevrysdgtsdrqnvtwdaysddqiakagsf
svagtvagqkisvrvtmideigallnysastpvgtpavlpgsrpavlpdgtvtsanfavhwtkpadtvyntagtvkvpgt
atvfgkefkvtatirvqrsqvtigssysgnalrltqnipadkqsdtldaikdgsttvdantggganpsawtnwayskagh
ntaeitfeyateqqlgqivmyffrdsnavrfpdagktkiqisadgknwtdlaatetiaaqessdrvkpytydfapvgatfv
kvtvtnadtttpsgvvcaglteielktat >SEQ ID NO: 6 (BIF_1326)
vedatrsdsttqmsstpevvyssavdskqnrtsdfdanwkfmlsdsvqaqdpafddsawqqvdlphdysitqkys
qsneaesaylpggtgwyrksftidrdlagkriainfdgvymnatvwfngvklgthpygyspfsfdltgnakfggentivv
kvenrlpssrwysgsgiyrdvtltvtdgvhvgnngvaiktpslatqnggdytmnlttkvandteaaanitlkqtvfpkggk
tdaaigtvttasksiaagasadvtstitaaspklwsiknpnlytvrtevlnggkvldtydteygfrwtgfdatsgfslngekv
klkgvsmhhdqgslgavanrraierqveilqkmgvnsirtthnpaakalidvcnekgvlvveevfdmwnrskngnte
dygkwfgqaiagdnavlggdkdetwakfdltstinrdrnapsvimwslgnemmegisgsysgfpatsaklvawtka
adstrpmtygdnkikanwnesntmgdnltanggvvgtnysdganydkirtthpswaiygsetasainsrgiynrttgg
aqssdkqltsydnsavgwgavassawydvvqrdfvagtyvwtgfdylgeptpwngtgsgavgswpspknsyfgiv
dtagfpkdtyyfyqsqwnddvhtlhilpawnenvvakgsgnnvpvvvytdaakvklyftpkgstekrligeksftkktta
agytyqvyegsdkdstahknmyltwnvpwaegtisaeaydennrlipegstegnasytttgkaaklkadadrktitad
gkdlsyievdvtdanghivpdaanrvtfdvkgagklvgvdngsspdhdsyqadnrkafsgkvlaivqstkeageitvt
akadglqsstvkiattavpgtstektvrsfyysrnyyvktgnkpilpsdvevrysdgtsdrqnvtwdaysddqiakagsf
svagtvagqkisvrvtmideigallnysastpvgtpavlpgsrpavlpdgtvtsanfavhwtkpadtvyntagtvkvpgt
atvfgkefkvtatirvqrsqvtigssysgnalrltqnipadkqsdtldaikdgsttvdantggganpsawtnwayskagh
ntaeitfeyateqqlgqivmyffrdsnavrfpdagktkiqisadgknwtdlaatetiaaqessdrvkpytydfapvgatfv
kvtvtnadtttpsgvvcaglteielktatskfvtntsaalssltvngtkvsdsvlaagsyntpaiiadvkaegegnasvtvlp
andnvirvitesedhvtrktftinlgteqef >SEQ ID NO: 7 *Bifidobacterium bifidum* glycoside hydrolase catalytic core
qnrtsdfdanwkfmlsdsvqaqdpafddsawqqvdlphdysitqkysqsneaesaylpggtgwyrksftidrdlagk
riainfdgvymnatvwfngvklgthpygyspfsfdltgnakfggentivvkvenrlpssrwysgsgiyrdvtltvtdgvhv
gnngvaiktpslatqnggdytmnlttkvandteaaanitlkqtvfpkggktdaaigtvttasksiaagasadvtstitaasp
klwsiknpnlytvrtevlnggkvldtydteygfrwtgfdatsgfslngekvklkgvsmhhdqgslgavanrraierqveilq
kmgvnsirtthnpaakalidvcnekgvlvveevfdmwnrskngntedygkwfgqaiagdnavlggdkdetwakfdl
tstinrdrnapsvimwslgnemmegisgsysgfpatsaklvawtkaadstrpmty >SEQ ID NO: 8 nucleotide sequence encoding full length
gcagttgaagatgcaacaagaagcgatagcacaacacaaatgtcatcaacaccggaagttgtttattcatcagcggt
cgatagcaaacaaaatcgcacaagcgattttgatgcgaactggaaatttatgctgtcagatagcgttcaagcacaag
atccggcatttgatgattcagcatggcaacaagttgatctgccgcatgattatagcatcacacagaaatatagccaaag
caatgaagcagaatcagcatatcttccgggaggcacaggctggtatagaaaaagctttacaattgatagagatctgg
caggcaaacgcattgcgattaattttgatggcgtctatatgaatgcaacagtctggtttaatggcgttaaactgggcaca
catccgtatggctattcaccgttttcatttgatctgacaggcaatgcaaaatttggcggagaaaacacaattgtcgtcaaa
gttgaaaatagactgccgtcatcaagatggtattcaggcagcggcatttatagagatgttacactgacagttacagatg
gcgttcatgttggcaataatggcgtcgcaattaaaacaccgtcactggcaacacaaaatggcggagatgtcacaatg
aacctgacaacaaaagtcgcgaatgatacagaagcagcagcgaacattacactgaaacagacagthttccgaaa
ggcggaaaaacggatgcagcaattggcacagttacaacagcatcaaaatcaattgcagcaggcgcatcagcagat
gttacaagcacaattacagcagcaagcccgaaactgtggtcaattaaaaacccgaacctgtatacagttagaacag
aagttctgaacggaggcaaagttctggatacatatgatacagaatatggctttcgctggacaggctttgatgcaacatc
aggcttttcactgaatggcgaaaaagtcaaactgaaaggcgttagcatgcatcatgatcaaggctcacttggcgcagtt
gcaaatagacgcgcaattgaaagacaagtcgaaatcctgcaaaaaatgggcgtcaatagcattcgcacaacacat
aatccggcagcaaaagcactgattgatgtctgcaatgaaaaaggcgttctggttgtcgaagaagtctttgatatgtgga
accgcagcaaaaatggcaacacggaagattatggcaaatggtttggccaagcaattgcaggcgataatgcagttct
gggaggcgataaagatgaaacatgggcgaaatttgatcttacatcaacaattaaccgcgatagaaatgcaccgtca
gttattatgtggtcactgggcaatgaaatgatggaaggcatttcaggctcagtttcaggctttccggcaacatcagcaaa
actggttgcatggacaaaagcagcagattcaacaagaccgatgacatatggcgataacaaaattaaagcgaactg
gaacgaatcaaatacaatgggcgataatctgacagcaaatggcggagttgttggcacaaattattcagatggcgcaa
actatgataaaattcgtacaacacatccgtcatgggcaatttatggctcagaaacagcatcagcgattaatagccgtgg
catttataatagaacaacaggcggagcacaatcatcagataaacagctgacaagctatgataattcagcagttggct -continued

```
ggggagcagttgcatcatcagcatggtatgatgttgttcagagagattttgtcgcaggcacatatgtttggacaggatttg
attatctgggcgaaccgacaccgtggaatggcacaggctcaggcgcagttggctcatggccgtcaccgaaaaatag
ctattttggcatcgttgatacagcaggctttccgaaagatacatattatttttatcagagccagtggaatgatgatgttcata
cactgcatattcttccggcatggaatgaaaatgttgttgcaaaaggctcaggcaataatgttccggttgtcgtttatacag
atgcagcgaaagtgaaactgtattttacaccgaaaggctcaacagaaaaaagactgatcggcgaaaaatcatttac
aaaaaaaacaacagcggcaggctatacatatcaagtctatgaaggcagcgataaagattcaacagcgcataaaa
acatgtatctgacatggaatgttccgtgggcagaaggcacaatttcagcggaagcgtatgatgaaaataatcgcctga
ttccggaaggcagcacagaaggcaacgcatcagttacaacaacaggcaaagcagcaaaactgaaagcagatgc
ggatcgcaaaacaattacagcggatggcaaagatctgtcatatattgaagtcgatgtcacagatgcaaatggccatat
tgttccggatgcagcaaatagagtcacatttgatgttaaaggcgcaggcaaactggttggcgttgataatggctcatca
ccggatcatgattcatatcaagcggataaccgcaaagcattttcaggcaaagtcctggcaattgttcagtcaacaaaa
gaagcaggcgaaattacagttacagcaaaagcagatggcctgcaatcaagcacagttaaaattgcaacaacagca
gttccgggaacaagcacagaaaaaacagtccgcagcttttattacagccgcaactattatgtcaaaacaggcaaca
aaccgattctgccgtcagatgttgaagttcgctattcagatggaacaagcgatagacaaaacgttacatgggatgcag
tttcagatgatcaaattgcaaaagcaggctcattttcagttgcaggcacagttgcaggccaaaaaattagcgttcgcgtc
acaatgattgatgaaattggcgcactgctgaattattcagcaagcacaccggttggcacaccggcagttcttccgggat
caagaccggcagtcctgccggatggcacagtcacatcagcaaattttgcagtccattggacaaaaccggcagatac
agtctataatacagcaggcacagtcaaagtaccgggaacagcaacagthttggcaaagaatttaaagtcacagcg
acaattagagttcaaagaagccaagttacaattggctcatcagtttcaggaaatgcactgagactgacacaaaatatt
ccggcagataaacaatcagatacactggatgcgattaaagatggctcaacaacagttgatgcaaatacaggcgga
ggcgcaaatccgtcagcatggacaaattgggcatattcaaaagcaggccataacacagcggaaattacatttgaata
tgcgacagaacaacaactgggccagatcgtcatgtattthttcgcgatagcaatgcagttagatttccggatgctggca
aaacaaaaattcagatcagcgcagatggcaaaaattggacagatctggcagcaacagaaacaattgcagcgcaa
gaatcaagcgatagagtcaaaccgtatacatatgattttgcaccggttggcgcaacatttgttaaagtgacagtcacaa
acgcagatacaacaacaccgtcaggcgttgtttgcgcaggcctgacagaaattgaactgaaaacagcgacaagca
aatttgtcacaaatacatcagcagcactgtcatcacttacagtcaatggcacaaaagtttcagattcagttctggcagca
ggctcatataacacaccggcaattatcgcagatgttaaagcggaaggcgaaggcaatgcaagcgttacagtccttcc
ggcacatgataatgttattcgcgtcattacagaaagcgaagatcatgtcacacgcaaaacatttacaatcaacctggg
cacagaacaagaatttccggctgattcagatgaaagagattatccggcagcagatatgacagtcacagttggctcag
aacaaacatcaggcacagcaacagaaggaccgaaaaaatttgcagtcgatggcaacacatcaacatattggcata
gcaattggacaccgacaacagttaatgatctgtggatcgcgtttgaactgcaaaaaccgacaaaactggatgcactg
agatatcttccgcgtccggcaggctcaaaaaatggcagcgtcacagaatataaagttcaggtgtcagatgatggaac
aaactggacagatgcaggctcaggcacatggacaacggattatggctggaaactggcggaatttaatcaaccggtc
acaacaaaacatgttagactgaaagcggttcatacatatgcagatagcggcaacgataaatttatgagcgcaagcg
aaattagactgagaaaagcggtcgatacaacggatatttcaggcgcaacagttacagttccggcaaaactgacagtt
gatagagttgatgcagatcatccggcaacatttgcaacaaaagatgtcacagttacactgggagatgcaacactgag
atatggcgttgattatctgctggattatgcaggcaatacagcagttggcaaagcaacagtgacagttagaggcattgat
aaatattcaggcacagtcgcgaaaacatttacaattgaactgaaaaatgcaccggcaccggaaccgacactgacat
cagttagcgtcaaaacaaaaccgagcaaactgacatatgttgtcggagatgcatttgatccggcaggcctggttctgc
aacatgatagacaagcagatagacctccgcaaccgctggttggcgaacaagcggatgaacgcggactgacatgc
ggcacaagatgcgatagagttgaacaactgcgcaaacatgaaaatagagaagcgcatagaacaggcctggatca
tctggaatttgttggcgcagcagatggcgcagttggagaacaagcaacatttaaagtccatgtccatgcagatcaggg
agatggcagacatgatgatgcagatgaacgcgatattgatccgcatgttccggtcgatcatgcagttggcgaactggc
aagagcagcatgccatcatgttattggcctgagagtcgatacacatagacttaaagcaagcggctttcaaattccggct
gatgatatggcagaaatcgatcgcattacaggctttcatcgttttgaacgccatgtc
```

>SEQ ID NO: 9 nucleotide sequence encoding BIF_917

```
gttgaagatgcaacaagaagcgatagcacaacacaaatgtcatcaacaccggaagttgtttattcatcagcggtcgat
agcaaacaaaatcgcacaagcgattttgatgcgaactggaaatttatgctgtcagatagcgttcaagcacaagatccg
gcatttgatgattcagcatggcaacaagttgatctgccgcatgattatagcatcacacagaaatatagccaaagcaatg
aagcagaatcagcatatcttccgggaggcacaggctggtatagaaaaagctttacaattgatagagatctggcaggc
aaacgcattgcgattaattttgatggcgtctatatgaatgcaacagtctggtttaatggcgttaaactgggcacacatccg
tatggctattcaccgttttcatttgatctgacaggcaatgcaaaatttggcggagaaaacacaattgtcgtcaaagttgaa
aatagactgccgtcatcaagatggtattcaggcagcggcatttatagagatgttacactgacagttacagatggcgttc
atgttggcaataatggcgtcgcaattaaaacaccgtcactggcaacacaaaatggcggagatgtcacaatgaacctg
acaacaaaagtcgcgaatgatacagaagcagcagcgaacattacactgaaacagacagtttttccgaaaggcgga
aaaacggatgcagcaattggcacagttacaacagcatcaaaatcaattgcagcaggcgcatcagcagatgttacaa
gcacaattacagcagcaagcccgaaactgtggtcaattaaaaacccgaacctgtatacagttagaacagaagttctg
aacggaggcaaagttctggatacatatgatacagaatatggctttcgctggacaggctttgatgcaacatcaggcttttc
actgaatggcgaaaaagtcaaactgaaaggcgttagcatgcatcatgatcaaggctcacttggcgcagttgcaaata
gacgcgcaattgaaagacaagtcgaaatcctgcaaaaaatgggcgtcaatagcattcgcacaacacataatccgg
cagcaaaagcactgattgatgtctgcaatgaaaaaggcgttctggttgtcgaagaagtctttgatatgtggaaccgcag
caaaaatggcaacacggaagattatggcaaatggtttggccaagcaattgcaggcgataatgcagttctgggaggc
gataaagatgaaacatgggcgaaatttgatcttacatcaacaattaaccgcgatagaaatgcaccgtcagttattatgt
ggtcactgggcaatgaaatgatggaaggcatttcaggctcagtttcaggctttccggcaacatcagcaaaactggttgc
atggacaaaagcagcagattcaacaagaccgatgacatatggcgataacaaaattaaagcgaactggaacgaat
caaatacaatgggcgataatctgacagcaaatggcggagttgttggcacaaattattcagatggcgcaaactatgata
aaattcgtacaacacatccgtcatgggcaatttatggctcagaaacagcatcagcgattaatagccgtggcatttataat
agaacaacaggcggagcacaatcatcagataaacagctgacaagctatgataattcagcagttggctggggagca
gttgcatcatcagcatggtatgatgttgttcagagagattttgtcgcaggcacatatgtttggacaggatttgattatctggg
cgaaccgacaccgtggaatggcacaggctcaggcgcagttggctcatggccgtcaccgaaaaatagctattttggca
tcgttgatacagcaggctttccgaaagatacatattatttttatcagagccagtggaatgatgatgttcatacactgcatatt
cttccggcatggaatgaaaatgttgttgcaaaaggctcaggcaataatgttccggttgtcgtttatacagatgcagcgaa
agtgaaactgtattttacaccgaaaggctcaacagaaaaaagactgatcggcgaaaaatcatttacaaaaaaaaca
acagcggcaggctatacatatcaagtctatgaaggcagcgataaagattcaacagcgcataaaaacatgtatctgac
atggaatgttccgtgggcagaaggcacaatttcagcggaagcgtatgatgaaaataatcgcctgattccggaaggca
gcacagaaggcaacgcatcagttacaacaacaggcaaagcagcaaaactgaaagcagatgcggatcgcaaaa
```

-continued caattacagcggatggcaaagatctgtcatatattgaagtcgatgtcacagatgcaaatggccatattgttccggatgc
agcaaatagagtcacatttgatgttaaaggcgcaggcaaactggttggcgttgataatggctcatcaccggatcatgat
tcatatcaagcggataaccgcaaagcattttcaggcaaagtcctggcaattgttcagtcaacaaaagaagcaggcga
aattacagttacagcaaaagcagatggcctgcaatcaagcacagttaaaattgcaacaacagcagttccgggaaca
agcacagaaaaaaca >SEQ ID NO: 10 nucleotide sequence encoding BIF_995
gttgaagatgcaacaagaagcgatagcacaacacaaatgtcatcaacaccggaagttgtttattcatcagcggtcgat
agcaaacaaaatcgcacaagcgattttgatgcgaactggaaatttatgctgtcagatagcgttcaagcacaagatccg
gcatttgatgattcagcatggcaacaagttgatctgccgcatgattatagcatcacacagaaatatagccaaagcaatg
aagcagaatcagcatatcttccgggaggcacaggctggtatagaaaaagctttacaattgatagagatctggcaggc
aaacgcattgcgattaattttgatggcgtctatatgaatgcaacagtctggtttaatggcgttaaactgggcacacatccg
tatggctattcaccgttttcatttgatctgacaggcaatgcaaaatttggcggagaaaacacaattgtcgtcaaagttgaa
aatagactgccgtcatcaagatggtattcaggcagcggcatttatagagatgttacactgacagttacagatggcgttc
atgttggcaataatggcgtcgcaattaaaacaccgtcactggcaacacaaaatggcggagatgtcacaatgaacctg
acaacaaaagtcgcgaatgatacagaagcagcagcgaacattacactgaaacagacagtttttccgaaaggcgga
aaaacggatgcagcaattggcacagttacaacagcatcaaaatcaattgcagcaggcgcatcagcagatgttacaa
gcacaattacagcagcaagcccgaaactgtggtcaattaaaaacccgaacctgtatacagttagaacagaagttctg
aacggaggcaaagttctggatacatatgatacagaatatggctttcgctggacaggctttgatgcaacatcaggcttttc
actgaatggcgaaaaagtcaaactgaaaggcgttagcatgcatcatgatcaaggctcacttggcgcagttgcaaata
gacgcgcaattgaaagacaagtcgaaatcctgcaaaaaatgggcgtcaatagcattcgcacaacacataatccgg
cagcaaaagcactgattgatgtctgcaatgaaaaaggcgttctggttgtcgaagaagtctttgatatgtggaaccgcag
caaaaatggcaacacggaagattatggcaaatggtttggccaagcaattgcaggcgataatgcagttctgggaggc
gataaagatgaaacatgggcgaaatttgatcttacatcaacaattaaccgcgatagaaatgcaccgtcagttattatgt
ggtcactgggcaatgaaatgatggaaggcatttcaggctcagtttcaggctttccggcaacatcagcaaaactggttgc
atggacaaaagcagcagattcaacaagaccgatgacatatggcgataacaaaattaaagcgaactggaacgaat
caaatacaatgggcgataatctgacagcaaatggcggagttgttggcacaaattattcagatggcgcaaactatgata
aaattcgtacaacacatccgtcatgggcaatttatggctcagaaacagcatcagcgattaatagccgtggcatttataat
agaacaacaggcggagcacaatcatcagataaacagctgacaagctatgataattcagcagttggctggggagca
gttgcatcatcagcatggtatgatgttgttcagagagattttgtcgcaggcacatatgtttggacaggatttgattatctggg
cgaaccgacaccgtggaatggcacaggctcaggcgcagttggctcatggccgtcaccgaaaaatagctattttggca
tcgttgatacagcaggctttccgaaagatacatattatttttatcagagccagtggaatgatgatgttcatacactgcatatt
cttccggcatggaatgaaaatgttgttgcaaaaggctcaggcaataatgttccggttgtcgtttatacagatgcagcgaa
agtgaaactgtattttacaccgaaaggctcaacagaaaaaagactgatcggcgaaaaatcatttacaaaaaaaaca
acagcggcaggctatacatatcaagtctatgaaggcagcgataaagattcaacagcgcataaaaacatgtatctgac
atggaatgttccgtgggcagaaggcacaatttcagcggaagcgtatgatgaaaataatcgcctgattccggaaggca
gcacagaaggcaacgcatcagttacaacaacaggcaaagcagcaaaactgaaagcagatgcggatcgcaaaa
caattacagcggatggcaaagatctgtcatatattgaagtcgatgtcacagatgcaaatggccatattgttccggatgc
agcaaatagagtcacatttgatgttaaaggcgcaggcaaactggttggcgttgataatggctcatcaccggatcatgat
tcatatcaagcggataaccgcaaagcattttcaggcaaagtcctggcaattgttcagtcaacaaaagaagcaggcga
aattacagttacagcaaaagcagatggcctgcaatcaagcacagttaaaattgcaacaacagcagttccgggaaca
agcacagaaaaaacagtccgcagcttttattacagccgcaactattatgtcaaaacaggcaacaaaccgattctgcc
gtcagatgttgaagttcgctattcagatggaacaagcgatagacaaaacgttacatgggatgcagtttcagatgatcaa
attgcaaaagcaggctcattttcagttgcaggcacagttgcaggccaaaaaattagcgttcgcgtcacaatgattgatg
aaattggcgcactg >SEQ ID NO: 11 nucleotide sequence encoding BIF_1068
gttgaagatgcaacaagaagcgatagcacaacacaaatgtcatcaacaccggaagttgtttattcatcagcggtcgat
agcaaacaaaatcgcacaagcgattttgatgcgaactggaaatttatgctgtcagatagcgttcaagcacaagatccg
gcatttgatgattcagcatggcaacaagttgatctgccgcatgattatagcatcacacagaaatatagccaaagcaatg
aagcagaatcagcatatcttccgggaggcacaggctggtatagaaaaagctttacaattgatagagatctggcaggc
aaacgcattgcgattaattttgatggcgtctatatgaatgcaacagtctggtttaatggcgttaaactgggcacacatccg
tatggctattcaccgttttcatttgatctgacaggcaatgcaaaatttggcggagaaaacacaattgtcgtcaaagttgaa
aatagactgccgtcatcaagatggtattcaggcagcggcatttatagagatgttacactgacagttacagatggcgttc
atgttggcaataatggcgtcgcaattaaaacaccgtcactggcaacacaaaatggcggagatgtcacaatgaacctg
acaacaaaagtcgcgaatgatacagaagcagcagcgaacattacactgaaacagacagtttttccgaaaggcgga
aaaacggatgcagcaattggcacagttacaacagcatcaaaatcaattgcagcaggcgcatcagcagatgttacaa
gcacaattacagcagcaagcccgaaactgtggtcaattaaaaacccgaacctgtatacagttagaacagaagttctg
aacggaggcaaagttctggatacatatgatacagaatatggctttcgctggacaggctttgatgcaacatcaggcttttc
actgaatggcgaaaaagtcaaactgaaaggcgttagcatgcatcatgatcaaggctcacttggcgcagttgcaaata
gacgcgcaattgaaagacaagtcgaaatcctgcaaaaaatgggcgtcaatagcattcgcacaacacataatccgg
cagcaaaagcactgattgatgtctgcaatgaaaaaggcgttctggttgtcgaagaagtctttgatatgtggaaccgcag
caaaaatggcaacacggaagattatggcaaatggtttggccaagcaattgcaggcgataatgcagttctgggaggc
gataaagatgaaacatgggcgaaatttgatcttacatcaacaattaaccgcgatagaaatgcaccgtcagttattatgt
ggtcactgggcaatgaaatgatggaaggcatttcaggctcagtttcaggctttccggcaacatcagcaaaactggttgc
atggacaaaagcagcagattcaacaagaccgatgacatatggcgataacaaaattaaagcgaactggaacgaat
caaatacaatgggcgataatctgacagcaaatggcggagttgttggcacaaattattcagatggcgcaaactatgata
aaattcgtacaacacatccgtcatgggcaatttatggctcagaaacagcatcagcgattaatagccgtggcatttataat
agaacaacaggcggagcacaatcatcagataaacagctgacaagctatgataattcagcagttggctggggagca
gttgcatcatcagcatggtatgatgttgttcagagagattttgtcgcaggcacatatgtttggacaggatttgattatctggg
cgaaccgacaccgtggaatggcacaggctcaggcgcagttggctcatggccgtcaccgaaaaatagctattttggca
tcgttgatacagcaggctttccgaaagatacatattatttttatcagagccagtggaatgatgatgttcatacactgcatatt
cttccggcatggaatgaaaatgttgttgcaaaaggctcaggcaataatgttccggttgtcgtttatacagatgcagcgaa
agtgaaactgtattttacaccgaaaggctcaacagaaaaaagactgatcggcgaaaaatcatttacaaaaaaaaca
acagcggcaggctatacatatcaagtctatgaaggcagcgataaagattcaacagcgcataaaaacatgtatctgac
atggaatgttccgtgggcagaaggcacaatttcagcggaagcgtatgatgaaaataatcgcctgattccggaaggca
gcacagaaggcaacgcatcagttacaacaacaggcaaagcagcaaaactgaaagcagatgcggatcgcaaaa
caattacagcggatggcaaagatctgtcatatattgaagtcgatgtcacagatgcaaatggccatattgttccggatgc
agcaaatagagtcacatttgatgttaaaggcgcaggcaaactggttggcgttgataatggctcatcaccggatcatgat
tcatatcaagcggataaccgcaaagcattttcaggcaaagtcctggcaattgttcagtcaacaaaagaagcaggcga
aattacagttacagcaaaagcagatggcctgcaatcaagcacagttaaaattgcaacaacagcagttccgggaaca -continued agcacagaaaaaacagtccgcagcttttattacagccgcaactattatgtcaaaacaggcaacaaaccgattctgcc
gtcagatgttgaagttcgctattcagatggaacaagcgatagacaaaacgttacatgggatgcagtttcagatgatcaa
attgcaaaagcaggctcattttcagttgcaggcacagttgcaggccaaaaaattagcgttcgcgtcacaatgattgatg
aaattggcgcactgctgaattattcagcaagcacaccggttggcacaccggcagttcttccgggatcaagaccggca
gtcctgccggatggcacagtcacatcagcaaattttgcagtccattggacaaaaccggcagatacagtctataataca
gcaggcacagtcaaagtaccgggaacagcaacagthttggcaaagaatttaaagtcacagcgacaattagagttc
aa >SEQ ID NO: 12 nucleotide sequence encoding BIF_1172
gttgaagatgcaacaagaagcgatagcacaacacaaatgtcatcaacaccggaagttgtttattcatcagcggtcgat
agcaaacaaaatcgcacaagcgattttgatgcgaactggaaatttatgctgtcagatagcgttcaagcacaagatccg
gcatttgatgattcagcatggcaacaagttgatctgccgcatgattatagcatcacacagaaatatagccaaagcaatg
aagcagaatcagcatatcttccgggaggcacaggctggtatagaaaaagctttacaattgatagagatctggcaggc
aaacgcattgcgattaattttgatggcgtctatatgaatgcaacagtctggtttaatggcgttaaactgggcacacatccg
tatggctattcaccgttttcatttgatctgacaggcaatgcaaaatttggcggagaaaacacaattgtcgtcaaagttgaa
aatagactgccgtcatcaagatggtattcaggcagcggcatttatagagatgttacactgacagttacagatggcgttc
atgttggcaataatggcgtcgcaattaaaacaccgtcactggcaacacaaaatggcggagatgtcacaatgaacctg
acaacaaaagtcgcgaatgatacagaagcagcagcgaacattacactgaaacagacagtttttccgaaaggcgga
aaaacggatgcagcaattggcacagttacaacagcatcaaaatcaattgcagcaggcgcatcagcagatgttacaa
gcacaattacagcagcaagcccgaaactgtggtcaattaaaaacccgaacctgtatacagttagaacagaagttctg
aacggaggcaaagttctggatacatatgatacagaatatggctttcgctggacaggctttgatgcaacatcaggcttttc
actgaatggcgaaaaagtcaaactgaaaggcgttagcatgcatcatgatcaaggctcacttggcgcagttgcaaata
gacgcgcaattgaaagacaagtcgaaatcctgcaaaaaatgggcgtcaatagcattcgcacaacacataatccgg
cagcaaaagcactgattgatgtctgcaatgaaaaaggcgttctggttgtcgaagaagtctttgatatgtggaaccgcag
caaaaatggcaacacggaagattatggcaaatggtttggccaagcaattgcaggcgataatgcagttctgggaggc
gataaagatgaaacatgggcgaaatttgatcttacatcaacaattaaccgcgatagaaatgcaccgtcagttattatgt
ggtcactgggcaatgaaatgatggaaggcatttcaggctcagtttcaggctttccggcaacatcagcaaaactggttgc
atggacaaaagcagcagattcaacaagaccgatgacatatggcgataacaaaattaaagcgaactggaacgaat
caaatacaatgggcgataatctgacagcaaatggcggagttgttggcacaaattattcagatggcgcaaactatgata
aaattcgtacaacacatccgtcatgggcaatttatggctcagaaacagcatcagcgattaatagccgtggcatttataat
agaacaacaggcggagcacaatcatcagataaacagctgacaagctatgataattcagcagttggctggggagca
gttgcatcatcagcatggtatgatgttgttcagagagattttgtcgcaggcacatatgtttggacaggatttgattatctggg
cgaaccgacaccgtggaatggcacaggctcaggcgcagttggctcatggccgtcaccgaaaaatagctattttggca
tcgttgatacagcaggctttccgaaagatacatattatttttatcagagccagtggaatgatgatgttcatacactgcatatt
cttccggcatggaatgaaaatgttgttgcaaaaggctcaggcaataatgttccggttgtcgtttatacagatgcagcgaa
agtgaaactgtattttacaccgaaaggctcaacagaaaaaagactgatcggcgaaaaatcatttacaaaaaaaaca
acagcggcaggctatacatatcaagtctatgaaggcagcgataaagattcaacagcgcataaaaacatgtatctgac
atggaatgttccgtgggcagaaggcacaatttcagcggaagcgtatgatgaaaataatcgcctgattccggaaggca
gcacagaaggcaacgcatcagttacaacaacaggcaaagcagcaaaactgaaagcagatgcggatcgcaaaa
caattacagcggatggcaaagatctgtcatatattgaagtcgatgtcacagatgcaaatggccatattgttccggatgc
agcaaatagagtcacatttgatgttaaaggcgcaggcaaactggttggcgttgataatggctcatcaccggatcatgat
tcatatcaagcggataaccgcaaagcattttcaggcaaagtcctggcaattgttcagtcaacaaaagaagcaggcga
aattacagttacagcaaaagcagatggcctgcaatcaagcacagttaaaattgcaacaacagcagttccgggaaca
agcacagaaaaaacagtccgcagcttttattacagccgcaactattatgtcaaaacaggcaacaaaccgattctgcc
gtcagatgttgaagttcgctattcagatggaacaagcgatagacaaaacgttacatgggatgcagtttcagatgatcaa
attgcaaaagcaggctcattttcagttgcaggcacagttgcaggccaaaaaattagcgttcgcgtcacaatgattgatg
aaattggcgcactgctgaattattcagcaagcacaccggttggcacaccggcagttcttccgggatcaagaccggca
gtcctgccggatggcacagtcacatcagcaaattttgcagtccattggacaaaaccggcagatacagtctataataca
gcaggcacagtcaaagtaccgggaacagcaacagthttggcaaagaatttaaagtcacagcgacaattagagttc
aaagaagccaagttacaattggctcatcagtttcaggaaatgcactgagactgacacaaaatattccggcagataaa
caatcagatacactggatgcgattaaagatggctcaacaacagttgatgcaaatacaggcggaggcgcaaatccgt
cagcatggacaaattgggcatattcaaaagcaggccataacacagcggaaattacatttgaatatgcgacagaaca
acaactgggccagatcgtcatgtatttttttcgcgatagcaatgcagttagatttccggatgctggcaaaacaaaaattca
gatc >SEQ ID NO: 13 nucleotide sequence encoding BIF_1241
gttgaagatgcaacaagaagcgatagcacaacacaaatgtcatcaacaccggaagttgtttattcatcagcggtcgat
agcaaacaaaatcgcacaagcgattttgatgcgaactggaaatttatgctgtcagatagcgttcaagcacaagatccg
gcatttgatgattcagcatggcaacaagttgatctgccgcatgattatagcatcacacagaaatatagccaaagcaatg
aagcagaatcagcatatcttccgggaggcacaggctggtatagaaaaagctttacaattgatagagatctggcaggc
aaacgcattgcgattaattttgatggcgtctatatgaatgcaacagtctggtttaatggcgttaaactgggcacacatccg
tatggctattcaccgttttcatttgatctgacaggcaatgcaaaatttggcggagaaaacacaattgtcgtcaaagttgaa
aatagactgccgtcatcaagatggtattcaggcagcggcatttatagagatgttacactgacagttacagatggcgttc
atgttggcaataatggcgtcgcaattaaaacaccgtcactggcaacacaaaatggcggagatgtcacaatgaacctg
acaacaaaagtcgcgaatgatacagaagcagcagcgaacattacactgaaacagacagtttttccgaaaggcgga
aaaacggatgcagcaattggcacagttacaacagcatcaaaatcaattgcagcaggcgcatcagcagatgttacaa
gcacaattacagcagcaagcccgaaactgtggtcaattaaaaacccgaacctgtatacagttagaacagaagttctg
aacggaggcaaagttctggatacatatgatacagaatatggctttcgctggacaggctttgatgcaacatcaggcttttc
actgaatggcgaaaaagtcaaactgaaaggcgttagcatgcatcatgatcaaggctcacttggcgcagttgcaaata
gacgcgcaattgaaagacaagtcgaaatcctgcaaaaaatgggcgtcaatagcattcgcacaacacataatccgg
cagcaaaagcactgattgatgtctgcaatgaaaaaggcgttctggttgtcgaagaagtctttgatatgtggaaccgcag
caaaaatggcaacacggaagattatggcaaatggtttggccaagcaattgcaggcgataatgcagttctgggaggc
gataaagatgaaacatgggcgaaatttgatcttacatcaacaattaaccgcgatagaaatgcaccgtcagttattatgt
ggtcactgggcaatgaaatgatggaaggcatttcaggctcagtttcaggctttccggcaacatcagcaaaactggttgc
atggacaaaagcagcagattcaacaagaccgatgacatatggcgataacaaaattaaagcgaactggaacgaat
caaatacaatgggcgataatctgacagcaaatggcggagttgttggcacaaattattcagatggcgcaaactatgata
aaattcgtacaacacatccgtcatgggcaatttatggctcagaaacagcatcagcgattaatagccgtggcatttataat
agaacaacaggcggagcacaatcatcagataaacagctgacaagctatgataattcagcagttggctggggagca
gttgcatcatcagcatggtatgatgttgttcagagagattttgtcgcaggcacatatgtttggacaggatttgattatctggg
cgaaccgacaccgtggaatggcacaggctcaggcgcagttggctcatggccgtcaccgaaaaatagctattttggca
tcgttgatacagcaggctttccgaaagatacatattatttttatcagagccagtggaatgatgatgttcatacactgcatatt -continued cttccggcatggaatgaaaatgttgttgcaaaaggctcaggcaataatgttccggttgtcgtttatacagatgcagcgaa
agtgaaactgtattttacaccgaaaggctcaacagaaaaaagactgatcggcgaaaaatcatttacaaaaaaaaca
acagcggcaggctatacatatcaagtctatgaaggcagcgataaagattcaacagcgcataaaaacatgtatctgac
atggaatgttccgtgggcagaaggcacaatttcagcggaagcgtatgatgaaaataatcgcctgattccggaaggca
gcacagaaggcaacgcatcagttacaacaacaggcaaagcagcaaaactgaaagcagatgcggatcgcaaaa
caattacagcggatggcaaagatctgtcatatattgaagtcgatgtcacagatgcaaatggccatattgttccggatgc
agcaaatagagtcacatttgatgttaaaggcgcaggcaaactggttggcgttgataatggctcatcaccggatcatgat
tcatatcaagcggataaccgcaaagcattttcaggcaaagtcctggcaattgttcagtcaacaaaagaagcaggcga
aattacagttacagcaaaagcagatggcctgcaatcaagcacagttaaaattgcaacaacagcagttccgggaaca
agcacagaaaaaacagtccgcagcttttattacagccgcaactattatgtcaaaacaggcaacaaaccgattctgcc
gtcagatgttgaagttcgctattcagatggaacaagcgatagacaaaacgttacatgggatgcagtttcagatgatcaa
attgcaaaagcaggctcattttcagttgcaggcacagttgcaggccaaaaaattagcgttcgcgtcacaatgattgatg
aaattggcgcactgctgaattattcagcaagcacaccggttggcacaccggcagttcttccgggatcaagaccggca
gtcctgccggatggcacagtcacatcagcaaattttgcagtccattggacaaaaccggcagatacagtctataataca
gcaggcacagtcaaagtaccgggaacagcaacagthttggcaaagaatttaaagtcacagcgacaattagagttc
aaagaagccaagttacaattggctcatcagtttcaggaaatgcactgagactgacacaaaatattccggcagataaa
caatcagatacactggatgcgattaaagatggctcaacaacagttgatgcaaatacaggcggaggcgcaaatccgt
cagcatggacaaattgggcatattcaaaagcaggccataacacagcggaaattacatttgaatatgcgacagaaca
acaactgggccagatcgtcatgtatttttttcgcgatagcaatgcagttagatttccggatgctggcaaaacaaaaattca
gatcagcgcagatggcaaaaattggacagatctggcagcaacagaaacaattgcagcgcaagaatcaagcgata
gagtcaaaccgtatacatatgattttgcaccggttggcgcaacatttgttaaagtgacagtcacaaacgcagatacaac
aacaccgtcaggcgttgthgcgcaggcctgacagaaattgaactgaaaacagcgaca >SEQ ID NO: 14 nucleotide sequence encoding BIF_1326
gttgaagatgcaacaagaagcgatagcacaacacaaatgtcatcaacaccggaagttgtttattcatcagcggtcgat
agcaaacaaaatcgcacaagcgattttgatgcgaactggaaatttatgctgtcagatagcgttcaagcacaagatccg
gcatttgatgattcagcatggcaacaagttgatctgccgcatgattatagcatcacacagaaatatagccaaagcaatg
aagcagaatcagcatatcttccgggaggcacaggctggtatagaaaaagctttacaattgatagagatctggcaggc
aaacgcattgcgattaattttgatggcgtctatatgaatgcaacagtctggtttaatggcgttaaactgggcacacatccg
tatggctattcaccgttttcatttgatctgacaggcaatgcaaaatttggcggagaaaacacaattgtcgtcaaagttgaa
aatagactgccgtcatcaagatggtattcaggcagcggcatttatagagatgttacactgacagttacagatggcgttc
atgttggcaataatggcgtcgcaattaaaacaccgtcactggcaacacaaaatggcggagatgtcacaatgaacctg
acaacaaaagtcgcgaatgatacagaagcagcagcgaacattacactgaaacagacagtttttccgaaaggcgga
aaaacggatgcagcaattggcacagttacaacagcatcaaaatcaattgcagcaggcgcatcagcagatgttacaa
gcacaattacagcagcaagcccgaaactgtggtcaattaaaaacccgaacctgtatacagttagaacagaagttctg
aacggaggcaaagttctggatacatatgatacagaatatggctttcgctggacaggctttgatgcaacatcaggcttttc
actgaatggcgaaaaagtcaaactgaaaggcgttagcatgcatcatgatcaaggctcacttggcgcagttgcaaata
gacgcgcaattgaaagacaagtcgaaatcctgcaaaaaatgggcgtcaatagcattcgcacaacacataatccgg
cagcaaaagcactgattgatgtctgcaatgaaaaaggcgttctggttgtcgaagaagtctttgatatgtggaaccgcag
caaaaatggcaacacggaagattatggcaaatggtttggccaagcaattgcaggcgataatgcagttctgggaggc
gataaagatgaaacatgggcgaaatttgatcttacatcaacaattaaccgcgatagaaatgcaccgtcagttattatgt
ggtcactgggcaatgaaatgatggaaggcatttcaggctcagtttcaggctttccggcaacatcagcaaaactggttgc
atggacaaaagcagcagattcaacaagaccgatgacatatggcgataacaaaattaaagcgaactggaacgaat
caaatacaatgggcgataatctgacagcaaatggcggagttgttggcacaaattattcagatggcgcaaactatgata
aaattcgtacaacacatccgtcatgggcaatttatggctcagaaacagcatcagcgattaatagccgtggcatttataat
agaacaacaggcggagcacaatcatcagataaacagctgacaagctatgataattcagcagttggctggggagca
gttgcatcatcagcatggtatgatgttgttcagagagattttgtcgcaggcacatatgtttggacaggatttgattatctggg
cgaaccgacaccgtggaatggcacaggctcaggcgcagttggctcatggccgtcaccgaaaaatagctattttggca
tcgttgatacagcaggctttccgaaagatacatattatttttatcagagccagtggaatgatgatgttcatacactgcatatt
cttccggcatggaatgaaaatgttgttgcaaaaggctcaggcaataatgttccggttgtcgtttatacagatgcagcgaa
agtgaaactgtattttacaccgaaaggctcaacagaaaaaagactgatcggcgaaaaatcatttacaaaaaaaaca
acagcggcaggctatacatatcaagtctatgaaggcagcgataaagattcaacagcgcataaaaacatgtatctgac
atggaatgttccgtgggcagaaggcacaatttcagcggaagcgtatgatgaaaataatcgcctgattccggaaggca
gcacagaaggcaacgcatcagttacaacaacaggcaaagcagcaaaactgaaagcagatgcggatcgcaaaa
caattacagcggatggcaaagatctgtcatatattgaagtcgatgtcacagatgcaaatggccatattgttccggatgc
agcaaatagagtcacatttgatgttaaaggcgcaggcaaactggttggcgttgataatggctcatcaccggatcatgat
tcatatcaagcggataaccgcaaagcattttcaggcaaagtcctggcaattgttcagtcaacaaaagaagcaggcga
aattacagttacagcaaaagcagatggcctgcaatcaagcacagttaaaattgcaacaacagcagttccgggaaca
agcacagaaaaaacagtccgcagcttttattacagccgcaactattatgtcaaaacaggcaacaaaccgattctgcc
gtcagatgttgaagttcgctattcagatggaacaagcgatagacaaaacgttacatgggatgcagtttcagatgatcaa
attgcaaaagcaggctcattttcagttgcaggcacagttgcaggccaaaaaattagcgttcgcgtcacaatgattgatg
aaattggcgcactgctgaattattcagcaagcacaccggttggcacaccggcagttcttccgggatcaagaccggca
gtcctgccggatggcacagtcacatcagcaaattttgcagtccattggacaaaaccggcagatacagtctataataca
gcaggcacagtcaaagtaccgggaacagcaacagthttggcaaagaatttaaagtcacagcgacaattagagttc
aaagaagccaagttacaattggctcatcagtttcaggaaatgcactgagactgacacaaaatattccggcagataaa
caatcagatacactggatgcgattaaagatggctcaacaacagttgatgcaaatacaggcggaggcgcaaatccgt
cagcatggacaaattgggcatattcaaaagcaggccataacacagcggaaattacatttgaatatgcgacagaaca
acaactgggccagatcgtcatgtatttttttcgcgatagcaatgcagttagatttccggatgctggcaaaacaaaaattca
gatcagcgcagatggcaaaaattggacagatctggcagcaacagaaacaattgcagcgcaagaatcaagcgata
gagtcaaaccgtatacatatgattttgcaccggttggcgcaacatttgttaaagtgacagtcacaaacgcagatacaac
aacaccgtcaggcgttgthgcgcaggcctgacagaaattgaactgaaaacagcgacaagcaaatttgtcacaaata
catcagcagcactgtcatcacttacagtcaatggcacaaaagtttcagattcagttctggcagcaggctcatataacac
accggcaattatcgcagatgttaaagcggaaggcgaaggcaatgcaagcgttacagtccttccggcacatgataatg
ttattcgcgtcattacagaaagcgaagatcatgtcacacgcaaaacatttacaatcaacctgggcacagaacaagaa
ttt >SEQ ID NO: 15 forward primer for generation of BIF variants
GGGGTAACTAGTGGAAGATGCAACAAGAAG >SEQ ID NO: 16 reverse primer for BIF917
GCGCTTAATTAATTATGTTTTTCTGTGCTTGTTC -continued >SEQ ID NO: 17 reverse primer for BIF995
GCGCTTAATTAATTACAGTGCGCCAATTTCATCAATCA >SEQ ID NO: 18 reverse primer for BIF1068
GCGCTTAATTAATTATTGAACTCTAATTGTCGCTG >SEQ ID NO: 19 reverse primer for BIF1241
GCGCTTAATTAATTATGTCGCTGTTTTCAGTTCAAT >SEQ ID NO: 20 reverse primer for BIF1326
GCGCTTAATTAATTAAAATTCTTGTTCTGTGCCCA >SEQ ID NO: 21 reverse primer for BIF1478
GCGCTTAATTAATTATCTCAGTCTAATTTCGCTTGCGC >SEQ ID NO: 22 *Bifidobacterium bifidum* BIF1750
vedatrsdsttqmsstpevvyssavdskqnrtsdfdanwkfmlsdsvqaqdpafddsawqqvdlphdysitqkys
qsneaesaylpggtgwyrksftidrdlagkriainfdgvymnatvwfngvklgthpygyspfsfdltgnakfggentivv
kvenrlpssrwysgsgiyrdvtltvtdgvhvgnngvaiktpslatqnggdytmnlttkvandteaaanitlkqtvfpkggk
tdaaigtvttasksiaagasadvtstitaaspklwsiknpnlytvrtevlnggkvldtydteygfrwtgfdatsgfslngekv
klkgvsmhhdqgslgavanrraierqveilqkmgvnsirtthnpaakalidvcnekgvlvveevfdmwnrskngnte
dygkwfgqaiagdnavlggdkdetwakfdltstinrdrnapsvimwslgnemmegisgsysgfpatsaklvawtka
adstrpmtygdnkikanwnesntmgdnltanggvvgtnysdganydkirtthpswaiygsetasainsrgiynrttgg
aqssdkqltsydnsavgwgavassawydvvqrdfvagtyvwtgfdylgeptpwngtgsgavgswpspknsyfgiv
dtagfpkdtyyfyqsqwnddvhtlhilpawnenvvakgsgnnvpvvvytdaakvklyftpkgstekrligeksftkktta
agytyqvyegsdkdstahknmyltwnvpwaegtisaeaydennrlipegstegnasytttgkaaklkadadrktitad
gkdlsyievdvtdanghivpdaanrvtfdvkgagklvgvdngsspdhdsyqadnrkafsgkvlaivqstkeageitvt
akadglqsstvkiattavpgtstektvrsfyysrnyyvktgnkpilpsdvevrysdgtsdrqnvtwdaysddqiakagsf
svagtvagqkisvrvtmideigallnysastpvgtpavlpgsrpavlpdgtvtsanfavhwtkpadtvyntagtvkvpgt
atvfgkefkvtatirvqrsqvtigssysgnalrltqnipadkqsdtldaikdgsttvdantggganpsawtnwayskagh
ntaeitfeyateqqlgqivmyffrdsnavrfpdagktkiqisadgknwtdlaatetiaaqessdrvkpytydfapvgatfv
kvtvtnadtttpsgvvcaglteielktatskfvtntsaalssltvngtkvsdsvlaagsyntpaiiadvkaegegnasvtvlp
andnvirvitesedhvtrktftinlgteqefpadsderdypaadmtvtvgseqtsgtategpkkfavdgntstywhsnwt
pttyndlwiafelqkptkldalrylprpagskngsvteykvqvsddgtnwtdagsgtwttdygwklaefnqpvttkhvrlk
avhtyadsgndkfmsaseirlrkavdttdisgatvtvpakltvdrvdadhpatfatkdvtvtlgdatlrygvdylldyagnt
avgkatvtvrgidkysgtvaktftielknapapeptltsysyktkpskltyvvgdafdpaglvlqhdrqadrppqplvgeq
adergltcgtrcdrveqlrkhenreahrtgldhlefvgaadgavgeqatfkvhvhadqgdgrhddaderdidphypvd
havgelaraachhviglrvdthrlkasgfqipaddmaeidritgfhrferhvg >SEQ ID NO: 23 The signal sequence of extracellular lactase from *Bifidobacterium bifidum* DSM20215
Vrskklwisllfalaliftmafgstssaqa

The invention claimed is:

1. A spray-dried composition comprising a polypeptide which is a β-galactosidase having transgalactosylating activity wherein the composition comprises:

15-25 wt % maltodextrin, 10-20 wt % sodium chloride, and 0.1 wt % or less polyol, wherein the spray-dried particles have a volume mean diameter of 50-70 μm, wherein the polypeptide has a ratio of transgalactosylating activity to β-galactosidase activity of at least 4 at an initial lactose concentration of 3% w/w, wherein the composition retains at least 80% of its initial transgalactosylating activity after 12 months of storage at 25° C., and wherein, when the composition is incubated with a lactose-containing milk-based substrate comprising 5% w/w lactose at 37° C. and an enzyme concentration of 100 ppm for 3 hours, the composition produces galacto-oligosaccharides without detectable formation of galactosyl-glycerol.

2. The composition of claim 1, wherein the polypeptide having a transgalactosylating activity is selected from the group consisting of:

a. a polypeptide comprising an amino acid sequence having at least 90% sequence identity with SEQ ID NO: 1, wherein said polypeptide consists of at most 980 amino acid residues, b. a polypeptide comprising an amino acid sequence having at least 97% sequence identity with SEQ ID NO: 2, wherein said polypeptide consists of at most 975 amino acid residues, c. a polypeptide comprising an amino acid sequence having at least 96.5% sequence identity with SEQ ID NO: 3, wherein said polypeptide consists of at most 1300 amino acid residues, d. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4 or 5; or ii) the complementary strand of i), e. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and f. a polypeptide comprising a deletion, insertion and/or conservative substitution of one or more amino acid residues of SEQ ID NO: 1, 2, 3, 4 or 5.

3. The composition of claim 2, wherein the polypeptide having transgalactosylating activity is selected from the group consisting of:

a. a polypeptide comprising an amino acid sequence having at least 96.5% sequence identity with SEQ ID NO: 3, wherein said polypeptide consists of at most 1300 amino acid residues, b. a polypeptide comprising an amino acid sequence having at least 90% sequence identity with SEQ ID NO: 1, wherein said polypeptide consists of at most 980 amino acid residues, c. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4, or 5; or ii) the complementary strand of i), d. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and e. a polypeptide comprising a deletion, insertion and/or conservative substitution of one or more amino acid residues of SEQ ID NO: 1, 2, 3, 4 or 5.

4. The composition of claim 3, wherein the polypeptide having transgalactosylating activity comprises the amino acid sequence of SEQ ID NO:1, 2, 3, 4 or 5.

5. The composition of claim 1, wherein the composition further contains potato starch.

* * * * *

SEQUENCE LISTING

Sequence total quantity: 23
SEQ ID NO: 1 moltype = AA length = 887
FEATURE Location/Qualifiers
REGION 1..887
note = Truncated lactase fragment
source 1..887
mol_type = protein
organism = synthetic construct
SEQUENCE: 1
VEDATRSDST TQMSSTPEVV YSSAVDSKQN RTSDFDANWK FMLSDSVQAQ DPAFDDSAWQ 60
QVDLPHDYSI TQKYSQSNEA ESAYLPGGTG WYRKSFTIDR DLAGKRIAIN FDGVYMNATV 120
WFNGVKLGTH PYGYSPFSFD LTGNAKFGGE NTIVVKVENR LPSSRWYSGS GIYRDVTLTV 180
TDGVHVGNNG VAIKTPSLAT QNGGDVTMNL TTKVANDTEA AANITLKQTV FPKGGKTDAA 240
IGTVTTASKS IAAGASADVT STITAASPKL WSIKNPNLYT VRTEVLNGGK VLDTYDTEYG 300
FRWTGFDATS GFSLNGEKVK LKGVSMHHDQ GSLGAVANRR AIERQVEILQ KMGVNSIRTT 360
HNPAAKALID VCNEKGVLVV EEVFDMWNRS KNGNTEDYGK WFGQAIAGDN AVLGGDKDET 420
WAKFDLTSTI NRDRNAPSVI MWSLGNEMME GISGSVSGFP ATSAKLVAWT KAADSTRPMT 480
YGDNKIKANW NESNTMGDNL TANGGVVGTN YSDGANYDKI RTTHPSWAIY GSETASAINS 540
RGIYNRTTGG AQSSDKQLTS YDNSAVGWGA VASSAWYDVV QRDFVAGTYV WTGFDYLGEP 600
TPWNGTGSGA VGSWPSPKNS YFGIVDTAGF PKDTYYFYQS QWNDDVHTLH ILPAWNENVV 660
AKGSGNNVPV VVYTDAAKVK LYFTPKGSTE KRLIGEKSFT KKTTAAGYTY QVYEGSDKDS 720
TAHKNMYLTW NVPWAEGTIS AEAYDENNRL IPEGSTEGNA SVTTTGKAAK LKADADRKTI 780
TADGKDLSYI EVDVTDANGH IVPDAANRVT FDVKGAGKLV GVDNGSSPDH DSYQADNRKA 840
FSGKVLAIVQ STKEAGEITV TAKADGLQSS TVKIATTAVP GTSTEKT 887

SEQ ID NO: 2 moltype = AA length = 965
FEATURE Location/Qualifiers
REGION 1..965
note = Truncated lactase fragment
source 1..965
mol_type = protein -continued

```
                       organism = synthetic construct
SEQUENCE: 2
VEDATRSDST TQMSSTPEVV YSSAVDSKQN RTSDFDANWK FMLSDSVQAQ DPAFDDSAWQ  60
QVDLPHDYSI TQKYSQSNEA ESAYLPGGTG WYRKSFTIDR DLAGKRIAIN FDGVYMNATV  120
WFNGVKLGTH PYGYSPFSFD LTGNAKFGGE NTIVVKVENR LPSSRWYSGS GIYRDVTLTV  180
TDGVHVGNNG VAIKTPSLAT QNGGDVTMNL TTKVANDTEA AANITLKQTV FPKGGKTDAA  240
IGTVTTASKS IAAGASADVT STITAASPKL WSIKNPNLYT VRTEVLNGGK VLDTYDTEYG  300
FRWTGFDATS GFSLNGEKVK LKGVSMHHDQ GSLGAVANRR AIERQVEILQ KMGVNSIRTT  360
HNPAAKALID VCNEKGVLVV EEVFDMWNRS KNGNTEDYGK WFGQAIAGDN AVLGGDKDET  420
WAKFDLTSTI NRDRNAPSVI MWSLGNEMME GISGSVSGFP ATSAKLVAWT KAADSTRPMT  480
YGDNKIKANW NESNTMGDNL TANGGVVGTN YSDGANYDKI RTTHPSWAIY GSETASAINS  540
RGIYNRTTGG AQSSDKQLTS YDNSAVGWGA VASSAWYDVV QRDFVAGTYV WTGFDYLGEP  600
TPWNGTGSGA VGSWPSPKNS YFGIVDTAGF PKDTYYFYQS QWNDDVHTLH ILPAWNENVV  660
AKGSGNNVPV VVYTDAAKVK LYFTPKGSTE KRLIGEKSFT KKTTAAGYTY QVYEGSDKDS  720
TAHKNMYLTW NVPWAEGTIS AEAYDENNRL IPEGSTEGNA SVTTTGKAAK LKADADRKTI  780
TADGKDLSYI EVDVTDANGH IVPDAANRVT FDVKGAGKLV GVDNGSSPDH DSYQADNRKA  840
FSGKVLAIVQ STKEAGEITV TAKADGLQSS TVKIATTAVP GTSTEKTVRS FYYSRNYYVK  900
TGNKPILPSD VEVRYSDGTS DRQNVTWDAV SDDQIAKAGS FSVAGTVAGQ KISVRVTMID  960
EIGAL                                                              965

SEQ ID NO: 3           moltype = AA  length = 1038
FEATURE                Location/Qualifiers
REGION                 1..1038
                       note = Truncated lactase fragment
source                 1..1038
                       mol_type = protein
                       organism = synthetic construct
SEQUENCE: 3
VEDATRSDST TQMSSTPEVV YSSAVDSKQN RTSDFDANWK FMLSDSVQAQ DPAFDDSAWQ  60
QVDLPHDYSI TQKYSQSNEA ESAYLPGGTG WYRKSFTIDR DLAGKRIAIN FDGVYMNATV  120
WFNGVKLGTH PYGYSPFSFD LTGNAKFGGE NTIVVKVENR LPSSRWYSGS GIYRDVTLTV  180
TDGVHVGNNG VAIKTPSLAT QNGGDVTMNL TTKVANDTEA AANITLKQTV FPKGGKTDAA  240
IGTVTTASKS IAAGASADVT STITAASPKL WSIKNPNLYT VRTEVLNGGK VLDTYDTEYG  300
FRWTGFDATS GFSLNGEKVK LKGVSMHHDQ GSLGAVANRR AIERQVEILQ KMGVNSIRTT  360
HNPAAKALID VCNEKGVLVV EEVFDMWNRS KNGNTEDYGK WFGQAIAGDN AVLGGDKDET  420
WAKFDLTSTI NRDRNAPSVI MWSLGNEMME GISGSVSGFP ATSAKLVAWT KAADSTRPMT  480
YGDNKIKANW NESNTMGDNL TANGGVVGTN YSDGANYDKI RTTHPSWAIY GSETASAINS  540
RGIYNRTTGG AQSSDKQLTS YDNSAVGWGA VASSAWYDVV QRDFVAGTYV WTGFDYLGEP  600
TPWNGTGSGA VGSWPSPKNS YFGIVDTAGF PKDTYYFYQS QWNDDVHTLH ILPAWNENVV  660
AKGSGNNVPV VVYTDAAKVK LYFTPKGSTE KRLIGEKSFT KKTTAAGYTY QVYEGSDKDS  720
TAHKNMYLTW NVPWAEGTIS AEAYDENNRL IPEGSTEGNA SVTTTGKAAK LKADADRKTI  780
TADGKDLSYI EVDVTDANGH IVPDAANRVT FDVKGAGKLV GVDNGSSPDH DSYQADNRKA  840
FSGKVLAIVQ STKEAGEITV TAKADGLQSS TVKIATTAVP GTSTEKTVRS FYYSRNYYVK  900
TGNKPILPSD VEVRYSDGTS DRQNVTWDAV SDDQIAKAGS FSVAGTVAGQ KISVRVTMID  960
EIGALLNYSA STPVGTPAVL PGSRPAVLPD GTVTSANFAV HWTKPADTVY NTAGTVKVPG  1020
TATVFGKEFK VTATIRVQ                                                1038

SEQ ID NO: 4           moltype = AA  length = 1142
FEATURE                Location/Qualifiers
REGION                 1..1142
                       note = Truncated lactase fragment
source                 1..1142
                       mol_type = protein
                       organism = synthetic construct
SEQUENCE: 4
VEDATRSDST TQMSSTPEVV YSSAVDSKQN RTSDFDANWK FMLSDSVQAQ DPAFDDSAWQ  60
QVDLPHDYSI TQKYSQSNEA ESAYLPGGTG WYRKSFTIDR DLAGKRIAIN FDGVYMNATV  120
WFNGVKLGTH PYGYSPFSFD LTGNAKFGGE NTIVVKVENR LPSSRWYSGS GIYRDVTLTV  180
TDGVHVGNNG VAIKTPSLAT QNGGDVTMNL TTKVANDTEA AANITLKQTV FPKGGKTDAA  240
IGTVTTASKS IAAGASADVT STITAASPKL WSIKNPNLYT VRTEVLNGGK VLDTYDTEYG  300
FRWTGFDATS GFSLNGEKVK LKGVSMHHDQ GSLGAVANRR AIERQVEILQ KMGVNSIRTT  360
HNPAAKALID VCNEKGVLVV EEVFDMWNRS KNGNTEDYGK WFGQAIAGDN AVLGGDKDET  420
WAKFDLTSTI NRDRNAPSVI MWSLGNEMME GISGSVSGFP ATSAKLVAWT KAADSTRPMT  480
YGDNKIKANW NESNTMGDNL TANGGVVGTN YSDGANYDKI RTTHPSWAIY GSETASAINS  540
RGIYNRTTGG AQSSDKQLTS YDNSAVGWGA VASSAWYDVV QRDFVAGTYV WTGFDYLGEP  600
TPWNGTGSGA VGSWPSPKNS YFGIVDTAGF PKDTYYFYQS QWNDDVHTLH ILPAWNENVV  660
AKGSGNNVPV VVYTDAAKVK LYFTPKGSTE KRLIGEKSFT KKTTAAGYTY QVYEGSDKDS  720
TAHKNMYLTW NVPWAEGTIS AEAYDENNRL IPEGSTEGNA SVTTTGKAAK LKADADRKTI  780
TADGKDLSYI EVDVTDANGH IVPDAANRVT FDVKGAGKLV GVDNGSSPDH DSYQADNRKA  840
FSGKVLAIVQ STKEAGEITV TAKADGLQSS TVKIATTAVP GTSTEKTVRS FYYSRNYYVK  900
TGNKPILPSD VEVRYSDGTS DRQNVTWDAV SDDQIAKAGS FSVAGTVAGQ KISVRVTMID  960
EIGALLNYSA STPVGTPAVL PGSRPAVLPD GTVTSANFAV HWTKPADTVY NTAGTVKVPG  1020
TATVFGKEFK VTATIRVQRS QVTIGSSVSG NALRLTQNIP ADKQSDTLDA IKDGSTTVDA  1080
NTGGGANPSA WTNWAYSKAG HNTAEITFEY ATEQQLGQIV MYFFRDSNAV RFPDAGKTKI  1140
QI                                                                 1142

SEQ ID NO: 5           moltype = AA  length = 1211
FEATURE                Location/Qualifiers
REGION                 1..1211
```

```
                         note = Truncated lactase fragment
source                   1..1211
                         mol_type = protein
                         organism = synthetic construct
SEQUENCE: 5
VEDATRSDST TQMSSTPEVV YSSAVDSKQN RTSDFDANWK FMLSDSVQAQ DPAFDDSAWQ  60
QVDLPHDYSI TQKYSQSNEA ESAYLPGGTG WYRKSFTIDR DLAGKRIAIN FDGVYMNATV  120
WFNGVKLGTH PYGYSPFSFD LTGNAKFGGE NTIVVKVENR LPSSRWYSGS GIYRDVTLTV  180
TDGVHVGNNG VAIKTPSLAT QNGGDVTMNL TTKVANDTEA AANITLKQTV FPKGGKTDAA  240
IGTVTTASKS IAAGASADVT STITAASPKL WSIKNPNLYT VRTEVLNGGK VLDTYDTEYG  300
FRWTGFDATS GFSLNGEKVK LKGVSMHHDQ GSLGAVANRR AIERQVEILQ KMGVNSIRTT  360
HNPAAKALID VCNEKGVLVV EEVFDMWNRS KNGNTEDYGK WFGQAIAGDN AVLGGDKDET  420
WAKFDLTSTI NRDRNAPSVI MWSLGNEMME GISGSVSGFP ATSAKLVAWT KAADSTRPMT  480
YGDNKIKANW NESNTMGDNL TANGGVVGTN YSDGANYDKI RTTHPSWAIY GSETASAINS  540
RGIYNRTTGG AQSSDKQLTS YDNSAVGWGA VASSAWYDVV QRDFVAGTYV WTGFDYLGEP  600
TPWNGTGSGA VGSWPSPKNS YFGIVDTAGF PKDTYYFYQS QWNDDVHTLH ILPAWNENVV  660
AKGSGNNVPV VVYTDAAKVK LYFTPKGSTE KRLIGEKSFT KKTTAAGYTY QVYEGSDKDS  720
TAHKNMYLTW NVPWAEGTIS AEAYDENNRL IPEGSTEGNA SVTTTGKAAK LKADADRKTI  780
TADGKDLSYI EVDVTDANGH IVPDAANRVT FDVKGAGKLV GVDNGSSPDH DSYQADNRKA  840
FSGKVLAIVQ STKEAGEITV TAKADGLQSS TVKIATTAVP GTSTEKTVRS FYYSRNYYVK  900
TGNKPILPSD VEVRYSDGTS DRQNVTWDAV SDDQIAKAGS FSVAGTVAGQ KISVRVTMID  960
EIGALLNYSA STPVGTPAVL PGSRPAVLPD GTVTSANFAV HWTKPADTVY NTAGTVKVPG  1020
TATVFGKEFK VTATIRVQRS QVTIGSSVSG NALRLTQNIP ADKQSDTLDA IKDGSTTVDA  1080
NTGGGANPSA WTNWAYSKAG HNTAEITFEY ATEQQLGQIV MYFFRDSNAV RFPDAGKTKI  1140
QISADGKNWT DLAATETIAA QESSDRVKPY TYDFAPVGAT FVKVTVTNAD TTTPSGVVCA  1200
GLTEIELKTA T                                                    1211

SEQ ID NO: 6             moltype = AA  length = 1296
FEATURE                  Location/Qualifiers
REGION                   1..1296
                         note = Truncated lactase fragment
source                   1..1296
                         mol_type = protein
                         organism = synthetic construct
SEQUENCE: 6
VEDATRSDST TQMSSTPEVV YSSAVDSKQN RTSDFDANWK FMLSDSVQAQ DPAFDDSAWQ  60
QVDLPHDYSI TQKYSQSNEA ESAYLPGGTG WYRKSFTIDR DLAGKRIAIN FDGVYMNATV  120
WFNGVKLGTH PYGYSPFSFD LTGNAKFGGE NTIVVKVENR LPSSRWYSGS GIYRDVTLTV  180
TDGVHVGNNG VAIKTPSLAT QNGGDVTMNL TTKVANDTEA AANITLKQTV FPKGGKTDAA  240
IGTVTTASKS IAAGASADVT STITAASPKL WSIKNPNLYT VRTEVLNGGK VLDTYDTEYG  300
FRWTGFDATS GFSLNGEKVK LKGVSMHHDQ GSLGAVANRR AIERQVEILQ KMGVNSIRTT  360
HNPAAKALID VCNEKGVLVV EEVFDMWNRS KNGNTEDYGK WFGQAIAGDN AVLGGDKDET  420
WAKFDLTSTI NRDRNAPSVI MWSLGNEMME GISGSVSGFP ATSAKLVAWT KAADSTRPMT  480
YGDNKIKANW NESNTMGDNL TANGGVVGTN YSDGANYDKI RTTHPSWAIY GSETASAINS  540
RGIYNRTTGG AQSSDKQLTS YDNSAVGWGA VASSAWYDVV QRDFVAGTYV WTGFDYLGEP  600
TPWNGTGSGA VGSWPSPKNS YFGIVDTAGF PKDTYYFYQS QWNDDVHTLH ILPAWNENVV  660
AKGSGNNVPV VVYTDAAKVK LYFTPKGSTE KRLIGEKSFT KKTTAAGYTY QVYEGSDKDS  720
TAHKNMYLTW NVPWAEGTIS AEAYDENNRL IPEGSTEGNA SVTTTGKAAK LKADADRKTI  780
TADGKDLSYI EVDVTDANGH IVPDAANRVT FDVKGAGKLV GVDNGSSPDH DSYQADNRKA  840
FSGKVLAIVQ STKEAGEITV TAKADGLQSS TVKIATTAVP GTSTEKTVRS FYYSRNYYVK  900
TGNKPILPSD VEVRYSDGTS DRQNVTWDAV SDDQIAKAGS FSVAGTVAGQ KISVRVTMID  960
EIGALLNYSA STPVGTPAVL PGSRPAVLPD GTVTSANFAV HWTKPADTVY NTAGTVKVPG  1020
TATVFGKEFK VTATIRVQRS QVTIGSSVSG NALRLTQNIP ADKQSDTLDA IKDGSTTVDA  1080
NTGGGANPSA WTNWAYSKAG HNTAEITFEY ATEQQLGQIV MYFFRDSNAV RFPDAGKTKI  1140
QISADGKNWT DLAATETIAA QESSDRVKPY TYDFAPVGAT FVKVTVTNAD TTTPSGVVCA  1200
GLTEIELKTA TSKFVTNTSA ALSSLTVNGT KVSDSVLAAG SYNTPAIIAD VKAEGEGNAS  1260
VTVLPAHDNV IRVITESEDH VTRKTFTINL GTEQEF                          1296

SEQ ID NO: 7             moltype = AA  length = 453
FEATURE                  Location/Qualifiers
source                   1..453
                         mol_type = protein
                         organism = Bifidobacterium bifidum
SEQUENCE: 7
QNRTSDFDAN WKFMLSDSVQ AQDPAFDDSA WQQVDLPHDY SITQKYSQSN EAESAYLPGG  60
TGWYRKSFTI DRDLAGKRIA INFDGVYMNA TVWFNGVKLG THPYGYSPFS FDLTGNAKFG  120
GENTIVVKVE NRLPSSRWYS GSGIYRDVTL TVTDGVHVGN NGVAIKTPSL ATQNGGDVTM  180
NLTTKVANDT EAAANITLKQ TVFPKGGKTD AAIGTVTTAS KSIAAGASAD VTSTITAASP  240
KLWSIKNPNL YTVRTEVLNG GKVLDTYDTE YGFRWTGFDA TSGFSLNGEK VKLKGVSMHH  300
DQGSLGAVAN RRAIERQVEI LQKMGVNSIR TTHNPAAKAL IDVCNEKGVL VVEEVFDMWN  360
RSKNGNTEDY GKWFGQAIAG DNAVLGGDKD ETWAKFDLTS TINRDRNAPS VIMWSLGNEM  420
MEGISGSVSG FPATSAKLVA WTKAADSTRP MTY                             453

SEQ ID NO: 8             moltype = DNA  length = 5160
FEATURE                  Location/Qualifiers
misc_feature             1..5160
                         note = Nucleotide sequence encoding an extracellular lactase
source                   1..5160
                         mol_type = other DNA
```

-continued organism = synthetic construct
SEQUENCE: 8
gcagttgaag atgcaacaag aagcgatagc acaacacaaa tgtcatcaac accggaagtt 60
gtttattcat cagcggtcga tagcaaacaa aatcgcacaa gcgattttga tgcgaactgg 120
aaatttatgc tgtcagatag cgttcaagca caagatccgg catttgatga ttcagcatgg 180
caacaagttg atctgccgca tgattatagc atcacacaga aatatagcca aagcaatgaa 240
gcagaatcag catatcttcc gggaggcaca ggctggtata gaaaaagctt tacaattgat 300
agagatctgg caggcaaacg cattgcgatt aattttgatg gcgtctatat gaatgcaaca 360
gtctggttta atggcgttaa actgggcaca catccgtatg gctattcacc gttttcattt 420
gatctgacag gcaatgcaaa atttggcgga gaaaacacaa ttgtcgtcaa agttgaaaat 480
agactgccgt catcaagatg gtattcaggc agcggcattt atagagatgt tacactgaca 540
gttacagatg gcgttcatgt tggcaataat ggcgtcgcaa ttaaaacacc gtcactggca 600
acacaaaatg gcggagatgt cacaatgaac ctgacaacaa aagtcgcgaa tgatacagaa 660
gcagcagcga acattacact gaaacagaca gtttttccga aaggcggaaa aacggatgca 720
gcaattggca cagttacaac agcatcaaaa tcaattgcag caggcgcatc agcagatgtt 780
acaagcacaa ttacagcagc aagcccgaaa ctgtggtcaa ttaaaaaccc gaacctgtat 840
acagttagaa cagaagttct gaacggaggc aaagttctgg atacatatga tacagaatat 900
ggctttcgct ggacaggctt tgatgcaaca tcaggctttt cactgaatgg cgaaaaagtc 960
aaactgaaag gcgttagcat gcatcatgat caaggctcac ttggcgcagt tgcaaataga 1020
cgcgcaattg aaagacaagt cgaaatcctg caaaaaatgg gcgtcaatag cattcgcaca 1080
acacataatc cggcagcaaa agcactgatt gatgtctgca atgaaaaagg cgttctggtt 1140
gtcgaagaag tctttgatat gtggaaccgc agcaaaaatg gcaacacgga agattatggc 1200
aaatggtttg gccaagcaat tgcaggcgat aatgcagttc tgggaggcga taaagatgaa 1260
acatgggcga aatttgatct tacatcaaca attaaccgcg atagaaatgc accgtcagtt 1320
attatgtggt cactgggcaa tgaaatgatg gaaggcattt caggctcagt ttcaggcttt 1380
ccggcaacat cagcaaaact ggttgcatgg acaaaagcag cagattcaac aagaccgatg 1440
acatatggcg ataacaaaat taaagcgaac tggaacgaat caaatacaat gggcgataat 1500
ctgacagcaa atggcggagt tgttggcaca aattattcag atggcgcaaa ctatgataaa 1560
attcgtacaa cacatccgtc atgggcaatt tatggctcag aaacagcatc agcgattaat 1620
agccgtggca tttataatag aacaacaggc ggagcacaat catcagataa acagctgaca 1680
agctatgata attcagcagt tggctgggga gcagttgcat catcagcatg gtatgatgtt 1740
gttcagagag attttgtcgc aggcacatat gtttggacag gatttgatta tctgggcgaa 1800
ccgacaccgt ggaatggcac aggctcaggc gcagttggct catggccgtc accgaaaaat 1860
agctattttg gcatcgttga tacagcaggc tttccgaaag atacatatta tttttatcag 1920
agccagtgga atgatgatgt tcatacactg catattcttc cggcatggaa tgaaaatgtt 1980
gttgcaaaag gctcaggcaa taatgttccg gttgtcgttt atacagatgc agcgaaagtg 2040
aaactgtatt ttacaccgaa aggctcaaca gaaaaaagac tgatcggcga aaaatcattt 2100
acaaaaaaaa caacagcggc aggctataca tatcaagtct atgaaggcag cgataaagat 2160
tcaacagcgc ataaaaacat gtatctgaca tggaatgttc cgtgggcaga aggcacaatt 2220
tcagcggaag cgtatgatga aaataatcgc ctgattccgg aaggcagcac agaaggcaac 2280
gcatcagtta caacaacagg caaagcagca aaactgaaag cagatgcgga tcgcaaaaca 2340
attacagcgg atggcaaaga tctgtcatat attgaagtcg atgtcacaga tgcaaatggc 2400
catattgttc cggatgcagc aaatagagtc acatttgatg ttaaaggcgc aggcaaactg 2460
gttggcgttg ataatggctc atcaccggat catgattcat atcaagcgga taaccgcaaa 2520
gcattttcag gcaaagtcct ggcaattgtt cagtcaacaa aagaagcagg cgaaattaca 2580
gttacagcaa aagcagatgg cctgcaatca agcacagtta aaattgcaac aacagcagtt 2640
ccgggaacaa gcacagaaaa aacagtccgc agcttttatt acagccgcaa ctattatgtc 2700
aaaacaggca acaaaccgat tctgccgtca gatgttgaag ttcgctattc agatggaaca 2760
agcgatagac aaaacgttac atgggatgca gtttcagatg atcaaattgc aaaagcaggc 2820
tcattttcag ttgcaggcac agttgcaggc caaaaaatta gcgttcgcgt cacaatgatt 2880
gatgaaattg gcgcactgct gaattattca gcaagcacac cggttggcac accggcagtt 2940
cttccgggat caagaccggc agtcctgccg gatggcacag tcacatcagc aaattttgca 3000
gtccattgga caaaaccggc agatacagtc tataatacag caggcacagt caaagtaccg 3060
ggaacagcaa cagtttttgg caaagaattt aaagtcacag cgacaattag agttcaaaga 3120
agccaagtta caattggctc atcagtttca ggaaatgcac tgagactgac acaaaatatt 3180
ccggcagata aacaatcaga tacactggat gcgattaaag atggctcaac aacagttgat 3240
gcaaatacag gcggaggcgc aaatccgtca gcatggacaa attgggcata ttcaaaagca 3300
ggccataaca cagcggaaat tacatttgaa tatgcgacag aacaacaact gggccagatc 3360
gtcatgtatt tttttcgcga tagcaatgca gttagatttc cggatgctgg caaaacaaaa 3420
attcagatca gcgcagatgg caaaaattgg acagatctgg cagcaacaga aacaattgca 3480
gcgcaagaat caagcgatag agtcaaaccg tatacatatg attttgcacc ggttggcgca 3540
acatttgtta aagtgacagt cacaaacgca gatacaacaa caccgtcagg cgttgtttgc 3600
gcaggcctga cagaaattga actgaaaaca gcgacaagca aatttgtcac aaatacatca 3660
gcagcactgt catcacttac agtcaatggc acaaaagttt cagattcagt tctggcagca 3720
ggctcatata acacaccggc aattatcgca gatgttaaag cggaaggcga aggcaatgca 3780
agcgttacag tccttccggc acatgataat gttattcgcg tcattacaga aagcgaagat 3840
catgtcacac gcaaaacatt tacaatcaac ctgggcacag aacaagaatt tccggctgat 3900
tcagatgaaa gagattatcc ggcagcagat atgacagtca cagttggctc agaacaaaca 3960
tcaggcacag caacagaagg accgaaaaaa tttgcagtcg atggcaacac atcaacatat 4020
tggcatagca attggacacc gacaacagtt aatgatctgt ggatcgcgtt tgaactgcaa 4080
aaaccgacaa aactggatgc actgagatat cttccgcgtc cggcaggctc aaaaaatggc 4140
agcgtcacag aatataaagt tcaggtgtca gatgatggaa caaactggac agatgcaggc 4200
tcaggcacat ggacaacgga ttatggctgg aaactggcgg aatttaatca accggtcaca 4260
acaaaacatg ttagactgaa agcggttcat acatatgcag atagcggcaa cgataaattt 4320
atgagcgcaa gcgaaattag actgagaaaa gcggtcgata caacggatat ttcaggcgca 4380
acagttacag ttccggcaaa actgacagtt gatagagttg atgcagatca tccggcaaca 4440
tttgcaacaa aagatgtcac agttacactg ggagatgcaa cactgagata tggcgttgat 4500
tatctgctgg attatgcagg caatacagca gttggcaaag caacagtgac agttagaggc 4560
attgataaat attcaggcac agtcgcgaaa acatttacaa ttgaactgaa aaatgcaccg 4620

-continued

```
gcaccggaac cgacactgac atcagttagc gtcaaaacaa aaccgagcaa actgacatat  4680
gttgtcggag atgcatttga tccggcaggc ctggttctgc aacatgatag acaagcagat  4740
agacctccgc aaccgctggt tggcgaacaa gcggatgaac gcggactgac atgcggcaca  4800
agatgcgata gagttgaaca actgcgcaaa catgaaaata gagaagcgca tagaacaggc  4860
ctggatcatc tggaatttgt tggcgcagca gatggcgcag ttggagaaca agcaacattt  4920
aaagtccatg tccatgcaga tcagggagat ggcagacatg atgatgcaga tgaacgcgat  4980
attgatccgc atgttccggt cgatcatgca gttggcgaac tggcaagagc agcatgccat  5040
catgttattg gcctgagagt cgatacacat agacttaaag caagcggctt tcaaattccg  5100
gctgatgata tggcagaaat cgatcgcatt acaggctttc atcgttttga acgccatgtc  5160

SEQ ID NO: 9            moltype = DNA  length = 2661
FEATURE                 Location/Qualifiers
misc_feature            1..2661
                        note = Nucleotide sequence encoding BIF_917
source                  1..2661
                        mol_type = other DNA
                        organism = synthetic construct
SEQUENCE: 9
gttgaagatg caacaagaag cgatagcaca acacaaatgt catcaacacc ggaagttgtt  60
tattcatcag cggtcgatag caaacaaaat cgcacaagcg attttgatgc gaactggaaa  120
tttatgctgt cagatagcgt tcaagcacaa gatccggcat ttgatgattc agcatggcaa  180
caagttgatc tgccgcatga ttatagcatc acacagaaat atagccaaag caatgaagca  240
gaatcagcat atcttccggg aggcacaggc tggtatagaa aaagctttac aattgataga  300
gatctggcag gcaaacgcat tgcgattaat tttgatggcg tctatatgaa tgcaacagtc  360
tggtttaatg gcgttaaact gggcacacat ccgtatggct attcaccgtt ttcatttgat  420
ctgacaggca atgcaaaatt tggcggagaa aacacaattg tcgtcaaagt tgaaaataga  480
ctgccgtcat caagatggta ttcaggcagc ggcatttata gagatgttac actgacagtt  540
acagatggcg ttcatgttgg caataatggc gtcgcaatta aaacaccgtc actggcaaca  600
caaaatggcg gagatgtcac aatgaacctg acaacaaaag tcgcgaatga tacagaagca  660
gcagcgaaca ttacactgaa acagacagtt tttccgaaag gcggaaaaac ggatgcagca  720
attggcacag ttacaacagc atcaaaatca attgcagcag gcgcatcagc agatgttaca  780
agcacaatta cagcagcaag cccgaaactg tggtcaatta aaaacccgaa cctgtataca  840
gttagaacag aagttctgaa cggaggcaaa gttctggata catatgatac agaatatggc  900
tttcgctgga caggctttga tgcaacatca ggcttttcac tgaatggcga aaaagtcaaa  960
ctgaaaggcg ttagcatgca tcatgatcaa ggctcacttg gcgcagttgc aaatagacgc  1020
gcaattgaaa gacaagtcga aatcctgcaa aaaatgggcg tcaatagcat tcgcacaaca  1080
cataatccgg cagcaaaagc actgattgat gtctgcaatg aaaaaggcgt tctggttgtc  1140
gaagaagtct ttgatatgtg gaaccgcagc aaaaatggca acacggaaga ttatggcaaa  1200
tggtttggcc aagcaattgc aggcgataat gcagttctgg gaggcgataa agatgaaaca  1260
tgggcgaaat ttgatcttac atcaacaatt aaccgcgata gaaatgcacc gtcagttatt  1320
atgtggtcac tgggcaatga aatgatggaa ggcatttcag gctcagtttc aggctttccg  1380
gcaacatcag caaaactggt tgcatggaca aaagcagcag attcaacaag accgatgaca  1440
tatggcgata acaaaattaa agcgaactgg aacgaatcaa atacaatggg cgataatctg  1500
acagcaaatg gcggagttgt tggcacaaat tattcagatg gcgcaaacta tgataaaatt  1560
cgtacaacac atccgtcatg ggcaatttat ggctcagaaa cagcatcagc gattaatagc  1620
cgtggcattt ataatagaac aacaggcgga gcacaatcat cagataaaca gctgacaagc  1680
tatgataatt cagcagttgg ctggggagca gttgcatcat cagcatggta tgatgttgtt  1740
cagagagatt ttgtcgcagg cacatatgtt tggacaggat ttgattatct gggcgaaccg  1800
acaccgtgga atggcacagg ctcaggcgca gttggctcat ggccgtcacc gaaaaatagc  1860
tattttggca tcgttgatac agcaggcttt ccgaaagata catattattt ttatcagagc  1920
cagtggaatg atgatgttca tacactgcat attcttccgg catggaatga aaatgttgtt  1980
gcaaaaggct caggcaataa tgttccggtt gtcgtttata cagatgcagc gaaagtgaaa  2040
ctgtatttta caccgaaagg ctcaacagaa aaaagactga tcggcgaaaa atcatttaca  2100
aaaaaaacaa cagcggcagg ctatacatat caagtctatg aaggcagcga taaagattca  2160
acagcgcata aaaacatgta tctgacatgg aatgttccgt gggcagaagg cacaatttca  2220
gcggaagcgt atgatgaaaa taatcgcctg attccggaag gcagcacaga aggcaacgca  2280
tcagttacaa caacaggcaa agcagcaaaa ctgaaagcag atgcggatcg caaaacaatt  2340
acagcggatg gcaaagatct gtcatatatt gaagtcgatg tcacagatgc aaatggccat  2400
attgttccgg atgcagcaaa tagagtcaca tttgatgtta aaggcgcagg caaactggtt  2460
ggcgttgata atggctcatc accggatcat gattcatatc aagcggataa ccgcaaagca  2520
ttttcaggca aagtcctggc aattgttcag tcaacaaaag aagcaggcga aattacagtt  2580
acagcaaaag cagatggcct gcaatcaagc acagttaaaa ttgcaacaac agcagttccg  2640
ggaacaagca cagaaaaaac a                                           2661

SEQ ID NO: 10           moltype = DNA  length = 2895
FEATURE                 Location/Qualifiers
misc_feature            1..2895
                        note = Nucleotide sequence encoding BIF_995
source                  1..2895
                        mol_type = other DNA
                        organism = synthetic construct
SEQUENCE: 10
gttgaagatg caacaagaag cgatagcaca acacaaatgt catcaacacc ggaagttgtt  60
tattcatcag cggtcgatag caaacaaaat cgcacaagcg attttgatgc gaactggaaa  120
tttatgctgt cagatagcgt tcaagcacaa gatccggcat ttgatgattc agcatggcaa  180
caagttgatc tgccgcatga ttatagcatc acacagaaat atagccaaag caatgaagca  240
gaatcagcat atcttccggg aggcacaggc tggtatagaa aaagctttac aattgataga  300
gatctggcag gcaaacgcat tgcgattaat tttgatggcg tctatatgaa tgcaacagtc  360
tggtttaatg gcgttaaact gggcacacat ccgtatggct attcaccgtt ttcatttgat  420
```

```
ctgacaggca atgcaaaatt tggcggagaa aacacaattg tcgtcaaagt tgaaaataga  480
ctgccgtcat caagatggta ttcaggcagc ggcatttata gagatgttac actgacagtt  540
acagatggcg ttcatgttgg caataatggc gtcgcaatta aaacaccgtc actggcaaca  600
caaaatggcg gagatgtcac aatgaacctg acaacaaaag tcgcgaatga tacagaagca  660
gcagcgaaca ttacactgaa acagacagtt tttccgaaag gcggaaaaac ggatgcagca  720
attggcacag ttacaacagc atcaaaatca attgcagcag gcgcatcagc agatgttaca  780
agcacaatta cagcagcaag cccgaaactg tggtcaatta aaaacccgaa cctgtataca  840
gttagaacag aagttctgaa cggaggcaaa gttctggata catatgatac agaatatggc  900
tttcgctgga caggctttga tgcaacatca ggcttttcac tgaatggcga aaaagtcaaa  960
ctgaaaggcg ttagcatgca tcatgatcaa ggctcacttg gcgcagttgc aaatagacgc  1020
gcaattgaaa gacaagtcga aatcctgcaa aaaatgggcg tcaatagcat tcgcacaaca  1080
cataatccgg cagcaaaagc actgattgat gtctgcaatg aaaaaggcgt tctggttgtc  1140
gaagaagtct ttgatatgtg gaaccgcagc aaaaatggca acacggaaga ttatggcaaa  1200
tggtttggcc aagcaattgc aggcgataat gcagttctgg gaggcgataa agatgaaaca  1260
tgggcgaaat ttgatcttac atcaacaatt aaccgcgata gaaatgcacc gtcagttatt  1320
atgtggtcac tgggcaatga aatgatggaa ggcatttcag gctcagtttc aggctttccg  1380
gcaacatcag caaaactggt tgcatggaca aaagcagcag attcaacaag accgatgaca  1440
tatggcgata acaaaattaa agcgaactgg aacgaatcaa atacaatggg cgataatctg  1500
acagcaaatg gcggagttgt tggcacaaat tattcagatg gcgcaaacta tgataaaatt  1560
cgtacaacac atccgtcatg ggcaatttat ggctcagaaa cagcatcagc gattaatagc  1620
cgtggcattt ataatagaac aacaggcgga gcacaatcat cagataaaca gctgacaagc  1680
tatgataatt cagcagttgg ctggggagca gttgcatcat cagcatggta tgatgttgtt  1740
cagagagatt ttgtcgcagg cacatatgtt tggacaggat ttgattatct gggcgaaccg  1800
acaccgtgga atggcacagg ctcaggcgca gttggctcat ggccgtcacc gaaaaatagc  1860
tattttggca tcgttgatac agcaggcttt ccgaaagata catattattt ttatcagagc  1920
cagtggaatg atgatgttca tacactgcat attcttccgg catggaatga aaatgttgtt  1980
gcaaaaggct caggcaataa tgttccggtt gtcgtttata cagatgcagc gaaagtgaaa  2040
ctgtatttta caccgaaagg ctcaacagaa aaaagactga tcggcgaaaa atcatttaca  2100
aaaaaaacaa cagcggcagg ctatacatat caagtctatg aaggcagcga taaagattca  2160
acagcgcata aaaacatgta tctgacatgg aatgttccgt gggcagaagg cacaatttca  2220
gcggaagcgt atgatgaaaa taatcgcctg attccggaag gcagcacaga aggcaacgca  2280
tcagttacaa caacaggcaa agcagcaaaa ctgaaagcag atgcggatcg caaaacaatt  2340
acagcggatg gcaaagatct gtcatatatt gaagtcgatg tcacagatgc aaatggccat  2400
attgttccgg atgcagcaaa tagagtcaca tttgatgtta aaggcgcagg caaactggtt  2460
ggcgttgata atggctcatc accggatcat gattcatatc aagcggataa ccgcaaagca  2520
ttttcaggca aagtcctggc aattgttcag tcaacaaaag aagcaggcga aattacagtt  2580
acagcaaaag cagatggcct gcaatcaagc acagttaaaa ttgcaacaac agcagttccg  2640
ggaacaagca cagaaaaaac agtccgcagc ttttattaca gccgcaacta ttatgtcaaa  2700
acaggcaaca aaccgattct gccgtcagat gttgaagttc gctattcaga tggaacaagc  2760
gatagacaaa acgttacatg ggatgcagtt tcagatgatc aaattgcaaa agcaggctca  2820
ttttcagttg caggcacagt tgcaggccaa aaaattagcg ttcgcgtcac aatgattgat  2880
gaaattggcg cactg                                                   2895

SEQ ID NO: 11          moltype = DNA  length = 3114
FEATURE                Location/Qualifiers
misc_feature           1..3114
                       note = Nucleotide sequence encoding BIF_1068
source                 1..3114
                       mol_type = other DNA
                       organism = synthetic construct
SEQUENCE: 11
gttgaagatg caacaagaag cgatagcaca acacaaatgt catcaacacc ggaagttgtt  60
tattcatcag cggtcgatag caaacaaaat cgcacaagcg attttgatgc gaactggaaa  120
tttatgctgt cagatagcgt tcaagcacaa gatccggcat ttgatgattc agcatggcaa  180
caagttgatc tgccgcatga ttatagcatc acacagaaat atagccaaag caatgaagca  240
gaatcagcat atcttccggg aggcacaggc tggtatagaa aaagctttac aattgataga  300
gatctggcag gcaaacgcat tgcgattaat tttgatggcg tctatatgaa tgcaacagtc  360
tggtttaatg gcgttaaact gggcacacat ccgtatggct attcaccgtt ttcatttgat  420
ctgacaggca atgcaaaatt tggcggagaa aacacaattg tcgtcaaagt tgaaaataga  480
ctgccgtcat caagatggta ttcaggcagc ggcatttata gagatgttac actgacagtt  540
acagatggcg ttcatgttgg caataatggc gtcgcaatta aaacaccgtc actggcaaca  600
caaaatggcg gagatgtcac aatgaacctg acaacaaaag tcgcgaatga tacagaagca  660
gcagcgaaca ttacactgaa acagacagtt tttccgaaag gcggaaaaac ggatgcagca  720
attggcacag ttacaacagc atcaaaatca attgcagcag gcgcatcagc agatgttaca  780
agcacaatta cagcagcaag cccgaaactg tggtcaatta aaaacccgaa cctgtataca  840
gttagaacag aagttctgaa cggaggcaaa gttctggata catatgatac agaatatggc  900
tttcgctgga caggctttga tgcaacatca ggcttttcac tgaatggcga aaaagtcaaa  960
ctgaaaggcg ttagcatgca tcatgatcaa ggctcacttg gcgcagttgc aaatagacgc  1020
gcaattgaaa gacaagtcga aatcctgcaa aaaatgggcg tcaatagcat tcgcacaaca  1080
cataatccgg cagcaaaagc actgattgat gtctgcaatg aaaaaggcgt tctggttgtc  1140
gaagaagtct ttgatatgtg gaaccgcagc aaaaatggca acacggaaga ttatggcaaa  1200
tggtttggcc aagcaattgc aggcgataat gcagttctgg gaggcgataa agatgaaaca  1260
tgggcgaaat ttgatcttac atcaacaatt aaccgcgata gaaatgcacc gtcagttatt  1320
atgtggtcac tgggcaatga aatgatggaa ggcatttcag gctcagtttc aggctttccg  1380
gcaacatcag caaaactggt tgcatggaca aaagcagcag attcaacaag accgatgaca  1440
tatggcgata acaaaattaa agcgaactgg aacgaatcaa atacaatggg cgataatctg  1500
acagcaaatg gcggagttgt tggcacaaat tattcagatg gcgcaaacta tgataaaatt  1560
cgtacaacac atccgtcatg ggcaatttat ggctcagaaa cagcatcagc gattaatagc  1620
cgtggcattt ataatagaac aacaggcgga gcacaatcat cagataaaca gctgacaagc  1680
```

-continued

```
tatgataatt cagcagttgg ctggggagca gttgcatcat cagcatggta tgatgttgtt  1740
cagagagatt ttgtcgcagg cacatatgtt tggacaggat ttgattatct gggcgaaccg  1800
acaccgtgga atggcacagg ctcaggcgca gttggctcat ggccgtcacc gaaaaatagc  1860
tattttggca tcgttgatac agcaggcttt ccgaaagata catattattt ttatcagagc  1920
cagtggaatg atgatgttca tacactgcat attcttccgg catggaatga aaatgttgtt  1980
gcaaaaggct caggcaataa tgttccggtt gtcgtttata cagatgcagc gaaagtgaaa  2040
ctgtatttta caccgaaagg ctcaacagaa aaaagactga tcggcgaaaa atcatttaca  2100
aaaaaaacaa cagcggcagg ctatacatat caagtctatg aaggcagcga taaagattca  2160
acagcgcata aaaacatgta tctgacatgg aatgttccgt gggcagaagg cacaatttca  2220
gcggaagcgt atgatgaaaa taatcgcctg attccggaag gcagcacaga aggcaacgca  2280
tcagttacaa caacaggcaa agcagcaaaa ctgaaagcag atgcggatcg caaaacaatt  2340
acagcggatg gcaaagatct gtcatatatt gaagtcgatg tcacagatgc aaatggccat  2400
attgttccgg atgcagcaaa tagagtcaca tttgatgtta aaggcgcagg caaactggtt  2460
ggcgttgata atggctcatc accggatcat gattcatatc aagcggataa ccgcaaagca  2520
ttttcaggca aagtcctggc aattgttcag tcaacaaaag aagcaggcga aattacagtt  2580
acagcaaaag cagatggcct gcaatcaagc acagttaaaa ttgcaacaac agcagttccg  2640
ggaacaagca cagaaaaaac agtccgcagc ttttattaca gccgcaacta ttatgtcaaa  2700
acaggcaaca aaccgattct gccgtcagat gttgaagttc gctattcaga tggaacaagc  2760
gatagacaaa acgttacatg ggatgcagtt tcagatgatc aaattgcaaa agcaggctca  2820
ttttcagttg caggcacagt tgcaggccaa aaaattagcg ttcgcgtcac aatgattgat  2880
gaaattggcg cactgctgaa ttattcagca agcacaccgg ttggcacacc ggcagttctt  2940
ccgggatcaa gaccggcagt cctgccggat ggcacagtca catcagcaaa ttttgcagtc  3000
cattggacaa aaccggcaga tacagtctat aatacagcag gcacagtcaa agtaccggga  3060
acagcaacag tttttggcaa agaatttaaa gtcacagcga caattagagt tcaa        3114

SEQ ID NO: 12          moltype = DNA  length = 3426
FEATURE                Location/Qualifiers
misc_feature           1..3426
                       note = Nucleotide sequence encoding BIF_1172
source                 1..3426
                       mol_type = other DNA
                       organism = synthetic construct
SEQUENCE: 12
gttgaagatg caacaagaag cgatagcaca acacaaatgt catcaacacc ggaagttgtt  60
tattcatcag cggtcgatag caaacaaaat cgcacaagcg attttgatgc gaactggaaa  120
tttatgctgt cagatagcgt tcaagcacaa gatccggcat ttgatgattc agcatggcaa  180
caagttgatc tgccgcatga ttatagcatc acacagaaat atagccaaag caatgaagca  240
gaatcagcat atcttccggg aggcacaggc tggtatagaa aaagctttac aattgataga  300
gatctggcag gcaaacgcat tgcgattaat tttgatggcg tctatatgaa tgcaacagtc  360
tggtttaatg gcgttaaact gggcacacat ccgtatggct attcaccgtt ttcatttgat  420
ctgacaggca atgcaaaatt tggcggagaa aacacaattg tcgtcaaagt tgaaaataga  480
ctgccgtcat caagatggta ttcaggcagc ggcatttata gagatgttac actgacagtt  540
acagatggcg ttcatgttgg caataatggc gtcgcaatta aaacaccgtc actggcaaca  600
caaaatggcg gagatgtcac aatgaacctg acaacaaaag tcgcgaatga tacagaagca  660
gcagcgaaca ttacactgaa acagacagtt tttccgaaag gcggaaaaac ggatgcagca  720
attggcacag ttacaacagc atcaaaatca attgcagcag gcgcatcagc agatgttaca  780
agcacaatta cagcagcaag cccgaaactg tggtcaatta aaaacccgaa cctgtataca  840
gttagaacag aagttctgaa cggaggcaaa gttctggata catatgatac agaatatggc  900
tttcgctgga caggctttga tgcaacatca ggcttttcac tgaatggcga aaaagtcaaa  960
ctgaaaggcg ttagcatgca tcatgatcaa ggctcacttg gcgcagttgc aaatagacgc  1020
gcaattgaaa gacaagtcga aatcctgcaa aaaatgggcg tcaatagcat tcgcacaaca  1080
cataatccgg cagcaaaagc actgattgat gtctgcaatg aaaaaggcgt tctggttgtc  1140
gaagaagtct ttgatatgtg gaaccgcagc aaaaatggca acacggaaga ttatggcaaa  1200
tggtttggcc aagcaattgc aggcgataat gcagttctgg gaggcgataa agatgaaaca  1260
tgggcgaaat ttgatcttac atcaacaatt aaccgcgata gaaatgcacc gtcagttatt  1320
atgtggtcac tgggcaatga aatgatggaa ggcatttcag gctcagtttc aggctttccg  1380
gcaacatcag caaaactggt tgcatggaca aaagcagcag attcaacaag accgatgaca  1440
tatggcgata acaaaattaa agcgaactgg aacgaatcaa atacaatggg cgataatctg  1500
acagcaaatg gcggagttgt tggcacaaat tattcagatg gcgcaaacta tgataaaatt  1560
cgtacaacac atccgtcatg ggcaatttat ggctcagaaa cagcatcagc gattaatagc  1620
cgtggcattt ataatagaac aacaggcgga gcacaatcat cagataaaca gctgacaagc  1680
tatgataatt cagcagttgg ctggggagca gttgcatcat cagcatggta tgatgttgtt  1740
cagagagatt ttgtcgcagg cacatatgtt tggacaggat ttgattatct gggcgaaccg  1800
acaccgtgga atggcacagg ctcaggcgca gttggctcat ggccgtcacc gaaaaatagc  1860
tattttggca tcgttgatac agcaggcttt ccgaaagata catattattt ttatcagagc  1920
cagtggaatg atgatgttca tacactgcat attcttccgg catggaatga aaatgttgtt  1980
gcaaaaggct caggcaataa tgttccggtt gtcgtttata cagatgcagc gaaagtgaaa  2040
ctgtatttta caccgaaagg ctcaacagaa aaaagactga tcggcgaaaa atcatttaca  2100
aaaaaaacaa cagcggcagg ctatacatat caagtctatg aaggcagcga taaagattca  2160
acagcgcata aaaacatgta tctgacatgg aatgttccgt gggcagaagg cacaatttca  2220
gcggaagcgt atgatgaaaa taatcgcctg attccggaag gcagcacaga aggcaacgca  2280
tcagttacaa caacaggcaa agcagcaaaa ctgaaagcag atgcggatcg caaaacaatt  2340
acagcggatg gcaaagatct gtcatatatt gaagtcgatg tcacagatgc aaatggccat  2400
attgttccgg atgcagcaaa tagagtcaca tttgatgtta aaggcgcagg caaactggtt  2460
ggcgttgata atggctcatc accggatcat gattcatatc aagcggataa ccgcaaagca  2520
ttttcaggca aagtcctggc aattgttcag tcaacaaaag aagcaggcga aattacagtt  2580
acagcaaaag cagatggcct gcaatcaagc acagttaaaa ttgcaacaac agcagttccg  2640
ggaacaagca cagaaaaaac agtccgcagc ttttattaca gccgcaacta ttatgtcaaa  2700
acaggcaaca aaccgattct gccgtcagat gttgaagttc gctattcaga tggaacaagc  2760
```

-continued

```
gatagacaaa acgttacatg ggatgcagtt tcagatgatc aaattgcaaa agcaggctca  2820
ttttcagttg caggcacagt tgcaggccaa aaaattagcg ttcgcgtcac aatgattgat  2880
gaaattggcg cactgctgaa ttattcagca agcacaccgg ttggcacacc ggcagttctt  2940
ccgggatcaa gaccggcagt cctgccggat ggcacagtca catcagcaaa ttttgcagtc  3000
cattggacaa aaccggcaga tacagtctat aatacagcag gcacagtcaa agtaccggga  3060
acagcaacag tttttggcaa agaatttaaa gtcacagcga caattagagt tcaaagaagc  3120
caagttacaa ttggctcatc agtttcagga aatgcactga gactgacaca aaatattccg  3180
gcagataaac aatcagatac actggatgcg attaaagatg gctcaacaac agttgatgca  3240
aatacaggcg gaggcgcaaa tccgtcagca tggacaaatt gggcatattc aaaagcaggc  3300
cataacacag cggaaattac atttgaatat gcgacagaac aacaactggg ccagatcgtc  3360
atgtattttt ttcgcgatag caatgcagtt agatttccgg atgctggcaa aacaaaaatt  3420
cagatc                                                             3426
```

```
SEQ ID NO: 13          moltype = DNA  length = 3633
FEATURE                Location/Qualifiers
misc_feature           1..3633
                       note = Nucleotide sequence encoding BIF_1241
source                 1..3633
                       mol_type = other DNA
                       organism = synthetic construct
SEQUENCE: 13
gttgaagatg caacaagaag cgatagcaca acacaaatgt catcaacacc ggaagttgtt  60
tattcatcag cggtcgatag caaacaaaat cgcacaagcg attttgatgc gaactggaaa  120
tttatgctgt cagatagcgt tcaagcacaa gatccggcat ttgatgattc agcatggcaa  180
caagttgatc tgccgcatga ttatagcatc acacagaaat atagccaaag caatgaagca  240
gaatcagcat atcttccggg aggcacaggc tggtatagaa aaagctttac aattgataga  300
gatctggcag gcaaacgcat tgcgattaat tttgatggcg tctatatgaa tgcaacagtc  360
tggtttaatg gcgttaaact gggcacacat ccgtatggct attcaccgtt ttcatttgat  420
ctgacaggca atgcaaaatt tggcggagaa aacacaattg tcgtcaaagt tgaaaataga  480
ctgccgtcat caagatggta ttcaggcagc ggcatttata gagatgttac actgacagtt  540
acagatggcg ttcatgttgg caataatggc gtcgcaatta aaacaccgtc actggcaaca  600
caaaatggcg gagatgtcac aatgaacctg acaacaaaag tcgcgaatga tacagaagca  660
gcagcgaaca ttacactgaa acagacagtt tttccgaaag gcggaaaaac ggatgcagca  720
attggcacag ttacaacagc atcaaaatca attgcagcag gcgcatcagc agatgttaca  780
agcacaatta cagcagcaag cccgaaactg tggtcaatta aaaacccgaa cctgtataca  840
gttagaacag aagttctgaa cggaggcaaa gttctggata catatgatac agaatatggc  900
tttcgctgga caggctttga tgcaacatca ggcttttcac tgaatggcga aaaagtcaaa  960
ctgaaaggcg ttagcatgca tcatgatcaa ggctcacttg gcgcagttgc aaatagacgc  1020
gcaattgaaa gacaagtcga aatcctgcaa aaaatgggcg tcaatagcat tcgcacaaca  1080
cataatccgg cagcaaaagc actgattgat gtctgcaatg aaaaaggcgt tctggttgtc  1140
gaagaagtct ttgatatgtg gaaccgcagc aaaaatggca acacggaaga ttatggcaaa  1200
tggtttggcc aagcaattgc aggcgataat gcagttctgg gaggcgataa agatgaaaca  1260
tgggcgaaat ttgatcttac atcaacaatt aaccgcgata gaaatgcacc gtcagttatt  1320
atgtggtcac tgggcaatga aatgatggaa ggcatttcag gctcagtttc aggctttccg  1380
gcaacatcag caaaactggt tgcatggaca aaagcagcag attcaacaag accgatgaca  1440
tatggcgata acaaaattaa agcgaactgg aacgaatcaa atacaatggg cgataatctg  1500
acagcaaatg gcggagttgt tggcacaaat tattcagatg gcgcaaacta tgataaaatt  1560
cgtacaacac atccgtcatg ggcaatttat ggctcagaaa cagcatcagc gattaatagc  1620
cgtggcattt ataatagaac aacaggcgga gcacaatcat cagataaaca gctgacaagc  1680
tatgataatt cagcagttgg ctggggagca gttgcatcat cagcatggta tgatgttgtt  1740
cagagagatt ttgtcgcagg cacatatgtt tggacaggat ttgattatct gggcgaaccg  1800
acaccgtgga atggcacagg ctcaggcgca gttggctcat ggccgtcacc gaaaaatagc  1860
tattttggca tcgttgatac agcaggcttt ccgaaagata catattattt ttatcagagc  1920
cagtggaatg atgatgttca tacactgcat attcttccgg catggaatga aaatgttgtt  1980
gcaaaaggct caggcaataa tgttccggtt gtcgtttata cagatgcagc gaaagtgaaa  2040
ctgtatttta caccgaaagg ctcaacagaa aaaagactga tcggcgaaaa atcatttaca  2100
aaaaaaacaa cagcggcagg ctatacatat caagtctatg aaggcagcga taaagattca  2160
acagcgcata aaaacatgta tctgacatgg aatgttccgt gggcagaagg cacaatttca  2220
gcggaagcgt atgatgaaaa taatcgcctg attccggaag gcagcacaga aggcaacgca  2280
tcagttacaa caacaggcaa agcagcaaaa ctgaaagcag atgcggatcg caaaacaatt  2340
acagcggatg gcaaagatct gtcatatatt gaagtcgatg tcacagatgc aaatggccat  2400
attgttccgg atgcagcaaa tagagtcaca tttgatgtta aaggcgcagg caaactggtt  2460
ggcgttgata atggctcatc accggatcat gattcatatc aagcggataa ccgcaaagca  2520
ttttcaggca aagtcctggc aattgttcag tcaacaaaag aagcaggcga aattacagtt  2580
acagcaaaag cagatggcct gcaatcaagc acagttaaaa ttgcaacaac agcagttccg  2640
ggaacaagca cagaaaaaac agtccgcagc ttttattaca gccgcaacta ttatgtcaaa  2700
acaggcaaca aaccgattct gccgtcagat gttgaagttc gctattcaga tggaacaagc  2760
gatagacaaa acgttacatg ggatgcagtt tcagatgatc aaattgcaaa agcaggctca  2820
ttttcagttg caggcacagt tgcaggccaa aaaattagcg ttcgcgtcac aatgattgat  2880
gaaattggcg cactgctgaa ttattcagca agcacaccgg ttggcacacc ggcagttctt  2940
ccgggatcaa gaccggcagt cctgccggat ggcacagtca catcagcaaa ttttgcagtc  3000
cattggacaa aaccggcaga tacagtctat aatacagcag gcacagtcaa agtaccggga  3060
acagcaacag tttttggcaa agaatttaaa gtcacagcga caattagagt tcaaagaagc  3120
caagttacaa ttggctcatc agtttcagga aatgcactga gactgacaca aaatattccg  3180
gcagataaac aatcagatac actggatgcg attaaagatg gctcaacaac agttgatgca  3240
aatacaggcg gaggcgcaaa tccgtcagca tggacaaatt gggcatattc aaaagcaggc  3300
cataacacag cggaaattac atttgaatat gcgacagaac aacaactggg ccagatcgtc  3360
atgtattttt ttcgcgatag caatgcagtt agatttccgg atgctggcaa aacaaaaatt  3420
cagatcagcg cagatggcaa aaattggaca gatctggcag caacagaaac aattgcagcg  3480
```

-continued

```
caagaatcaa gcgatagagt caaaccgtat acatatgatt ttgcaccggt tggcgcaaca  3540
tttgttaaag tgacagtcac aaacgcagat acaacaacac cgtcaggcgt tgtttgcgca  3600
ggcctgacag aaattgaact gaaaacagcg aca                               3633

SEQ ID NO: 14          moltype = DNA  length = 3888
FEATURE                Location/Qualifiers
misc_feature           1..3888
                       note = Nucleotide sequence encoding BIF_1326
source                 1..3888
                       mol_type = other DNA
                       organism = synthetic construct
SEQUENCE: 14
gttgaagatg caacaagaag cgatagcaca acacaaatgt catcaacacc ggaagttgtt  60
tattcatcag cggtcgatag caaacaaaat cgcacaagcg attttgatgc gaactggaaa  120
tttatgctgt cagatagcgt tcaagcacaa gatccggcat ttgatgattc agcatggcaa  180
caagttgatc tgccgcatga ttatagcatc acacagaaat atagccaaag caatgaagca  240
gaatcagcat atcttccggg aggcacaggc tggtatagaa aaagctttac aattgataga  300
gatctggcag gcaaacgcat tgcgattaat tttgatggcg tctatatgaa tgcaacagtc  360
tggtttaatg gcgttaaact gggcacacat ccgtatggct attcaccgtt ttcatttgat  420
ctgacaggca atgcaaaatt tggcggagaa aacacaattg tcgtcaaagt tgaaaataga  480
ctgccgtcat caagatggta ttcaggcagc ggcatttata gagatgttac actgacagtt  540
acagatggcg ttcatgttgg caataatggc gtcgcaatta aaacaccgtc actggcaaca  600
caaaatggcg gagatgtcac aatgaacctg acaacaaaag tcgcgaatga tacagaagca  660
gcagcgaaca ttacactgaa acagacagtt tttccgaaag gcggaaaaac ggatgcagca  720
attggcacag ttacaacagc atcaaaatca attgcagcag gcgcatcagc agatgttaca  780
agcacaatta cagcagcaag cccgaaactg tggtcaatta aaaacccgaa cctgtataca  840
gttagaacag aagttctgaa cggaggcaaa gttctggata catatgatac agaatatggc  900
tttcgctgga caggctttga tgcaacatca ggcttttcac tgaatggcga aaaagtcaaa  960
ctgaaaggcg ttagcatgca tcatgatcaa ggctcacttg gcgcagttgc aaatagacgc  1020
gcaattgaaa gacaagtcga aatcctgcaa aaaatgggcg tcaatagcat tcgcacaaca  1080
cataatccgg cagcaaaagc actgattgat gtctgcaatg aaaaaggcgt tctggttgtc  1140
gaagaagtct ttgatatgtg gaaccgcagc aaaaatggca acacggaaga ttatggcaaa  1200
tggtttggcc aagcaattgc aggcgataat gcagttctgg gaggcgataa agatgaaaca  1260
tgggcgaaat ttgatcttac atcaacaatt aaccgcgata gaaatgcacc gtcagttatt  1320
atgtggtcac tgggcaatga aatgatggaa ggcatttcag gctcagtttc aggctttccg  1380
gcaacatcag caaaactggt tgcatggaca aaagcagcag attcaacaag accgatgaca  1440
tatggcgata acaaaattaa agcgaactgg aacgaatcaa atacaatggg cgataatctg  1500
acagcaaatg gcggagttgt tggcacaaat tattcagatg gcgcaaacta tgataaaatt  1560
cgtacaacac atccgtcatg ggcaatttat ggctcagaaa cagcatcagc gattaatagc  1620
cgtggcattt ataatagaac aacaggcgga gcacaatcat cagataaaca gctgacaagc  1680
tatgataatt cagcagttgg ctggggagca gttgcatcat cagcatggta tgatgttgtt  1740
cagagagatt ttgtcgcagg cacatatgtt tggacaggat ttgattatct gggcgaaccg  1800
acaccgtgga atggcacagg ctcaggcgca gttggctcat ggccgtcacc gaaaaatagc  1860
tattttggca tcgttgatac agcaggcttt ccgaaagata catattattt ttatcagagc  1920
cagtggaatg atgatgttca tacactgcat attcttccgg catggaatga aaatgttgtt  1980
gcaaaaggct caggcaataa tgttccggtt gtcgtttata cagatgcagc gaaagtgaaa  2040
ctgtatttta caccgaaagg ctcaacagaa aaaagactga tcggcgaaaa atcatttaca  2100
aaaaaaacaa cagcggcagg ctatacatat caagtctatg aaggcagcga taaagattca  2160
acagcgcata aaaacatgta tctgacatgg aatgttccgt gggcagaagg cacaatttca  2220
gcggaagcgt atgatgaaaa taatcgcctg attccggaag gcagcacaga aggcaacgca  2280
tcagttacaa caacaggcaa agcagcaaaa ctgaaagcag atgcggatcg caaaacaatt  2340
acagcggatg gcaaagatct gtcatatatt gaagtcgatg tcacagatgc aaatggccat  2400
attgttccgg atgcagcaaa tagagtcaca tttgatgtta aaggcgcagg caaactggtt  2460
ggcgttgata atggctcatc accggatcat gattcatatc aagcggataa ccgcaaagca  2520
ttttcaggca aagtcctggc aattgttcag tcaacaaaag aagcaggcga aattacagtt  2580
acagcaaaag cagatggcct gcaatcaagc acagttaaaa ttgcaacaac agcagttccg  2640
ggaacaagca cagaaaaaac agtccgcagc ttttattaca gccgcaacta ttatgtcaaa  2700
acaggcaaca aaccgattct gccgtcagat gttgaagttc gctattcaga tggaacaagc  2760
gatagacaaa acgttacatg ggatgcagtt tcagatgatc aaattgcaaa agcaggctca  2820
ttttcagttg caggcacagt tgcaggccaa aaaattagcg ttcgcgtcac aatgattgat  2880
gaaattggcg cactgctgaa ttattcagca agcacaccgg ttggcacacc ggcagttctt  2940
ccgggatcaa gaccggcagt cctgccggat ggcacagtca catcagcaaa ttttgcagtc  3000
cattggacaa aaccggcaga tacagtctat aatacagcag gcacagtcaa agtaccggga  3060
acagcaacag tttttggcaa agaatttaaa gtcacagcga caattagagt tcaaagaagc  3120
caagttacaa ttggctcatc agtttcagga aatgcactga gactgacaca aaatattccg  3180
gcagataaac aatcagatac actggatgcg attaaagatg gctcaacaac agttgatgca  3240
aatacaggcg gaggcgcaaa tccgtcagca tggacaaatt gggcatattc aaaagcaggc  3300
cataacacag cggaaattac atttgaatat gcgacagaac aacaactggg ccagatcgtc  3360
atgtattttt ttcgcgatag caatgcagtt agatttccgg atgctggcaa aacaaaaatt  3420
cagatcagcg cagatggcaa aaattggaca gatctggcag caacagaaac aattgcagcg  3480
caagaatcaa gcgatagagt caaaccgtat acatatgatt ttgcaccggt tggcgcaaca  3540
tttgttaaag tgacagtcac aaacgcagat acaacaacac cgtcaggcgt tgtttgcgca  3600
ggcctgacag aaattgaact gaaaacagcg acaagcaaat ttgtcacaaa tacatcagca  3660
gcactgtcat cacttacagt caatggcaca aaagtttcag attcagttct ggcagcaggc  3720
tcatataaca caccggcaat tatcgcagat gttaaagcgg aaggcgaagg caatgcaagc  3780
gttacagtcc ttccggcaca tgataatgtt attcgcgtca ttacagaaag cgaagatcat  3840
gtcacacgca aaacatttac aatcaacctg ggcacagaac aagaattt               3888

SEQ ID NO: 15          moltype = DNA  length = 30
```

-continued

```
FEATURE                 Location/Qualifiers
misc_feature            1..30
                        note = Forward primer for generation of BIF variants
source                  1..30
                        mol_type = other DNA
                        organism = synthetic construct
SEQUENCE: 15
ggggtaacta gtggaagatg caacaagaag                                  30

SEQ ID NO: 16           moltype = DNA  length = 35
FEATURE                 Location/Qualifiers
misc_feature            1..35
                        note = Reverse primer for BIF917
source                  1..35
                        mol_type = other DNA
                        organism = synthetic construct
SEQUENCE: 16
gcgcttaatt aattatgttt tttctgtgct tgttc                            35

SEQ ID NO: 17           moltype = DNA  length = 38
FEATURE                 Location/Qualifiers
misc_feature            1..38
                        note = Reverse primer for BIF995
source                  1..38
                        mol_type = other DNA
                        organism = synthetic construct
SEQUENCE: 17
gcgcttaatt aattacagtg cgccaatttc atcaatca                         38

SEQ ID NO: 18           moltype = DNA  length = 35
FEATURE                 Location/Qualifiers
misc_feature            1..35
                        note = Reverse primer for BIF1068
source                  1..35
                        mol_type = other DNA
                        organism = synthetic construct
SEQUENCE: 18
gcgcttaatt aattattgaa ctctaattgt cgctg                            35

SEQ ID NO: 19           moltype = DNA  length = 36
FEATURE                 Location/Qualifiers
misc_feature            1..36
                        note = Reverse primer for BIF1241
source                  1..36
                        mol_type = other DNA
                        organism = synthetic construct
SEQUENCE: 19
gcgcttaatt aattatgtcg ctgttttcag ttcaat                           36

SEQ ID NO: 20           moltype = DNA  length = 35
FEATURE                 Location/Qualifiers
misc_feature            1..35
                        note = Reverse primer for BIF1326
source                  1..35
                        mol_type = other DNA
                        organism = synthetic construct
SEQUENCE: 20
gcgcttaatt aattaaaatt cttgttctgt gccca                            35

SEQ ID NO: 21           moltype = DNA  length = 38
FEATURE                 Location/Qualifiers
misc_feature            1..38
                        note = Reverse primer for BIF1478
source                  1..38
                        mol_type = other DNA
                        organism = synthetic construct
SEQUENCE: 21
gcgcttaatt aattatctca gtctaatttc gcttgcgc                         38

SEQ ID NO: 22           moltype = AA  length = 1720
FEATURE                 Location/Qualifiers
source                  1..1720
                        mol_type = protein
                        organism = Bifidobacterium bifidum
SEQUENCE: 22
VEDATRSDST TQMSSTPEVV YSSAVDSKQN RTSDFDANWK FMLSDSVQAQ DPAFDDSAWQ  60
QVDLPHDYSI TQKYSQSNEA ESAYLPGGTG WYRKSFTIDR DLAGKRIAIN FDGVYMNATV  120
WFNGVKLGTH PYGYSPFSFD LTGNAKFGGE NTIVVKVENR LPSSRWYSGS GIYRDVTLTV  180
TDGVHVGNNG VAIKTPSLAT QNGGDVTMNL TTKVANDTEA AANITLKQTV FPKGGKTDAA  240
```

-continued

```
IGTVTTASKS IAAGASADVT STITAASPKL WSIKNPNLYT VRTEVLNGGK VLDTYDTEYG  300
FRWTGFDATS GFSLNGEKVK LKGVSMHHDQ GSLGAVANRR AIERQVEILQ KMGVNSIRTT  360
HNPAAKALID VCNEKGVLVV EEVFDMWNRS KNGNTEDYGK WFGQAIAGDN AVLGGDKDET  420
WAKFDLTSTI NRDRNAPSVI MWSLGNEMME GISGSVSGFP ATSAKLVAWT KAADSTRPMT  480
YGDNKIKANW NESNTMGDNL TANGGVVGTN YSDGANYDKI RTTHPSWAIY GSETASAINS  540
RGIYNRTTGG AQSSDKQLTS YDNSAVGWGA VASSAWYDVV QRDFVAGTYV WTGFDYLGEP  600
TPWNGTGSGA VGSWPSPKNS YFGIVDTAGF PKDTYYFYQS QWNDDVHTLH ILPAWNENVV  660
AKGSGNNVPV VVYTDAAKVK LYFTPKGSTE KRLIGEKSFT KKTTAAGYTY QVYEGSDKDS  720
TAHKNMYLTW NVPWAEGTIS AEAYDENNRL IPEGSTEGNA SVTTTGKAAK LKADADRKTI  780
TADGKDLSYI EVDVTDANGH IVPDAANRVT FDVKGAGKLV GVDNGSSPDH DSYQADNRKA  840
FSGKVLAIVQ STKEAGEITV TAKADGLQSS TVKIATTAVP GTSTEKTVRS FYYSRNYYVK  900
TGNKPILPSD VEVRYSDGTS DRQNVTWDAV SDDQIAKAGS FSVAGTVAGQ KISVRVTMID  960
EIGALLNYSA STPVGTPAVL PGSRPAVLPD GTVTSANFAV HWTKPADTVY NTAGTVKVPG  1020
TATVFGKEFK VTATIRVQRS QVTIGSSVSG NALRLTQNIP ADKQSDTLDA IKDGSTTVDA  1080
NTGGGANPSA WTNWAYSKAG HNTAEITFEY ATEQQLGQIV MYFFRDSNAV RFPDAGKTKI  1140
QISADGKNWT DLAATETIAA QESSDRVKPY TYDFAPVGAT FVKVTVTNAD TTTPSGVVCA  1200
GLTEIELKTA TSKFVTNTSA ALSSLTVNGT KVSDSVLAAG SYNTPAIIAD VKAEGEGNAS  1260
VTVLPAHDNV IRVITESEDH VTRKTFTINL GTEQEFPADS DERDYPAADM TVTVGSEQTS  1320
GTATEGPKKF AVDGNTSTYW HSNWTPTTVN DLWIAFELQK PTKLDALRYL PRPAGSKNGS  1380
VTEYKVQVSD DGTNWTDAGS GTWTTDYGWK LAEFNQPVTT KHVRLKAVHT YADSGNDKFM  1440
SASEIRLRKA VDTTDISGAT VTVPAKLTVD RVDADHPATF ATKDVTVTLG DATLRYGVDY  1500
LLDYAGNTAV GKATVTVRGI DKYSGTVAKT FTIELKNAPA PEPTLTSVSV KTKPSKLTYV  1560
VGDAFDPAGL VLQHDRQADR PPQPLVGEQA DERGLTCGTR CDRVEQLRKH ENREAHRTGL  1620
DHLEFVGAAD GAVGEQATFK VHVHADQGDG RHDDADERDI DPHVPVDHAV GELARAACHH  1680
VIGLRVDTHR LKASGFQIPA DDMAEIDRIT GFHRFERHVG                        1720

SEQ ID NO: 23          moltype = AA  length = 30
FEATURE                Location/Qualifiers
source                 1..30
                       mol_type = protein
                       organism = Bifidobacterium bifidum
SEQUENCE: 23
VRSKKLWISL LFALALIFTM AFGSTSSAQA                                   30
```